(12) United States Patent
Raucher et al.

(10) Patent No.: US 9,682,118 B1
(45) Date of Patent: *Jun. 20, 2017

(54) INHIBITION OF METASTASIS BY CELL PENETRATING PEPTIDES

(75) Inventors: Drazen Raucher, Madison, MS (US); Gene Bidwell, III, Jackson, MS (US)

(73) Assignee: University of Mississippi Medical Center, Jackson, MS (US)

( * ) Notice: Subject to any disclaimer, the term of this patent is extended or adjusted under 35 U.S.C. 154(b) by 673 days.

This patent is subject to a terminal disclaimer.

(21) Appl. No.: 12/789,236

(22) Filed: May 27, 2010

Related U.S. Application Data

(63) Continuation-in-part of application No. 12/422,975, filed on Apr. 13, 2009, now abandoned, which is a continuation-in-part of application No. 12/162,283, filed as application No. PCT/US2007/061240 on Jan. 29, 2007, now Pat. No. 8,252,740.

(60) Provisional application No. 61/044,398, filed on Apr. 11, 2008, provisional application No. 60/762,919, filed on Jan. 27, 2006.

(51) Int. Cl.
*A61K 38/00* (2006.01)

(52) U.S. Cl.
CPC .................................... *A61K 38/00* (2013.01)

(58) Field of Classification Search
CPC ...................................................... A61K 38/00
USPC .................................. 530/300, 350; 514/1.1
See application file for complete search history.

(56) References Cited

U.S. PATENT DOCUMENTS

| | | | |
|---|---|---|---|
| 6,582,926 B1 * | 6/2003 | Chilkoti | 435/7.1 |
| 7,329,638 B2 * | 2/2008 | Yang et al. | 424/185.1 |
| 7,951,924 B2 * | 5/2011 | Sebti | 536/23.1 |
| 2003/0124742 A1 | 7/2003 | Prakash | |
| 2004/0234497 A1 | 11/2004 | Luo et al. | |

FOREIGN PATENT DOCUMENTS

WO  WO2006/001806  1/2006

OTHER PUBLICATIONS

Cowled et al. (Cancer Res. Feb. 15, 1987; 47: 971-974).*
Suggitt et al. (Clin. Cancer Res. Feb. 1, 2005; 11: 971-981).*
Gura (Science. 1997; 278: 1041-1042).*
Dennis (Nature. Aug. 7, 2006; 442: 739-741).*
Saijo et al. (Cancer Sci. Oct. 2004; 95 (10): 772-776).*
Kelland (Eur. J. Cancer. Apr. 2004; 40 (6): 827-836).*
Bergers et al. (Current Opinion in Genetics and Development. 2000; 10: 120-127).*
Pooga et al. (Methods Mol. Biol. 2005; 298: 77-89).*
Raucher et al. (Cancer Res. Oct. 1, 2001; 61 (19): 7163-70).*
Chilkoti et al. (Adv. Drug Deliv. Rev. Sep. 13, 2002; 54 (5): 613-30).*
Meyer et al. (Cancer Res. Feb. 15, 2001; 61 (4): 1548-54).*
Trabbic-Carlson et al. (Protein Eng. Des. Sel. Jan. 2004;17(1): 57-66).*
Elmquist et al. (Exp. Cell Res. Oct. 2001; 269 (2): 237-44).*
Deshayes et al. (Cell Mol. Life Sci. Aug. 2005; 62 (16): 1839-49).*
Letoha et al. (J. Mol. Recognit. Sep.-Oct. 2003; 16 (5): 272-9).*
Ziegler et al. (Biochem. Jan. 2005; 44 (1): 138-48).*
Gupta et al. (Adv. Drug. Deliv. Rev. Feb. 2005; 57 (4): 637-51).*
Dreher, M.R. et al., Evaluation of an elastin-like polypeptide-doxorubincin conjugate for cancer therapy; Journal of Controlled Release; 2003; vol. 91; pp. 31-43.
Massodi, I, et al., Evalution of cell penetrating peptides fused to elastin-like polypeptide for drug delivery; Journal of controlled Release; 2005; vol. 108; pp. 396-408.
Meyer, D.E., et al., Targeting a Genetically Engineered Elastin-like Polypeptide to Solid Tumors by Local Hyperthemia; Cancer Research; Feb. 15, 2001; vol. 61.
Massodi, I, et al., Inhibition of ovarian cancer cell metastasis by a fusion polypeptide Tat-ELP; Clin Exp Metastasis 2009; 26; pp. 251-260.
Bidwell, G.L., et al Targeting a c-Myc inhibitory polypeptide to specific intracellular compartments using cell penetrating peptides, Jouranal of Controlled Relase; 2009.
Massodi, I., et al A thermally responsive Tat-elastin-like polypeptide fusion protein induces membrane leakage, apoptosis, and cell death in human breast cancer cells; Journal of Drug Targeting; Nov. 2007; 15(9); pp. 611-622.
Bidwell GL, III, et al Application of thermally responsive polypeptides directed against c-Myc transcriptional function for cancer therapy; Mol Cancer Ther 2005; 4(7): 1076-85.
Bidwell GL, III, et al Enhancing the antiproliferative effect of topoisomerase II inhibitors using a polypeptide inhibitor of c-Myc; Biochemical Pharmacology; 2006; 71; pp. 248-256.
Bidwell GL, III, et al Development of elastin-like polypeptide for thermally targeted delivery of doxorubicin; Biochemical Pharmacology, 2007; 73; pp. 620-631.
Bidwell GL, III, et al A thermally targeted elastin-like polypeptide-doxorubicin conjugate overcomes drug resistance; Invest New Drugs; 2007; 25; pp. 313-326.

* cited by examiner

*Primary Examiner* — Stephen Rawlings
(74) *Attorney, Agent, or Firm* — Stites & Harbison PLLC; Mandy Wilson Decker; Rachel Rutledge

(57) ABSTRACT

A compound including a cell penetrating peptide (CPP) and elastin-like polypeptide (ELP), and a method for use thereof, are useful for inhibiting the proliferation of cancer.

8 Claims, 12 Drawing Sheets

SEQUENCE LISTING

```
<160> NUMBER OF SEQ ID NOS: 37

<210> SEQ ID NO 1
<211> LENGTH: 11
<212> TYPE: PRT
<213> ORGANISM: Artificial Sequence
<220> FEATURE:
<223> OTHER INFORMATION: Tat CPP

<400> SEQUENCE: 1

Tyr Gly Arg Lys Lys Arg Arg Gln Arg Arg Arg
1               5                   10

<210> SEQ ID NO 2
<211> LENGTH: 16
```

```
<212> TYPE: PRT
<213> ORGANISM: Artificial
<220> FEATURE:
<223> OTHER INFORMATION: Antp CPP

<400> SEQUENCE: 2

Arg Gln Ile Lys Ile Trp Phe Gln Asn Arg Arg Met Lys Trp Lys Lys
1               5                   10                  15

<210> SEQ ID NO 3
<211> LENGTH: 24
<212> TYPE: PRT
<213> ORGANISM: Artificial Sequence
<220> FEATURE:
<223> OTHER INFORMATION: Bac-7 CPP

<400> SEQUENCE: 3

Arg Arg Ile Arg Pro Arg Pro Pro Arg Leu Pro Arg Pro Arg Pro Arg
1               5                   10                  15

Pro Leu Pro Phe Pro Arg Pro Gly
            20

<210> SEQ ID NO 4
<211> LENGTH: 18
<212> TYPE: PRT
<213> ORGANISM: Artificial Sequence
<220> FEATURE:
<223> OTHER INFORMATION: SynB1 CPP

<400> SEQUENCE: 4

Arg Gly Gly Arg Leu Ser Tyr Ser Arg Arg Phe Ser Thr Ser Thr
1               5                   10                  15

Gly Arg

<210> SEQ ID NO 5
<211> LENGTH: 28
<212> TYPE: PRT
<213> ORGANISM: Artificial Sequence
<220> FEATURE:
<223> OTHER INFORMATION: SynB1-NLS CPP

<400> SEQUENCE: 5

Arg Gly Gly Arg Leu Ser Tyr Ser Arg Arg Phe Ser Thr Ser Thr
1               5                   10                  15

Gly Arg Trp Ser Gln Pro Lys Lys Lys Arg Lys Val
            20                  25

<210> SEQ ID NO 6
<211> LENGTH: 7
<212> TYPE: PRT
<213> ORGANISM: Artificial Sequence
<220> FEATURE:
<223> OTHER INFORMATION: R-7 CPP

<400> SEQUENCE: 6

Arg Arg Arg Arg Arg Arg Arg
1               5

<210> SEQ ID NO 7
<211> LENGTH: 8
<212> TYPE: PRT
<213> ORGANISM: Artificial Sequence
<220> FEATURE:
<223> OTHER INFORMATION: R-8 CPP

<400> SEQUENCE: 7
```

```
Arg Arg Arg Arg Arg Arg Arg Arg
1               5

<210> SEQ ID NO 8
<211> LENGTH: 9
<212> TYPE: PRT
<213> ORGANISM: Artificial Sequence
<220> FEATURE:
<223> OTHER INFORMATION: R-9 CPP

<400> SEQUENCE: 8

Arg Arg Arg Arg Arg Arg Arg Arg Arg
1               5

<210> SEQ ID NO 9
<211> LENGTH: 10
<212> TYPE: PRT
<213> ORGANISM: Artificial Sequence
<220> FEATURE:
<223> OTHER INFORMATION: R-10 CPP

<400> SEQUENCE: 9

Arg Arg Arg Arg Arg Arg Arg Arg Arg Arg
1               5                   10

<210> SEQ ID NO 10
<211> LENGTH: 11
<212> TYPE: PRT
<213> ORGANISM: Artificial Sequence
<220> FEATURE:
<223> OTHER INFORMATION: R-11 CPP

<400> SEQUENCE: 10

Arg Arg Arg Arg Arg Arg Arg Arg Arg Arg Arg
1               5                   10

<210> SEQ ID NO 11
<211> LENGTH: 34
<212> TYPE: PRT
<213> ORGANISM: Artificial Sequence
<220> FEATURE:
<223> OTHER INFORMATION: VP22 CPP

<400> SEQUENCE: 11

Asp Ala Ala Thr Ala Thr Arg Gly Arg Ser Ala Ala Ser Arg Pro Thr
1               5                   10                  15

Gln Arg Pro Arg Ala Pro Ala Arg Ser Ala Ser Arg Pro Arg Arg Pro
            20                  25                  30

Val Gln

<210> SEQ ID NO 12
<211> LENGTH: 27
<212> TYPE: PRT
<213> ORGANISM: Artificial Sequence
<220> FEATURE:
<223> OTHER INFORMATION: Trans CPP

<400> SEQUENCE: 12

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 13
```

```
<211> LENGTH: 18
<212> TYPE: PRT
<213> ORGANISM: Artificial Sequence
<220> FEATURE:
<223> OTHER INFORMATION: MAP CPP

<400> SEQUENCE: 13

Lys Leu Ala Leu Lys Leu Ala Leu Lys Ala Leu Lys Ala Ala Leu Lys
1               5                   10                  15

Leu Ala

<210> SEQ ID NO 14
<211> LENGTH: 18
<212> TYPE: PRT
<213> ORGANISM: Artificial Sequence
<220> FEATURE:
<223> OTHER INFORMATION: pVEC CPP

<400> SEQUENCE: 14

Leu Leu Ile Ile Leu Arg Arg Arg Ile Arg Lys Gln Ala His Ala His
1               5                   10                  15

Ser Lys

<210> SEQ ID NO 15
<211> LENGTH: 16
<212> TYPE: PRT
<213> ORGANISM: Artificial Sequence
<220> FEATURE:
<223> OTHER INFORMATION: MTS CPP

<400> SEQUENCE: 15

Ala Ala Val Ala Leu Leu Pro Ala Val Leu Leu Ala Leu Leu Ala Pro
1               5                   10                  15

<210> SEQ ID NO 16
<211> LENGTH: 24
<212> TYPE: PRT
<213> ORGANISM: Artificial Sequence
<220> FEATURE:
<223> OTHER INFORMATION: nCT-derived CPP

<400> SEQUENCE: 16

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 17
<211> LENGTH: 27
<212> TYPE: PRT
<213> ORGANISM: Artificial Sequence
<220> FEATURE:
<223> OTHER INFORMATION: MPG CPP

<400> SEQUENCE: 17

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 18
<211> LENGTH: 21
<212> TYPE: PRT
<213> ORGANISM: Artificial Sequence
<220> FEATURE:
```

```
<223> OTHER INFORMATION: Buforin 2 CPP

<400> SEQUENCE: 18

Thr Arg Ser Ser Arg Ala Gly Leu Gln Phe Pro Val Gly Arg Val His
1               5                   10                  15

Arg Leu Leu Arg Lys
            20

<210> SEQ ID NO 19
<211> LENGTH: 21
<212> TYPE: PRT
<213> ORGANISM: Artificial Sequence
<220> FEATURE:
<223> OTHER INFORMATION: PEP-1 CPP

<400> SEQUENCE: 19

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 20
<211> LENGTH: 23
<212> TYPE: PRT
<213> ORGANISM: Artificial Sequence
<220> FEATURE:
<223> OTHER INFORMATION: Magainin 2 CPP

<400> SEQUENCE: 20

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 21
<211> LENGTH: 758
<212> TYPE: PRT
<213> ORGANISM: Artificial Sequence
<220> FEATURE:
<223> OTHER INFORMATION: ELP 1

<400> SEQUENCE: 21

Met Ser Lys Gly Pro Gly Val Gly Val Pro Gly Val Gly Val Pro Gly
1               5                   10                  15

Gly Gly Val Pro Gly Ala Gly Val Pro Gly Val Gly Val Pro Gly Val
            20                  25                  30

Gly Val Pro Gly Val Gly Val Pro Gly Gly Gly Val Pro Gly Ala Gly
        35                  40                  45

Val Pro Gly Gly Gly Val Pro Gly Val Gly Val Pro Gly Val Gly Val
    50                  55                  60

Pro Gly Gly Gly Val Pro Gly Ala Gly Val Pro Gly Val Gly Val Pro
65                  70                  75                  80

Gly Val Gly Val Pro Gly Val Gly Val Pro Gly Gly Gly Val Pro Gly
                85                  90                  95

Ala Gly Val Pro Gly Gly Gly Val Pro Gly Val Gly Val Pro Gly Val
            100                 105                 110

Gly Val Pro Gly Gly Gly Val Pro Gly Ala Gly Val Pro Gly Val Gly
        115                 120                 125

Val Pro Gly Val Gly Val Pro Gly Val Gly Val Pro Gly Gly Gly Val
    130                 135                 140
```

```
Pro Gly Ala Gly Val Pro Gly Gly Val Pro Gly Val Pro
145                 150                 155                 160

Gly Val Gly Val Pro Gly Gly Val Pro Gly Ala Gly Val Pro Gly
                165                 170                 175

Val Gly Val Pro Gly Val Gly Val Pro Gly Val Gly Val Pro Gly Gly
                180                 185                 190

Gly Val Pro Gly Ala Gly Val Pro Gly Gly Val Pro Gly Val Gly
            195                 200                 205

Val Pro Gly Val Gly Val Pro Gly Gly Val Pro Gly Ala Gly Val
        210                 215                 220

Pro Gly Val Gly Val Pro Gly Val Gly Val Pro Gly Gly Val Pro
225                 230                 235                 240

Gly Gly Gly Val Pro Gly Ala Gly Val Pro Gly Gly Val Pro Gly
                245                 250                 255

Val Gly Val Pro Gly Val Gly Val Pro Gly Gly Val Pro Gly Ala
                260                 265                 270

Gly Val Pro Gly Val Gly Val Pro Gly Val Gly Val Pro Gly Val Gly
            275                 280                 285

Val Pro Gly Gly Val Pro Gly Ala Gly Val Pro Gly Gly Val
        290                 295                 300

Pro Gly Val Gly Val Pro Gly Val Gly Val Pro Gly Gly Val Pro
305                 310                 315                 320

Gly Ala Gly Val Pro Gly Val Gly Val Pro Gly Val Gly Val Pro Gly
                325                 330                 335

Val Gly Val Pro Gly Gly Val Pro Gly Ala Gly Val Pro Gly Gly
            340                 345                 350

Gly Val Pro Gly Val Gly Val Pro Gly Val Gly Val Pro Gly Gly
            355                 360                 365

Val Pro Gly Ala Gly Val Pro Gly Gly Val Pro Gly Val Gly Val
        370                 375                 380

Pro Gly Val Gly Val Pro Gly Gly Val Pro Gly Ala Gly Val Pro
385                 390                 395                 400

Gly Gly Gly Val Pro Gly Val Gly Val Pro Gly Val Gly Val Pro Gly
                405                 410                 415

Gly Gly Val Pro Gly Ala Gly Val Pro Gly Gly Val Pro Gly Val
            420                 425                 430

Gly Val Pro Gly Val Gly Val Pro Gly Gly Val Pro Gly Ala Gly
            435                 440                 445

Val Pro Gly Gly Val Pro Gly Val Gly Val Pro Gly Val Gly Val
        450                 455                 460

Pro Gly Gly Gly Val Pro Gly Ala Gly Val Pro Gly Gly Val Pro
465                 470                 475                 480

Gly Val Gly Val Pro Gly Val Gly Val Pro Gly Gly Val Pro Gly
                485                 490                 495

Ala Gly Val Pro Gly Gly Val Pro Gly Val Gly Val Pro Gly Val
                500                 505                 510

Gly Val Pro Gly Gly Gly Val Pro Gly Ala Gly Val Pro Gly Val Gly
            515                 520                 525

Val Pro Gly Val Gly Val Pro Gly Val Gly Val Pro Gly Gly Val
        530                 535                 540

Pro Gly Ala Gly Val Pro Gly Gly Gly Val Pro Gly Val Gly Val Pro
545                 550                 555                 560

Gly Val Gly Val Pro Gly Gly Gly Val Pro Gly Ala Gly Val Pro Gly
```

```
                565                 570                 575
Val Gly Val Pro Gly Val Gly Val Pro Gly Val Gly Val Pro Gly Gly
                580                 585                 590
Gly Val Pro Gly Ala Gly Val Pro Gly Gly Gly Val Pro Gly Val Gly
                595                 600                 605
Val Pro Gly Val Gly Val Pro Gly Gly Gly Val Pro Gly Ala Gly Val
                610                 615                 620
Pro Gly Val Gly Val Pro Gly Val Gly Val Pro Gly Gly Gly Val Pro
625                 630                 635                 640
Gly Gly Gly Val Pro Gly Ala Gly Val Pro Gly Gly Gly Val Pro Gly
                645                 650                 655
Val Gly Val Pro Gly Val Gly Val Pro Gly Gly Gly Val Pro Gly Ala
                660                 665                 670
Gly Val Pro Gly Val Gly Val Pro Gly Val Gly Val Pro Gly Val Gly
                675                 680                 685
Val Pro Gly Gly Gly Val Pro Gly Ala Gly Val Pro Gly Gly Gly Val
                690                 695                 700
Pro Gly Val Gly Val Pro Gly Val Gly Val Pro Gly Gly Gly Val Pro
705                 710                 715                 720
Gly Ala Gly Val Pro Gly Val Gly Val Pro Gly Val Gly Val Pro Gly
                725                 730                 735
Val Gly Val Pro Gly Gly Gly Val Pro Gly Ala Gly Val Pro Gly Gly
                740                 745                 750
Gly Val Pro Gly Trp Pro
                755

<210> SEQ ID NO 22
<211> LENGTH: 808
<212> TYPE: PRT
<213> ORGANISM: Artificial Sequence
<220> FEATURE:
<223> OTHER INFORMATION: ELP 2

<400> SEQUENCE: 22

Met Ser Lys Gly Pro Gly Val Gly Val Pro Gly Ala Gly Val Pro Gly
1               5                   10                  15
Gly Gly Val Pro Gly Ala Gly Val Pro Gly Gly Gly Val Pro Gly Ala
                20                  25                  30
Gly Val Pro Gly Gly Gly Val Pro Gly Ala Gly Val Pro Gly Gly Gly
                35                  40                  45
Val Pro Gly Ala Gly Val Pro Gly Gly Gly Val Pro Gly Ala Gly Val
                50                  55                  60
Pro Gly Gly Gly Val Pro Gly Ala Gly Val Pro Gly Gly Gly Val Pro
65                  70                  75                  80
Gly Ala Gly Val Pro Gly Val Gly Val Pro Gly Ala Gly Val Pro Gly
                85                  90                  95
Gly Gly Val Pro Gly Ala Gly Val Pro Gly Gly Gly Val Pro Gly Ala
                100                 105                 110
Gly Val Pro Gly Gly Gly Val Pro Gly Ala Gly Val Pro Gly Gly Gly
                115                 120                 125
Val Pro Gly Ala Gly Val Pro Gly Gly Gly Val Pro Gly Ala Gly Val
                130                 135                 140
Pro Gly Gly Gly Val Pro Gly Ala Gly Val Pro Gly Gly Gly Val Pro
145                 150                 155                 160
Gly Ala Gly Val Pro Gly Val Gly Val Pro Gly Ala Gly Val Pro Gly
```

-continued

```
                165                 170                 175
Gly Gly Val Pro Gly Ala Gly Val Pro Gly Gly Val Pro Gly Ala
            180                 185                 190
Gly Val Pro Gly Gly Val Pro Gly Ala Gly Val Pro Gly Gly Gly
            195                 200                 205
Val Pro Gly Ala Gly Val Pro Gly Gly Gly Val Pro Gly Ala Gly Val
210                 215                 220
Pro Gly Gly Gly Val Pro Gly Ala Gly Val Pro Gly Gly Gly Val Pro
225                 230                 235                 240
Gly Ala Gly Val Pro Gly Val Gly Val Pro Gly Ala Gly Val Pro Gly
            245                 250                 255
Gly Gly Val Pro Gly Ala Gly Val Pro Gly Gly Gly Val Pro Gly Ala
            260                 265                 270
Gly Val Pro Gly Gly Gly Val Pro Gly Ala Gly Val Pro Gly Gly Gly
            275                 280                 285
Val Pro Gly Ala Gly Val Pro Gly Gly Gly Val Pro Gly Ala Gly Val
            290                 295                 300
Pro Gly Gly Gly Val Pro Gly Ala Gly Val Pro Gly Gly Gly Val Pro
305                 310                 315                 320
Gly Ala Gly Val Pro Gly Val Gly Val Pro Gly Ala Gly Val Pro Gly
            325                 330                 335
Gly Gly Val Pro Gly Ala Gly Val Pro Gly Gly Gly Val Pro Gly Ala
            340                 345                 350
Gly Val Pro Gly Gly Gly Val Pro Gly Ala Gly Val Pro Gly Gly Gly
            355                 360                 365
Val Pro Gly Ala Gly Val Pro Gly Gly Gly Val Pro Gly Ala Gly Val
            370                 375                 380
Pro Gly Gly Gly Val Pro Gly Ala Gly Val Pro Gly Gly Gly Val Pro
385                 390                 395                 400
Gly Ala Gly Val Pro Gly Val Gly Val Pro Gly Ala Gly Val Pro Gly
            405                 410                 415
Gly Gly Val Pro Gly Ala Gly Val Pro Gly Gly Gly Val Pro Gly Ala
            420                 425                 430
Gly Val Pro Gly Gly Gly Val Pro Gly Ala Gly Val Pro Gly Gly Gly
            435                 440                 445
Val Pro Gly Ala Gly Val Pro Gly Gly Gly Val Pro Gly Ala Gly Val
            450                 455                 460
Pro Gly Gly Gly Val Pro Gly Ala Gly Val Pro Gly Gly Gly Val Pro
465                 470                 475                 480
Gly Ala Gly Val Pro Gly Val Gly Val Pro Gly Ala Gly Val Pro Gly
            485                 490                 495
Gly Gly Val Pro Gly Ala Gly Val Pro Gly Gly Gly Val Pro Gly Ala
            500                 505                 510
Gly Val Pro Gly Gly Gly Val Pro Gly Ala Gly Val Pro Gly Gly Gly
            515                 520                 525
Val Pro Gly Ala Gly Val Pro Gly Gly Gly Val Pro Gly Ala Gly Val
            530                 535                 540
Pro Gly Gly Gly Val Pro Gly Ala Gly Val Pro Gly Gly Gly Val Pro
545                 550                 555                 560
Gly Ala Gly Val Pro Gly Val Gly Val Pro Gly Ala Gly Val Pro Gly
            565                 570                 575
Gly Gly Val Pro Gly Ala Gly Val Pro Gly Gly Gly Val Pro Gly Ala
            580                 585                 590
```

-continued

Gly Val Pro Gly Gly Val Pro Gly Ala Gly Val Pro Gly Gly
            595                 600                 605

Val Pro Gly Ala Gly Val Pro Gly Gly Gly Val Pro Gly Ala Gly Val
            610                 615                 620

Pro Gly Gly Gly Val Pro Gly Ala Gly Val Pro Gly Gly Gly Val Pro
625                 630                 635                 640

Gly Ala Gly Val Pro Gly Val Gly Val Pro Gly Ala Gly Val Pro Gly
            645                 650                 655

Gly Gly Val Pro Gly Ala Gly Val Pro Gly Gly Gly Val Pro Gly Ala
            660                 665                 670

Gly Val Pro Gly Gly Gly Val Pro Gly Ala Gly Val Pro Gly Gly Gly
            675                 680                 685

Val Pro Gly Ala Gly Val Pro Gly Gly Gly Val Pro Gly Ala Gly Val
            690                 695                 700

Pro Gly Gly Gly Val Pro Gly Ala Gly Val Pro Gly Gly Gly Val Pro
705                 710                 715                 720

Gly Ala Gly Val Pro Gly Val Gly Val Pro Gly Ala Gly Val Pro Gly
            725                 730                 735

Gly Gly Val Pro Gly Ala Gly Val Pro Gly Gly Gly Val Pro Gly Ala
            740                 745                 750

Gly Val Pro Gly Gly Gly Val Pro Gly Ala Gly Val Pro Gly Gly Gly
            755                 760                 765

Val Pro Gly Ala Gly Val Pro Gly Gly Gly Val Pro Gly Ala Gly Val
            770                 775                 780

Pro Gly Gly Gly Val Pro Gly Ala Gly Val Pro Gly Gly Gly Val Pro
785                 790                 795                 800

Gly Ala Gly Val Pro Gly Trp Pro
            805

<210> SEQ ID NO 23
<211> LENGTH: 773
<212> TYPE: PRT
<213> ORGANISM: Artificial Sequence
<220> FEATURE:
<223> OTHER INFORMATION: Tat-ELP1

<400> SEQUENCE: 23

Met Tyr Gly Arg Lys Lys Arg Arg Gln Arg Arg Gly Gly Pro Gly
1               5                   10                  15

Val Gly Val Pro Gly Val Gly Val Pro Gly Gly Gly Val Pro Gly Ala
            20                  25                  30

Gly Val Pro Gly Val Gly Val Pro Gly Val Gly Val Pro Gly Val Gly
            35                  40                  45

Val Pro Gly Gly Gly Val Pro Gly Ala Gly Val Pro Gly Gly Gly Val
            50                  55                  60

Pro Gly Val Gly Val Pro Gly Val Gly Val Pro Gly Gly Gly Val Pro
65                  70                  75                  80

Gly Ala Gly Val Pro Gly Val Gly Val Pro Gly Val Gly Val Pro Gly
            85                  90                  95

Val Gly Val Pro Gly Gly Val Pro Gly Ala Gly Val Pro Gly Gly
            100                 105                 110

Gly Val Pro Gly Val Gly Val Pro Gly Val Gly Val Pro Gly Gly Gly
            115                 120                 125

Val Pro Gly Ala Gly Val Pro Gly Val Gly Val Pro Gly Val Gly Val
            130                 135                 140

```
Pro Gly Val Gly Val Pro Gly Gly Val Pro Gly Ala Gly Val Pro
145                 150                 155                 160

Gly Gly Gly Val Pro Gly Val Gly Val Pro Gly Val Gly Val Pro Gly
                165                 170                 175

Gly Gly Val Pro Gly Ala Gly Val Pro Gly Val Gly Val Pro Gly Val
            180                 185                 190

Gly Val Pro Gly Val Gly Val Pro Gly Gly Val Pro Gly Ala Gly
        195                 200                 205

Val Pro Gly Gly Gly Val Pro Gly Val Gly Val Pro Gly Val Gly Val
210                 215                 220

Pro Gly Gly Gly Val Pro Gly Ala Gly Val Pro Gly Val Gly Val Pro
225                 230                 235                 240

Gly Val Gly Val Pro Gly Val Gly Val Pro Gly Gly Gly Val Pro Gly
                245                 250                 255

Ala Gly Val Pro Gly Gly Gly Val Pro Gly Val Gly Val Pro Gly Val
            260                 265                 270

Gly Val Pro Gly Gly Gly Val Pro Gly Ala Gly Val Pro Gly Val Gly
        275                 280                 285

Val Pro Gly Val Gly Val Pro Gly Val Gly Val Pro Gly Gly Gly Val
290                 295                 300

Pro Gly Ala Gly Val Pro Gly Gly Gly Val Pro Gly Val Gly Val Pro
305                 310                 315                 320

Gly Val Gly Val Pro Gly Gly Gly Val Pro Gly Ala Gly Val Pro Gly
                325                 330                 335

Val Gly Val Pro Gly Val Gly Val Pro Gly Val Gly Val Pro Gly Gly
            340                 345                 350

Gly Val Pro Gly Ala Gly Val Pro Gly Gly Gly Val Pro Gly Val Gly
        355                 360                 365

Val Pro Gly Val Gly Val Pro Gly Gly Gly Val Pro Gly Ala Gly Val
370                 375                 380

Pro Gly Val Gly Val Pro Gly Val Gly Val Pro Gly Val Gly Val Pro
385                 390                 395                 400

Gly Gly Gly Val Pro Gly Ala Gly Val Pro Gly Gly Gly Val Pro Gly
                405                 410                 415

Val Gly Val Pro Gly Val Gly Val Pro Gly Gly Gly Val Pro Gly Ala
            420                 425                 430

Gly Val Pro Gly Val Gly Val Pro Gly Val Gly Val Pro Gly Val Gly
        435                 440                 445

Val Pro Gly Gly Gly Val Pro Gly Ala Gly Val Pro Gly Gly Gly Val
450                 455                 460

Pro Gly Val Gly Val Pro Gly Val Gly Val Pro Gly Gly Gly Val Pro
465                 470                 475                 480

Gly Ala Gly Val Pro Gly Val Gly Val Pro Gly Val Gly Val Pro Gly
                485                 490                 495

Val Gly Val Pro Gly Gly Gly Val Pro Gly Ala Gly Val Pro Gly Gly
            500                 505                 510

Gly Val Pro Gly Val Gly Val Pro Gly Val Gly Val Pro Gly Gly Gly
        515                 520                 525

Val Pro Gly Ala Gly Val Pro Gly Gly Gly Val Pro Gly Val Gly Val
530                 535                 540

Pro Gly Val Gly Val Pro Gly Gly Gly Val Pro Gly Ala Gly Val Pro
545                 550                 555                 560
```

```
Gly Gly Gly Val Pro Gly Val Gly Val Pro Gly Val Gly Val Pro Gly
                565                 570                 575

Gly Gly Val Pro Gly Ala Gly Val Pro Gly Val Gly Val Pro Gly Val
            580                 585                 590

Gly Val Pro Gly Val Gly Val Pro Gly Gly Gly Val Pro Gly Ala Gly
        595                 600                 605

Val Pro Gly Gly Gly Val Pro Gly Val Gly Val Pro Gly Val Gly Val
    610                 615                 620

Pro Gly Gly Gly Val Pro Gly Ala Gly Val Pro Gly Val Gly Val Pro
625                 630                 635                 640

Gly Val Gly Val Pro Gly Val Gly Val Pro Gly Gly Gly Val Pro Gly
            645                 650                 655

Ala Gly Val Pro Gly Gly Gly Val Pro Gly Val Gly Val Pro Gly Val
                660                 665                 670

Gly Val Pro Gly Gly Gly Val Pro Gly Ala Gly Val Pro Gly Val Gly
        675                 680                 685

Val Pro Gly Val Gly Val Pro Gly Val Gly Val Pro Gly Gly Gly Val
    690                 695                 700

Pro Gly Ala Gly Val Pro Gly Gly Gly Val Pro Gly Val Gly Val Pro
705                 710                 715                 720

Gly Val Gly Val Pro Gly Gly Gly Val Pro Gly Ala Gly Val Pro Gly
            725                 730                 735

Val Gly Val Pro Gly Val Gly Val Pro Gly Val Gly Val Pro Gly Gly
                740                 745                 750

Gly Val Pro Gly Ala Gly Val Pro Gly Gly Gly Val Pro Gly Trp Pro
            755                 760                 765

Gly Ser Gly Gly Cys
        770

<210> SEQ ID NO 24
<211> LENGTH: 823
<212> TYPE: PRT
<213> ORGANISM: Artificial Sequence
<220> FEATURE:
<223> OTHER INFORMATION: ELP-Tat2

<400> SEQUENCE: 24

Met Tyr Gly Arg Lys Lys Arg Arg Gln Arg Arg Gly Gly Pro Gly
1               5                   10                  15

Val Gly Val Pro Gly Ala Gly Val Pro Gly Gly Gly Val Pro Gly Ala
            20                  25                  30

Gly Val Pro Gly Gly Gly Val Pro Gly Ala Gly Val Pro Gly Gly Gly
        35                  40                  45

Val Pro Gly Ala Gly Val Pro Gly Gly Gly Val Pro Gly Ala Gly Val
    50                  55                  60

Pro Gly Gly Gly Val Pro Gly Ala Gly Val Pro Gly Gly Gly Val Pro
65                  70                  75                  80

Gly Ala Gly Val Pro Gly Gly Gly Val Pro Gly Ala Gly Val Pro Gly
                85                  90                  95

Val Gly Val Pro Gly Ala Gly Val Pro Gly Gly Gly Val Pro Gly Ala
            100                 105                 110

Gly Val Pro Gly Gly Gly Val Pro Gly Ala Gly Val Pro Gly Gly Gly
        115                 120                 125

Val Pro Gly Ala Gly Val Pro Gly Gly Gly Val Pro Gly Ala Gly Val
    130                 135                 140
```

```
Pro Gly Gly Gly Val Pro Gly Ala Gly Val Pro Gly Gly Gly Val Pro
145                 150                 155                 160

Gly Ala Gly Val Pro Gly Gly Val Pro Gly Ala Gly Val Pro Gly
                165                 170                 175

Val Gly Val Pro Gly Ala Gly Val Pro Gly Gly Gly Val Pro Gly Ala
                180                 185                 190

Gly Val Pro Gly Gly Gly Val Pro Gly Ala Gly Val Pro Gly Gly Gly
            195                 200                 205

Val Pro Gly Ala Gly Val Pro Gly Gly Gly Val Pro Gly Ala Gly Val
        210                 215                 220

Pro Gly Gly Gly Val Pro Gly Ala Gly Val Pro Gly Gly Gly Val Pro
225                 230                 235                 240

Gly Ala Gly Val Pro Gly Gly Val Pro Gly Ala Gly Val Pro Gly
                245                 250                 255

Val Gly Val Pro Gly Ala Gly Val Pro Gly Gly Gly Val Pro Gly Ala
                260                 265                 270

Gly Val Pro Gly Gly Gly Val Pro Gly Ala Gly Val Pro Gly Gly Gly
            275                 280                 285

Val Pro Gly Ala Gly Val Pro Gly Gly Gly Val Pro Gly Ala Gly Val
        290                 295                 300

Pro Gly Gly Gly Val Pro Gly Ala Gly Val Pro Gly Gly Gly Val Pro
305                 310                 315                 320

Gly Ala Gly Val Pro Gly Gly Gly Val Pro Gly Ala Gly Val Pro Gly
                325                 330                 335

Val Gly Val Pro Gly Ala Gly Val Pro Gly Gly Gly Val Pro Gly Ala
                340                 345                 350

Gly Val Pro Gly Gly Gly Val Pro Gly Ala Gly Val Pro Gly Gly Gly
            355                 360                 365

Val Pro Gly Ala Gly Val Pro Gly Gly Gly Val Pro Gly Ala Gly Val
        370                 375                 380

Pro Gly Gly Gly Val Pro Gly Ala Gly Val Pro Gly Gly Gly Val Pro
385                 390                 395                 400

Gly Ala Gly Val Pro Gly Gly Val Pro Gly Ala Gly Val Pro Gly
                405                 410                 415

Val Gly Val Pro Gly Ala Gly Val Pro Gly Gly Gly Val Pro Gly Ala
                420                 425                 430

Gly Val Pro Gly Gly Gly Val Pro Gly Ala Gly Val Pro Gly Gly Gly
            435                 440                 445

Val Pro Gly Ala Gly Val Pro Gly Gly Gly Val Pro Gly Ala Gly Val
        450                 455                 460

Pro Gly Gly Gly Val Pro Gly Ala Gly Val Pro Gly Gly Gly Val Pro
465                 470                 475                 480

Gly Ala Gly Val Pro Gly Gly Val Pro Gly Ala Gly Val Pro Gly
                485                 490                 495

Val Gly Val Pro Gly Ala Gly Val Pro Gly Gly Gly Val Pro Gly Ala
                500                 505                 510

Gly Val Pro Gly Gly Gly Val Pro Gly Ala Gly Val Pro Gly Gly Gly
            515                 520                 525

Val Pro Gly Ala Gly Val Pro Gly Gly Gly Val Pro Gly Ala Gly Val
        530                 535                 540

Pro Gly Gly Gly Val Pro Gly Ala Gly Val Pro Gly Gly Gly Val Pro
545                 550                 555                 560

Gly Ala Gly Val Pro Gly Gly Gly Val Pro Gly Ala Gly Val Pro Gly
```

```
                    565                 570                 575
Val Gly Val Pro Gly Ala Gly Val Pro Gly Gly Val Pro Gly Ala
                580                 585                 590

Gly Val Pro Gly Gly Val Pro Ala Gly Val Pro Gly Gly Gly
            595                 600                 605

Val Pro Gly Ala Gly Val Pro Gly Gly Gly Val Pro Gly Ala Gly Val
            610                 615                 620

Pro Gly Gly Gly Val Pro Gly Ala Gly Val Pro Gly Gly Gly Val Pro
625                 630                 635                 640

Gly Ala Gly Val Pro Gly Gly Val Pro Ala Gly Val Pro Gly
                645                 650                 655

Val Gly Val Pro Gly Ala Gly Val Pro Gly Gly Val Pro Gly Ala
                660                 665                 670

Gly Val Pro Gly Gly Val Pro Ala Gly Val Pro Gly Gly Gly
            675                 680                 685

Val Pro Gly Ala Gly Val Pro Gly Gly Val Pro Gly Ala Gly Val
            690                 695                 700

Pro Gly Gly Gly Val Pro Gly Ala Gly Val Pro Gly Gly Gly Val Pro
705                 710                 715                 720

Gly Ala Gly Val Pro Gly Gly Val Pro Ala Gly Val Pro Gly
                725                 730                 735

Val Gly Val Pro Gly Ala Gly Val Pro Gly Gly Val Pro Gly Ala
                740                 745                 750

Gly Val Pro Gly Gly Val Pro Ala Gly Val Pro Gly Gly Gly
            755                 760                 765

Val Pro Gly Ala Gly Val Pro Gly Gly Val Pro Gly Ala Gly Val
            770                 775                 780

Pro Gly Gly Gly Val Pro Gly Ala Gly Val Pro Gly Gly Gly Val Pro
785                 790                 795                 800

Gly Ala Gly Val Pro Gly Gly Val Pro Ala Gly Val Pro Gly
                805                 810                 815

Trp Pro Gly Ser Gly Gly Cys
                820

<210> SEQ ID NO 25
<211> LENGTH: 774
<212> TYPE: PRT
<213> ORGANISM: Artificial Sequence
<220> FEATURE:
<223> OTHER INFORMATION: Antp-ELP1

<400> SEQUENCE: 25

Met Arg Gln Ile Lys Ile Trp Phe Gln Asn Arg Arg Met Lys Trp Lys
1               5                   10                  15

Lys Gly Cys Gly Pro Gly Val Gly Val Pro Gly Val Gly Val Pro Gly
                20                  25                  30

Gly Gly Val Pro Gly Ala Gly Val Pro Gly Val Gly Val Pro Gly Val
            35                  40                  45

Gly Val Pro Gly Val Gly Val Pro Gly Gly Gly Val Pro Gly Ala Gly
        50                  55                  60

Val Pro Gly Gly Gly Val Pro Gly Val Gly Val Pro Gly Val Gly Val
65                  70                  75                  80

Pro Gly Gly Gly Val Pro Gly Ala Gly Val Pro Gly Val Gly Val Pro
                85                  90                  95

Gly Val Gly Val Pro Gly Val Gly Val Pro Gly Gly Gly Val Pro Gly
```

-continued

```
                100                 105                 110
Ala Gly Val Pro Gly Gly Val Pro Gly Val Gly Val Pro Gly Val
            115                 120                 125
Gly Val Pro Gly Gly Val Pro Gly Ala Gly Val Pro Gly Val Gly
            130                 135                 140
Val Pro Gly Val Gly Val Pro Gly Val Gly Val Pro Gly Gly Gly Val
145                 150                 155                 160
Pro Gly Ala Gly Val Pro Gly Gly Val Pro Gly Val Gly Val Pro
            165                 170                 175
Gly Val Gly Val Pro Gly Gly Val Pro Gly Ala Gly Val Pro Gly
            180                 185                 190
Val Gly Val Pro Gly Val Gly Val Pro Gly Val Gly Val Pro Gly Gly
            195                 200                 205
Gly Val Pro Gly Ala Gly Val Pro Gly Gly Val Pro Gly Val Gly
            210                 215                 220
Val Pro Gly Val Gly Val Pro Gly Gly Gly Val Pro Gly Ala Gly Val
225                 230                 235                 240
Pro Gly Val Gly Val Pro Gly Val Gly Val Pro Gly Val Gly Val Pro
            245                 250                 255
Gly Gly Gly Val Pro Gly Ala Gly Val Pro Gly Gly Val Pro Gly
            260                 265                 270
Val Gly Val Pro Gly Val Gly Val Pro Gly Gly Gly Val Pro Gly Ala
            275                 280                 285
Gly Val Pro Gly Val Gly Val Pro Gly Val Gly Val Pro Gly Val Gly
            290                 295                 300
Val Pro Gly Gly Gly Val Pro Gly Ala Gly Val Pro Gly Gly Val
305                 310                 315                 320
Pro Gly Val Gly Val Pro Gly Val Gly Val Pro Gly Gly Gly Val Pro
            325                 330                 335
Gly Ala Gly Val Pro Gly Val Gly Val Pro Gly Val Gly Val Pro Gly
            340                 345                 350
Val Gly Val Pro Gly Gly Gly Val Pro Gly Ala Gly Val Pro Gly Gly
            355                 360                 365
Gly Val Pro Gly Val Gly Val Pro Gly Val Gly Val Pro Gly Gly Gly
            370                 375                 380
Val Pro Gly Ala Gly Val Pro Gly Val Gly Val Pro Gly Val Gly Val
385                 390                 395                 400
Pro Gly Val Gly Val Pro Gly Gly Gly Val Pro Gly Ala Gly Val Pro
            405                 410                 415
Gly Gly Gly Val Pro Gly Val Gly Val Pro Gly Val Gly Val Pro Gly
            420                 425                 430
Gly Gly Val Pro Gly Ala Gly Val Pro Gly Val Gly Val Pro Gly Val
            435                 440                 445
Gly Val Pro Gly Val Gly Val Pro Gly Gly Gly Val Pro Gly Ala Gly
            450                 455                 460
Val Pro Gly Gly Gly Val Pro Gly Val Gly Val Pro Gly Val Gly Val
465                 470                 475                 480
Pro Gly Gly Gly Val Pro Gly Ala Gly Val Pro Gly Val Gly Val Pro
            485                 490                 495
Gly Val Gly Val Pro Gly Val Gly Val Pro Gly Gly Gly Val Pro Gly
            500                 505                 510
Ala Gly Val Pro Gly Gly Gly Val Pro Gly Val Gly Val Pro Gly Val
            515                 520                 525
```

-continued

Gly Val Pro Gly Gly Val Pro Gly Ala Gly Val Pro Gly Val Gly
                530                 535                 540

Val Pro Gly Val Gly Val Pro Gly Val Gly Val Pro Gly Gly Gly Val
545                 550                 555                 560

Pro Gly Ala Gly Val Pro Gly Gly Val Pro Gly Val Gly Val Pro
                565                 570                 575

Gly Val Gly Val Pro Gly Gly Val Pro Gly Ala Gly Val Pro Gly
                580                 585                 590

Val Gly Val Pro Gly Val Gly Val Pro Gly Gly Val Pro Gly Gly
                595                 600                 605

Gly Val Pro Gly Ala Gly Val Pro Gly Gly Val Pro Gly Val Gly
                610                 615                 620

Val Pro Gly Val Gly Val Pro Gly Gly Val Pro Gly Ala Gly Val
625                 630                 635                 640

Pro Gly Val Gly Val Pro Gly Gly Val Pro Gly Val Gly Val Pro
                645                 650                 655

Gly Gly Gly Val Pro Gly Ala Gly Val Pro Gly Gly Val Pro Gly
                660                 665                 670

Val Gly Val Pro Gly Val Gly Val Pro Gly Gly Val Pro Gly Ala
                675                 680                 685

Gly Val Pro Gly Val Gly Val Pro Gly Val Gly Val Pro Gly Val Gly
                690                 695                 700

Val Pro Gly Gly Gly Val Pro Gly Ala Gly Val Pro Gly Gly Val
705                 710                 715                 720

Pro Gly Val Gly Val Pro Gly Val Gly Val Pro Gly Gly Gly Val Pro
                725                 730                 735

Gly Ala Gly Val Pro Gly Val Gly Val Pro Gly Val Gly Val Pro Gly
                740                 745                 750

Val Gly Val Pro Gly Gly Gly Val Pro Gly Ala Gly Val Pro Gly Gly
            755                 760                 765

Gly Val Pro Gly Trp Pro
    770

<210> SEQ ID NO 26
<211> LENGTH: 824
<212> TYPE: PRT
<213> ORGANISM: Artificial Sequence
<220> FEATURE:
<223> OTHER INFORMATION: Antp-ELP2

<400> SEQUENCE: 26

Met Arg Gln Ile Lys Ile Trp Phe Gln Asn Arg Arg Met Lys Trp Lys
1               5                   10                  15

Lys Gly Cys Gly Pro Gly Val Gly Val Pro Gly Ala Gly Val Pro Gly
                20                  25                  30

Gly Gly Val Pro Gly Ala Gly Val Pro Gly Gly Val Pro Gly Ala
            35                  40                  45

Gly Val Pro Gly Gly Val Pro Gly Ala Gly Val Pro Gly Gly Gly
            50                  55                  60

Val Pro Gly Ala Gly Val Pro Gly Gly Val Pro Gly Ala Gly Val
65                  70                  75                  80

Pro Gly Gly Gly Val Pro Gly Ala Gly Val Pro Gly Gly Gly Val Pro
                85                  90                  95

Gly Ala Gly Val Pro Gly Val Gly Val Pro Gly Ala Gly Val Pro Gly
                100                 105                 110

```
Gly Gly Val Pro Gly Ala Gly Val Pro Gly Gly Val Pro Gly Ala
            115                 120                 125
Gly Val Pro Gly Gly Val Pro Gly Ala Gly Val Pro Gly Gly Gly
        130                 135                 140
Val Pro Gly Ala Gly Val Pro Gly Gly Val Pro Gly Ala Gly Val
145                 150                 155                 160
Pro Gly Gly Gly Val Pro Gly Ala Gly Val Pro Gly Gly Val Pro
                165                 170                 175
Gly Ala Gly Val Pro Gly Val Gly Val Pro Gly Ala Gly Val Pro Gly
            180                 185                 190
Gly Gly Val Pro Gly Ala Gly Val Pro Gly Gly Val Pro Gly Ala
        195                 200                 205
Gly Val Pro Gly Gly Val Pro Gly Ala Gly Val Pro Gly Gly Gly
        210                 215                 220
Val Pro Gly Ala Gly Val Pro Gly Gly Val Pro Gly Ala Gly Val
225                 230                 235                 240
Pro Gly Gly Gly Val Pro Gly Ala Gly Val Pro Gly Gly Val Pro
                245                 250                 255
Gly Ala Gly Val Pro Gly Val Gly Val Pro Gly Ala Gly Val Pro Gly
            260                 265                 270
Gly Gly Val Pro Gly Ala Gly Val Pro Gly Gly Val Pro Gly Ala
        275                 280                 285
Gly Val Pro Gly Gly Val Pro Gly Ala Gly Val Pro Gly Gly Gly
        290                 295                 300
Val Pro Gly Ala Gly Val Pro Gly Gly Val Pro Gly Ala Gly Val
305                 310                 315                 320
Pro Gly Gly Gly Val Pro Gly Ala Gly Val Pro Gly Gly Val Pro
                325                 330                 335
Gly Ala Gly Val Pro Gly Val Gly Val Pro Gly Ala Gly Val Pro Gly
            340                 345                 350
Gly Gly Val Pro Gly Ala Gly Val Pro Gly Gly Val Pro Gly Ala
        355                 360                 365
Gly Val Pro Gly Gly Val Pro Gly Ala Gly Val Pro Gly Gly Gly
        370                 375                 380
Val Pro Gly Ala Gly Val Pro Gly Gly Val Pro Gly Ala Gly Val
385                 390                 395                 400
Pro Gly Gly Gly Val Pro Gly Ala Gly Val Pro Gly Gly Val Pro
                405                 410                 415
Gly Ala Gly Val Pro Gly Val Gly Val Pro Gly Ala Gly Val Pro Gly
            420                 425                 430
Gly Gly Val Pro Gly Ala Gly Val Pro Gly Gly Val Pro Gly Ala
        435                 440                 445
Gly Val Pro Gly Gly Val Pro Gly Ala Gly Val Pro Gly Gly Gly
        450                 455                 460
Val Pro Gly Ala Gly Val Pro Gly Gly Val Pro Gly Ala Gly Val
465                 470                 475                 480
Pro Gly Gly Gly Val Pro Gly Ala Gly Val Pro Gly Gly Val Pro
                485                 490                 495
Gly Ala Gly Val Pro Gly Val Gly Val Pro Gly Ala Gly Val Pro Gly
            500                 505                 510
Gly Gly Val Pro Gly Ala Gly Val Pro Gly Gly Val Pro Gly Ala
        515                 520                 525
```

```
Gly Val Pro Gly Gly Gly Val Pro Gly Ala Gly Val Pro Gly Gly Gly
        530                 535                 540
Val Pro Gly Ala Gly Val Pro Gly Gly Gly Val Pro Gly Ala Gly Val
545                 550                 555                 560
Pro Gly Gly Gly Val Pro Gly Ala Gly Val Pro Gly Gly Gly Val Pro
                565                 570                 575
Gly Ala Gly Val Pro Gly Val Gly Val Pro Gly Ala Gly Val Pro Gly
            580                 585                 590
Gly Gly Val Pro Gly Ala Gly Val Pro Gly Gly Gly Val Pro Gly Ala
        595                 600                 605
Gly Val Pro Gly Gly Gly Val Pro Gly Ala Gly Val Pro Gly Gly Gly
    610                 615                 620
Val Pro Gly Ala Gly Val Pro Gly Gly Gly Val Pro Gly Ala Gly Val
625                 630                 635                 640
Pro Gly Gly Gly Val Pro Gly Ala Gly Val Pro Gly Gly Gly Val Pro
                645                 650                 655
Gly Ala Gly Val Pro Gly Val Gly Val Pro Gly Ala Gly Val Pro Gly
            660                 665                 670
Gly Gly Val Pro Gly Ala Gly Val Pro Gly Gly Gly Val Pro Gly Ala
        675                 680                 685
Gly Val Pro Gly Gly Gly Val Pro Gly Ala Gly Val Pro Gly Gly Gly
    690                 695                 700
Val Pro Gly Ala Gly Val Pro Gly Gly Gly Val Pro Gly Ala Gly Val
705                 710                 715                 720
Pro Gly Gly Gly Val Pro Gly Ala Gly Val Pro Gly Gly Gly Val Pro
                725                 730                 735
Gly Ala Gly Val Pro Gly Val Gly Val Pro Gly Ala Gly Val Pro Gly
            740                 745                 750
Gly Gly Val Pro Gly Ala Gly Val Pro Gly Gly Gly Val Pro Gly Ala
        755                 760                 765
Gly Val Pro Gly Gly Gly Val Pro Gly Ala Gly Val Pro Gly Gly Gly
    770                 775                 780
Val Pro Gly Ala Gly Val Pro Gly Gly Gly Val Pro Gly Ala Gly Val
785                 790                 795                 800
Pro Gly Gly Gly Val Pro Gly Ala Gly Val Pro Gly Gly Gly Val Pro
                805                 810                 815
Gly Ala Gly Val Pro Gly Trp Pro
            820

<210> SEQ ID NO 27
<211> LENGTH: 778
<212> TYPE: PRT
<213> ORGANISM: Artificial Sequence
<220> FEATURE:
<223> OTHER INFORMATION: MTS-ELP1

<400> SEQUENCE: 27

Met Ala Ala Val Ala Leu Leu Pro Ala Val Leu Leu Ala Leu Leu Ala
1               5                   10                  15
Pro Gly Gly Pro Gly Val Gly Val Pro Gly Val Gly Val Pro Gly Gly
            20                  25                  30
Gly Val Pro Gly Ala Gly Val Pro Gly Val Gly Val Pro Gly Val Gly
        35                  40                  45
Val Pro Gly Val Gly Val Pro Gly Gly Gly Val Pro Gly Ala Gly Val
    50                  55                  60
```

-continued

```
Pro Gly Gly Gly Val Pro Gly Val Gly Val Pro Gly Val Pro
65                  70                  75                  80

Gly Gly Gly Val Pro Gly Ala Gly Val Pro Gly Val Gly Val Pro Gly
                85                  90                  95

Val Gly Val Pro Gly Val Gly Val Pro Gly Gly Gly Val Pro Gly Ala
            100                 105                 110

Gly Val Pro Gly Gly Val Pro Gly Val Gly Val Pro Gly Val Gly
        115                 120                 125

Val Pro Gly Gly Val Pro Gly Ala Gly Val Pro Gly Val Gly Val
    130                 135                 140

Pro Gly Val Gly Val Pro Gly Val Gly Val Pro Gly Gly Gly Val Pro
145                 150                 155                 160

Gly Ala Gly Val Pro Gly Gly Val Pro Gly Val Gly Val Pro Gly
        165                 170                 175

Val Gly Val Pro Gly Gly Val Pro Gly Ala Gly Val Pro Gly Val
            180                 185                 190

Gly Val Pro Gly Val Gly Val Pro Gly Val Gly Val Pro Gly Gly Gly
        195                 200                 205

Val Pro Gly Ala Gly Val Pro Gly Gly Val Pro Gly Val Gly Val
    210                 215                 220

Pro Gly Val Gly Val Pro Gly Gly Val Pro Gly Ala Gly Val Pro
225                 230                 235                 240

Gly Val Gly Val Pro Gly Val Gly Val Pro Gly Val Gly Val Pro Gly
                245                 250                 255

Gly Gly Val Pro Gly Ala Gly Val Pro Gly Gly Val Pro Gly Val
            260                 265                 270

Gly Val Pro Gly Val Gly Val Pro Gly Gly Val Pro Gly Ala Gly
        275                 280                 285

Val Pro Gly Val Gly Val Pro Gly Val Gly Val Pro Gly Val Gly Val
    290                 295                 300

Pro Gly Gly Gly Val Pro Gly Ala Gly Val Pro Gly Gly Gly Val Pro
305                 310                 315                 320

Gly Val Gly Val Pro Gly Val Gly Val Pro Gly Gly Gly Val Pro Gly
                325                 330                 335

Ala Gly Val Pro Gly Val Gly Val Pro Gly Val Gly Val Pro Gly Val
            340                 345                 350

Gly Val Pro Gly Gly Gly Val Pro Gly Ala Gly Val Pro Gly Gly Gly
        355                 360                 365

Val Pro Gly Val Gly Val Pro Gly Val Gly Val Pro Gly Gly Gly Val
    370                 375                 380

Pro Gly Ala Gly Val Pro Gly Val Gly Val Pro Gly Val Gly Val Pro
385                 390                 395                 400

Gly Val Gly Val Pro Gly Gly Gly Val Pro Gly Ala Gly Val Pro Gly
                405                 410                 415

Gly Gly Val Pro Gly Val Gly Val Pro Gly Val Gly Val Pro Gly Gly
            420                 425                 430

Gly Val Pro Gly Ala Gly Val Pro Gly Val Gly Val Pro Gly Val Gly
        435                 440                 445

Val Pro Gly Val Gly Val Pro Gly Gly Gly Val Pro Gly Ala Gly Val
    450                 455                 460

Pro Gly Gly Gly Val Pro Gly Val Gly Val Pro Gly Val Gly Val Pro
465                 470                 475                 480

Gly Gly Gly Val Pro Gly Ala Gly Val Pro Gly Val Gly Val Pro Gly
```

```
                    485                 490                 495
Val Gly Val Pro Gly Val Gly Val Pro Gly Gly Val Pro Gly Ala
                500                 505                 510

Gly Val Pro Gly Gly Gly Val Pro Gly Val Gly Val Pro Gly Val Gly
            515                 520                 525

Val Pro Gly Gly Gly Val Pro Gly Ala Gly Val Pro Gly Val Gly Val
        530                 535                 540

Pro Gly Val Gly Val Pro Gly Val Gly Val Pro Gly Gly Gly Val Pro
545                 550                 555                 560

Gly Ala Gly Val Pro Gly Gly Gly Val Pro Gly Val Gly Val Pro Gly
            565                 570                 575

Val Gly Val Pro Gly Gly Gly Val Pro Gly Ala Gly Val Pro Gly Val
        580                 585                 590

Gly Val Pro Gly Val Gly Val Pro Gly Val Gly Val Pro Gly Gly Gly
    595                 600                 605

Val Pro Gly Ala Gly Val Pro Gly Gly Gly Val Pro Gly Val Gly Val
610                 615                 620

Pro Gly Val Gly Val Pro Gly Gly Gly Val Pro Gly Ala Gly Val Pro
625                 630                 635                 640

Gly Val Gly Val Pro Gly Val Gly Val Pro Gly Val Gly Val Pro Gly
            645                 650                 655

Gly Gly Val Pro Gly Ala Gly Val Pro Gly Gly Gly Val Pro Gly Val
        660                 665                 670

Gly Val Pro Gly Val Gly Val Pro Gly Gly Gly Val Pro Gly Ala Gly
    675                 680                 685

Val Pro Gly Val Gly Val Pro Gly Val Gly Val Pro Gly Val Gly Val
690                 695                 700

Pro Gly Gly Gly Val Pro Gly Ala Gly Val Pro Gly Gly Gly Val Pro
705                 710                 715                 720

Gly Val Gly Val Pro Gly Val Gly Val Pro Gly Gly Gly Val Pro Gly
            725                 730                 735

Ala Gly Val Pro Gly Val Gly Val Pro Gly Val Gly Val Pro Gly Val
        740                 745                 750

Gly Val Pro Gly Gly Gly Val Pro Gly Ala Gly Val Pro Gly Gly Gly
    755                 760                 765

Val Pro Gly Trp Pro Gly Ser Gly Gly Cys
    770                 775

<210> SEQ ID NO 28
<211> LENGTH: 828
<212> TYPE: PRT
<213> ORGANISM: Artificial Sequence
<220> FEATURE:
<223> OTHER INFORMATION: MTS-ELP2

<400> SEQUENCE: 28

Met Ala Ala Val Ala Leu Leu Pro Ala Val Leu Leu Ala Leu Leu Ala
1               5                   10                  15

Pro Gly Gly Pro Gly Val Gly Val Pro Gly Ala Gly Val Pro Gly Gly
            20                  25                  30

Gly Val Pro Gly Ala Gly Val Pro Gly Gly Gly Val Pro Gly Ala Gly
        35                  40                  45

Val Pro Gly Gly Gly Val Pro Gly Ala Gly Val Pro Gly Gly Gly Val
    50                  55                  60

Pro Gly Ala Gly Val Pro Gly Gly Gly Val Pro Gly Ala Gly Val Pro
```

-continued

```
                65                  70                  75                  80
Gly Gly Gly Val Pro Gly Ala Gly Val Pro Gly Gly Gly Val Pro Gly
                    85                  90                  95
Ala Gly Val Pro Gly Val Gly Val Pro Gly Ala Gly Val Pro Gly Gly
                    100                 105                 110
Gly Val Pro Gly Ala Gly Val Pro Gly Gly Gly Val Pro Gly Ala Gly
                    115                 120                 125
Val Pro Gly Gly Val Pro Gly Ala Gly Val Pro Gly Gly Gly Val
                    130                 135                 140
Pro Gly Ala Gly Val Pro Gly Gly Gly Val Pro Gly Ala Gly Val Pro
145                 150                 155                 160
Gly Gly Gly Val Pro Gly Ala Gly Val Pro Gly Gly Gly Val Pro Gly
                    165                 170                 175
Ala Gly Val Pro Gly Val Gly Val Pro Gly Ala Gly Val Pro Gly Gly
                    180                 185                 190
Gly Val Pro Gly Ala Gly Val Pro Gly Gly Gly Val Pro Gly Ala Gly
                    195                 200                 205
Val Pro Gly Gly Gly Val Pro Gly Ala Gly Val Pro Gly Gly Gly Val
                    210                 215                 220
Pro Gly Ala Gly Val Pro Gly Gly Gly Val Pro Gly Ala Gly Val Pro
225                 230                 235                 240
Gly Gly Gly Val Pro Gly Ala Gly Val Pro Gly Gly Gly Val Pro Gly
                    245                 250                 255
Ala Gly Val Pro Gly Val Gly Val Pro Gly Ala Gly Val Pro Gly Gly
                    260                 265                 270
Gly Val Pro Gly Ala Gly Val Pro Gly Gly Gly Val Pro Gly Ala Gly
                    275                 280                 285
Val Pro Gly Gly Gly Val Pro Gly Ala Gly Val Pro Gly Gly Gly Val
                    290                 295                 300
Pro Gly Ala Gly Val Pro Gly Gly Gly Val Pro Gly Ala Gly Val Pro
305                 310                 315                 320
Gly Gly Gly Val Pro Gly Ala Gly Val Pro Gly Gly Gly Val Pro Gly
                    325                 330                 335
Ala Gly Val Pro Gly Val Gly Val Pro Gly Ala Gly Val Pro Gly Gly
                    340                 345                 350
Gly Val Pro Gly Ala Gly Val Pro Gly Gly Gly Val Pro Gly Ala Gly
                    355                 360                 365
Val Pro Gly Gly Gly Val Pro Gly Ala Gly Val Pro Gly Gly Gly Val
                    370                 375                 380
Pro Gly Ala Gly Val Pro Gly Gly Gly Val Pro Gly Ala Gly Val Pro
385                 390                 395                 400
Gly Gly Gly Val Pro Gly Ala Gly Val Pro Gly Gly Gly Val Pro Gly
                    405                 410                 415
Ala Gly Val Pro Gly Val Gly Val Pro Gly Ala Gly Val Pro Gly Gly
                    420                 425                 430
Gly Val Pro Gly Ala Gly Val Pro Gly Gly Gly Val Pro Gly Ala Gly
                    435                 440                 445
Val Pro Gly Gly Gly Val Pro Gly Ala Gly Val Pro Gly Gly Gly Val
                    450                 455                 460
Pro Gly Ala Gly Val Pro Gly Gly Gly Val Pro Gly Ala Gly Val Pro
465                 470                 475                 480
Gly Gly Gly Val Pro Gly Ala Gly Val Pro Gly Gly Gly Val Pro Gly
                    485                 490                 495
```

-continued

```
Ala Gly Val Pro Gly Val Gly Val Pro Gly Ala Gly Val Pro Gly Gly
            500                 505                 510
Gly Val Pro Gly Ala Gly Val Pro Gly Gly Gly Val Pro Gly Ala Gly
            515                 520                 525
Val Pro Gly Gly Gly Val Pro Gly Ala Gly Val Pro Gly Gly Gly Val
            530                 535                 540
Pro Gly Ala Gly Val Pro Gly Gly Gly Val Pro Gly Ala Gly Val Pro
545                 550                 555                 560
Gly Gly Gly Val Pro Gly Ala Gly Val Pro Gly Gly Gly Val Pro Gly
                565                 570                 575
Ala Gly Val Pro Gly Val Gly Val Pro Gly Ala Gly Val Pro Gly Gly
            580                 585                 590
Gly Val Pro Gly Ala Gly Val Pro Gly Gly Gly Val Pro Gly Ala Gly
            595                 600                 605
Val Pro Gly Gly Gly Val Pro Gly Ala Gly Val Pro Gly Gly Gly Val
            610                 615                 620
Pro Gly Ala Gly Val Pro Gly Gly Gly Val Pro Gly Ala Gly Val Pro
625                 630                 635                 640
Gly Gly Gly Val Pro Gly Ala Gly Val Pro Gly Gly Gly Val Pro Gly
                645                 650                 655
Ala Gly Val Pro Gly Val Gly Val Pro Gly Ala Gly Val Pro Gly Gly
            660                 665                 670
Gly Val Pro Gly Ala Gly Val Pro Gly Gly Gly Val Pro Gly Ala Gly
            675                 680                 685
Val Pro Gly Gly Gly Val Pro Gly Ala Gly Val Pro Gly Gly Gly Val
            690                 695                 700
Pro Gly Ala Gly Val Pro Gly Gly Gly Val Pro Gly Ala Gly Val Pro
705                 710                 715                 720
Gly Gly Gly Val Pro Gly Ala Gly Val Pro Gly Gly Gly Val Pro Gly
                725                 730                 735
Ala Gly Val Pro Gly Val Gly Val Pro Gly Ala Gly Val Pro Gly Gly
            740                 745                 750
Gly Val Pro Gly Ala Gly Val Pro Gly Gly Gly Val Pro Gly Ala Gly
            755                 760                 765
Val Pro Gly Gly Gly Val Pro Gly Ala Gly Val Pro Gly Gly Gly Val
            770                 775                 780
Pro Gly Ala Gly Val Pro Gly Gly Gly Val Pro Gly Ala Gly Val Pro
785                 790                 795                 800
Gly Gly Gly Val Pro Gly Ala Gly Val Pro Gly Gly Gly Val Pro Gly
                805                 810                 815
Ala Gly Val Pro Gly Trp Pro Gly Ser Gly Gly Cys
            820                 825

<210> SEQ ID NO 29
<211> LENGTH: 786
<212> TYPE: PRT
<213> ORGANISM: Artificial Sequence
<220> FEATURE:
<223> OTHER INFORMATION: Bac-7-ELP1

<400> SEQUENCE: 29

Met Arg Arg Ile Arg Pro Arg Pro Pro Arg Leu Pro Arg Pro Arg Pro
1               5                   10                  15
Arg Pro Leu Pro Phe Pro Arg Pro Gly Gly Gly Pro Gly Val Gly Val
            20                  25                  30
```

Pro Gly Val Gly Val Pro Gly Gly Val Pro Gly Ala Gly Val Pro
            35                  40                  45
Gly Val Gly Val Pro Gly Val Gly Val Pro Gly Val Gly Val Pro Gly
 50                  55                  60
Gly Gly Val Pro Gly Ala Gly Val Pro Gly Gly Val Pro Gly Val
 65                  70                  75                  80
Gly Val Pro Gly Val Gly Val Pro Gly Gly Val Pro Gly Ala Gly
                 85                  90                  95
Val Pro Gly Val Gly Val Pro Gly Val Gly Val Pro Gly Val Gly Val
            100                 105                 110
Pro Gly Gly Gly Val Pro Gly Ala Gly Val Pro Gly Gly Val Pro
            115                 120                 125
Gly Val Gly Val Pro Gly Val Gly Val Pro Gly Gly Gly Val Pro Gly
            130                 135                 140
Ala Gly Val Pro Gly Val Gly Val Pro Gly Val Gly Val Pro Gly Val
145                 150                 155                 160
Gly Val Pro Gly Gly Gly Val Pro Gly Ala Gly Val Pro Gly Gly Gly
                165                 170                 175
Val Pro Gly Val Gly Val Pro Gly Val Gly Val Pro Gly Gly Gly Val
            180                 185                 190
Pro Gly Ala Gly Val Pro Gly Val Gly Val Pro Gly Val Gly Val Pro
            195                 200                 205
Gly Val Gly Val Pro Gly Gly Gly Val Pro Gly Ala Gly Val Pro Gly
            210                 215                 220
Gly Gly Val Pro Gly Val Gly Val Pro Gly Val Gly Val Pro Gly Gly
225                 230                 235                 240
Gly Val Pro Gly Ala Gly Val Pro Gly Val Gly Val Pro Gly Val Gly
                245                 250                 255
Val Pro Gly Val Gly Val Pro Gly Gly Gly Val Pro Gly Ala Gly Val
            260                 265                 270
Pro Gly Gly Gly Val Pro Gly Val Gly Val Pro Gly Val Gly Val Pro
            275                 280                 285
Gly Gly Gly Val Pro Gly Ala Gly Val Pro Gly Val Gly Val Pro Gly
            290                 295                 300
Val Gly Val Pro Gly Val Gly Val Pro Gly Gly Gly Val Pro Gly Ala
305                 310                 315                 320
Gly Val Pro Gly Gly Gly Val Pro Gly Val Gly Val Pro Gly Val Gly
                325                 330                 335
Val Pro Gly Gly Gly Val Pro Gly Ala Gly Val Pro Gly Gly Gly Val
            340                 345                 350
Pro Gly Val Gly Val Pro Gly Val Gly Val Pro Gly Gly Gly Val Pro
            355                 360                 365
Gly Ala Gly Val Pro Gly Gly Gly Val Pro Gly Val Gly Val Pro Gly
            370                 375                 380
Val Gly Val Pro Gly Gly Gly Val Pro Gly Ala Gly Val Pro Gly Val
385                 390                 395                 400
Gly Val Pro Gly Val Gly Val Pro Gly Val Gly Val Pro Gly Gly Gly
                405                 410                 415
Val Pro Gly Ala Gly Val Pro Gly Gly Gly Val Pro Gly Val Gly Val
            420                 425                 430
Pro Gly Val Gly Val Pro Gly Gly Gly Val Pro Gly Ala Gly Val Pro
            435                 440                 445

```
Gly Val Gly Val Pro Gly Val Gly Val Pro Gly Val Gly Val Pro Gly
    450                 455                 460
Gly Gly Val Pro Gly Ala Gly Val Pro Gly Gly Val Pro Gly Val
465                 470                 475                 480
Gly Val Pro Gly Val Gly Val Pro Gly Gly Val Pro Gly Ala Gly
                485                 490                 495
Val Pro Gly Val Gly Val Pro Gly Val Gly Val Pro Gly Val Gly Val
            500                 505                 510
Pro Gly Gly Gly Val Pro Gly Ala Gly Val Pro Gly Gly Val Pro
        515                 520                 525
Gly Val Gly Val Pro Gly Val Gly Val Pro Gly Gly Val Pro Gly
    530                 535                 540
Ala Gly Val Pro Gly Val Gly Val Pro Gly Val Gly Val Pro Gly Val
545                 550                 555                 560
Gly Val Pro Gly Gly Gly Val Pro Gly Ala Gly Val Pro Gly Gly
                565                 570                 575
Val Pro Gly Val Gly Val Pro Gly Val Gly Val Pro Gly Gly Val
            580                 585                 590
Pro Gly Ala Gly Val Pro Gly Val Gly Val Pro Gly Val Gly Val Pro
        595                 600                 605
Gly Val Gly Val Pro Gly Gly Gly Val Pro Gly Ala Gly Val Pro Gly
    610                 615                 620
Gly Gly Val Pro Gly Val Gly Val Pro Gly Val Gly Val Pro Gly Gly
625                 630                 635                 640
Gly Val Pro Gly Ala Gly Val Pro Gly Val Gly Val Pro Gly Val Gly
                645                 650                 655
Val Pro Gly Val Gly Val Pro Gly Gly Gly Val Pro Gly Ala Gly Val
            660                 665                 670
Pro Gly Gly Gly Val Pro Gly Val Gly Val Pro Gly Val Gly Val Pro
        675                 680                 685
Gly Gly Gly Val Pro Gly Ala Gly Val Pro Gly Val Gly Val Pro Gly
    690                 695                 700
Val Gly Val Pro Gly Val Gly Val Pro Gly Gly Gly Val Pro Gly Ala
705                 710                 715                 720
Gly Val Pro Gly Gly Gly Val Pro Gly Val Gly Val Pro Gly Val Gly
                725                 730                 735
Val Pro Gly Gly Gly Val Pro Gly Ala Gly Val Pro Gly Val Gly Val
            740                 745                 750
Pro Gly Val Gly Val Pro Gly Val Gly Val Pro Gly Gly Gly Val Pro
        755                 760                 765
Gly Ala Gly Val Pro Gly Gly Val Pro Gly Trp Pro Gly Ser Gly
    770                 775                 780
Gly Cys
785
```

<210> SEQ ID NO 30
<211> LENGTH: 836
<212> TYPE: PRT
<213> ORGANISM: Artificial Sequence
<220> FEATURE:
<223> OTHER INFORMATION: Bac-7-ELP2

<400> SEQUENCE: 30

```
Met Arg Arg Ile Arg Pro Arg Pro Pro Arg Leu Pro Arg Pro Arg Pro
1               5                   10                  15
```

-continued

Arg Pro Leu Pro Phe Pro Arg Pro Gly Gly Pro Gly Val Gly Val
            20                  25                  30

Pro Gly Ala Gly Val Pro Gly Gly Val Pro Gly Ala Gly Val Pro
            35                  40                  45

Gly Gly Gly Val Pro Gly Ala Gly Val Pro Gly Gly Gly Val Pro Gly
        50                  55                  60

Ala Gly Val Pro Gly Gly Val Pro Gly Ala Gly Val Pro Gly Gly
65                  70                  75                  80

Gly Val Pro Gly Ala Gly Val Pro Gly Gly Val Pro Gly Ala Gly
                85                  90                  95

Val Pro Gly Gly Gly Val Pro Gly Ala Gly Val Pro Gly Val Gly Val
            100                 105                 110

Pro Gly Ala Gly Val Pro Gly Gly Val Pro Gly Ala Gly Val Pro
            115                 120                 125

Gly Gly Gly Val Pro Gly Ala Gly Val Pro Gly Gly Gly Val Pro Gly
        130                 135                 140

Ala Gly Val Pro Gly Gly Val Pro Gly Ala Gly Val Pro Gly Gly
145                 150                 155                 160

Gly Val Pro Gly Ala Gly Val Pro Gly Gly Val Pro Gly Ala Gly
                165                 170                 175

Val Pro Gly Gly Gly Val Pro Gly Ala Gly Val Pro Gly Val Gly Val
            180                 185                 190

Pro Gly Ala Gly Val Pro Gly Gly Val Pro Gly Ala Gly Val Pro
            195                 200                 205

Gly Gly Gly Val Pro Gly Ala Gly Val Pro Gly Gly Gly Val Pro Gly
        210                 215                 220

Ala Gly Val Pro Gly Gly Val Pro Gly Ala Gly Val Pro Gly Gly
225                 230                 235                 240

Gly Val Pro Gly Ala Gly Val Pro Gly Gly Val Pro Gly Ala Gly
                245                 250                 255

Val Pro Gly Gly Gly Val Pro Gly Ala Gly Val Pro Gly Val Gly Val
            260                 265                 270

Pro Gly Ala Gly Val Pro Gly Gly Val Pro Gly Ala Gly Val Pro
            275                 280                 285

Gly Gly Gly Val Pro Gly Ala Gly Val Pro Gly Gly Gly Val Pro Gly
        290                 295                 300

Ala Gly Val Pro Gly Gly Val Pro Gly Ala Gly Val Pro Gly Gly
305                 310                 315                 320

Gly Val Pro Gly Ala Gly Val Pro Gly Gly Val Pro Gly Ala Gly
                325                 330                 335

Val Pro Gly Gly Gly Val Pro Gly Ala Gly Val Pro Gly Val Gly Val
            340                 345                 350

Pro Gly Ala Gly Val Pro Gly Gly Val Pro Gly Ala Gly Val Pro
            355                 360                 365

Gly Gly Gly Val Pro Gly Ala Gly Val Pro Gly Gly Gly Val Pro Gly
        370                 375                 380

Ala Gly Val Pro Gly Gly Val Pro Gly Ala Gly Val Pro Gly Gly
385                 390                 395                 400

Gly Val Pro Gly Ala Gly Val Pro Gly Gly Val Pro Gly Ala Gly
                405                 410                 415

Val Pro Gly Gly Gly Val Pro Gly Ala Gly Val Pro Gly Val Gly Val
            420                 425                 430

Pro Gly Ala Gly Val Pro Gly Gly Gly Val Pro Gly Ala Gly Val Pro

-continued

```
                435                 440                 445
Gly Gly Gly Val Pro Gly Ala Gly Val Pro Gly Gly Val Pro Gly
        450                 455                 460
Ala Gly Val Pro Gly Gly Gly Val Pro Gly Ala Gly Val Pro Gly Gly
465                 470                 475                 480
Gly Val Pro Gly Ala Gly Val Pro Gly Gly Val Pro Gly Ala Gly
                485                 490                 495
Val Pro Gly Gly Gly Val Pro Gly Ala Gly Val Pro Gly Val Gly Val
                500                 505                 510
Pro Gly Ala Gly Val Pro Gly Gly Val Pro Gly Ala Gly Val Pro
        515                 520                 525
Gly Gly Gly Val Pro Gly Ala Gly Val Pro Gly Gly Gly Val Pro Gly
        530                 535                 540
Ala Gly Val Pro Gly Gly Gly Val Pro Gly Ala Gly Val Pro Gly Gly
545                 550                 555                 560
Gly Val Pro Gly Ala Gly Val Pro Gly Gly Val Pro Gly Ala Gly
                565                 570                 575
Val Pro Gly Gly Gly Val Pro Gly Ala Gly Val Pro Gly Val Gly Val
                580                 585                 590
Pro Gly Ala Gly Val Pro Gly Gly Gly Val Pro Gly Ala Gly Val Pro
        595                 600                 605
Gly Gly Gly Val Pro Gly Ala Gly Val Pro Gly Gly Gly Val Pro Gly
        610                 615                 620
Ala Gly Val Pro Gly Gly Gly Val Pro Gly Ala Gly Val Pro Gly Gly
625                 630                 635                 640
Gly Val Pro Gly Ala Gly Val Pro Gly Gly Val Pro Gly Ala Gly
                645                 650                 655
Val Pro Gly Gly Gly Val Pro Gly Ala Gly Val Pro Gly Val Gly Val
                660                 665                 670
Pro Gly Ala Gly Val Pro Gly Gly Gly Val Pro Gly Ala Gly Val Pro
        675                 680                 685
Gly Gly Gly Val Pro Gly Ala Gly Val Pro Gly Gly Gly Val Pro Gly
        690                 695                 700
Ala Gly Val Pro Gly Gly Gly Val Pro Gly Ala Gly Val Pro Gly Gly
705                 710                 715                 720
Gly Val Pro Gly Ala Gly Val Pro Gly Gly Val Pro Gly Ala Gly
                725                 730                 735
Val Pro Gly Gly Gly Val Pro Gly Ala Gly Val Pro Gly Val Gly Val
                740                 745                 750
Pro Gly Ala Gly Val Pro Gly Gly Gly Val Pro Gly Ala Gly Val Pro
        755                 760                 765
Gly Gly Gly Val Pro Gly Ala Gly Val Pro Gly Gly Gly Val Pro Gly
        770                 775                 780
Ala Gly Val Pro Gly Gly Gly Val Pro Gly Ala Gly Val Pro Gly Gly
785                 790                 795                 800
Gly Val Pro Gly Ala Gly Val Pro Gly Gly Val Pro Gly Ala Gly
                805                 810                 815
Val Pro Gly Gly Gly Val Pro Gly Ala Gly Val Pro Gly Trp Pro Gly
                820                 825                 830
Ser Gly Gly Cys
        835
```

<210> SEQ ID NO 31

<211> LENGTH: 789
<212> TYPE: PRT
<213> ORGANISM: Artificial Sequence
<220> FEATURE:
<223> OTHER INFORMATION: Trans-ELP1

<400> SEQUENCE: 31

```
Met Gly Trp Thr Leu Asn Ser Ala Gly Tyr Leu Leu Gly Lys Ile Asn
1               5                   10                  15
Leu Lys Ala Leu Ala Ala Leu Ala Lys Lys Ile Leu Gly Gly Pro Gly
            20                  25                  30
Val Gly Val Pro Gly Val Gly Val Pro Gly Gly Gly Val Pro Gly Ala
        35                  40                  45
Gly Val Pro Gly Val Gly Val Pro Gly Val Gly Val Pro Gly Val Gly
    50                  55                  60
Val Pro Gly Gly Gly Val Pro Gly Ala Gly Val Pro Gly Gly Gly Val
65                  70                  75                  80
Pro Gly Val Gly Val Pro Gly Val Gly Val Pro Gly Gly Gly Val Pro
                85                  90                  95
Gly Ala Gly Val Pro Gly Val Gly Val Pro Gly Val Gly Val Pro Gly
            100                 105                 110
Val Gly Val Pro Gly Gly Gly Val Pro Gly Ala Gly Val Pro Gly Gly
        115                 120                 125
Gly Val Pro Gly Val Gly Val Pro Gly Val Gly Val Pro Gly Gly Gly
    130                 135                 140
Val Pro Gly Ala Gly Val Pro Gly Val Gly Val Pro Gly Val Gly Val
145                 150                 155                 160
Pro Gly Val Gly Val Pro Gly Gly Gly Val Pro Gly Ala Gly Val Pro
                165                 170                 175
Gly Gly Gly Val Pro Gly Val Gly Val Pro Gly Val Gly Val Pro Gly
            180                 185                 190
Gly Gly Val Pro Gly Ala Gly Val Pro Gly Val Gly Val Pro Gly Val
        195                 200                 205
Gly Val Pro Gly Val Gly Val Pro Gly Gly Gly Val Pro Gly Ala Gly
    210                 215                 220
Val Pro Gly Gly Gly Val Pro Gly Val Gly Val Pro Gly Val Gly Val
225                 230                 235                 240
Pro Gly Gly Gly Val Pro Gly Ala Gly Val Pro Gly Val Gly Val Pro
                245                 250                 255
Gly Val Gly Val Pro Gly Val Gly Val Pro Gly Gly Gly Val Pro Gly
            260                 265                 270
Ala Gly Val Pro Gly Gly Gly Val Pro Gly Val Gly Val Pro Gly Val
        275                 280                 285
Gly Val Pro Gly Gly Gly Val Pro Gly Ala Gly Val Pro Gly Val Gly
    290                 295                 300
Val Pro Gly Val Gly Val Pro Gly Val Gly Val Pro Gly Gly Gly Val
305                 310                 315                 320
Pro Gly Ala Gly Val Pro Gly Gly Gly Val Pro Gly Val Gly Val Pro
                325                 330                 335
Gly Val Gly Val Pro Gly Gly Gly Val Pro Gly Ala Gly Val Pro Gly
            340                 345                 350
Val Gly Val Pro Gly Val Gly Val Pro Gly Val Gly Val Pro Gly Gly
        355                 360                 365
Gly Val Pro Gly Ala Gly Val Pro Gly Gly Gly Val Pro Gly Val Gly
    370                 375                 380
```

Val Pro Gly Val Gly Val Pro Gly Gly Gly Val Pro Gly Ala Gly Val
385                 390                 395                 400

Pro Gly Val Gly Val Pro Gly Val Gly Val Pro Gly Val Gly Val Pro
                405                 410                 415

Gly Gly Gly Val Pro Gly Ala Gly Val Pro Gly Gly Gly Val Pro Gly
            420                 425                 430

Val Gly Val Pro Gly Val Gly Val Pro Gly Gly Gly Val Pro Gly Ala
            435                 440                 445

Gly Val Pro Gly Val Gly Val Pro Gly Val Gly Val Pro Gly Val Gly
        450                 455                 460

Val Pro Gly Gly Gly Pro Gly Ala Gly Val Pro Gly Gly Gly Val
465                 470                 475                 480

Pro Gly Val Gly Val Pro Gly Val Gly Val Pro Gly Gly Gly Val Pro
                485                 490                 495

Gly Ala Gly Val Pro Gly Val Gly Val Pro Gly Val Gly Val Pro Gly
            500                 505                 510

Val Gly Val Pro Gly Gly Gly Val Pro Gly Ala Gly Val Pro Gly Gly
            515                 520                 525

Gly Val Pro Gly Val Gly Val Pro Gly Val Gly Val Pro Gly Gly Gly
        530                 535                 540

Val Pro Gly Ala Gly Val Pro Gly Val Gly Val Pro Gly Val Gly Val
545                 550                 555                 560

Pro Gly Val Gly Val Pro Gly Gly Gly Val Pro Gly Ala Gly Val Pro
                565                 570                 575

Gly Gly Gly Val Pro Gly Val Gly Val Pro Gly Val Gly Val Pro Gly
            580                 585                 590

Gly Gly Val Pro Gly Ala Gly Val Pro Gly Val Gly Val Pro Gly Val
            595                 600                 605

Gly Val Pro Gly Val Gly Val Pro Gly Gly Gly Val Pro Gly Ala Gly
        610                 615                 620

Val Pro Gly Gly Gly Val Pro Gly Val Gly Val Pro Gly Val Gly Val
625                 630                 635                 640

Pro Gly Gly Gly Val Pro Gly Ala Gly Val Pro Gly Val Gly Val Pro
                645                 650                 655

Gly Val Gly Val Pro Gly Val Gly Val Pro Gly Gly Gly Val Pro Gly
            660                 665                 670

Ala Gly Val Pro Gly Gly Gly Val Pro Gly Val Gly Val Pro Gly Val
            675                 680                 685

Gly Val Pro Gly Gly Gly Val Pro Gly Ala Gly Val Pro Gly Val Gly
        690                 695                 700

Val Pro Gly Val Gly Val Pro Gly Val Gly Val Pro Gly Gly Gly Val
705                 710                 715                 720

Pro Gly Ala Gly Val Pro Gly Gly Gly Val Pro Gly Val Gly Val Pro
            725                 730                 735

Gly Val Gly Val Pro Gly Gly Gly Val Pro Gly Ala Gly Val Pro Gly
            740                 745                 750

Val Gly Val Pro Gly Val Gly Val Pro Gly Val Gly Val Pro Gly Gly
            755                 760                 765

Gly Val Pro Gly Ala Gly Val Pro Gly Gly Gly Val Pro Gly Trp Pro
        770                 775                 780

Gly Ser Gly Gly Cys
785

<210> SEQ ID NO 32
<211> LENGTH: 839
<212> TYPE: PRT
<213> ORGANISM: Artificial Sequence
<220> FEATURE:
<223> OTHER INFORMATION: Trans-ELP2

<400> SEQUENCE: 32

```
Met Gly Trp Thr Leu Asn Ser Ala Gly Tyr Leu Leu Gly Lys Ile Asn
1               5                   10                  15

Leu Lys Ala Leu Ala Ala Leu Ala Lys Lys Ile Leu Gly Gly Pro Gly
            20                  25                  30

Val Gly Val Pro Gly Ala Gly Val Pro Gly Gly Val Pro Gly Ala
        35                  40                  45

Gly Val Pro Gly Gly Gly Val Pro Gly Ala Gly Val Pro Gly Gly Gly
        50                  55                  60

Val Pro Gly Ala Gly Val Pro Gly Gly Val Pro Gly Ala Gly Val
65                  70                  75                  80

Pro Gly Gly Gly Val Pro Gly Ala Gly Val Pro Gly Gly Gly Val Pro
                85                  90                  95

Gly Ala Gly Val Pro Gly Gly Gly Val Pro Gly Ala Gly Val Pro Gly
            100                 105                 110

Val Gly Val Pro Gly Ala Gly Val Pro Gly Gly Val Pro Gly Ala
        115                 120                 125

Gly Val Pro Gly Gly Gly Val Pro Gly Ala Gly Val Pro Gly Gly Gly
        130                 135                 140

Val Pro Gly Ala Gly Val Pro Gly Gly Gly Val Pro Gly Ala Gly Val
145                 150                 155                 160

Pro Gly Gly Gly Val Pro Gly Ala Gly Val Pro Gly Gly Gly Val Pro
                165                 170                 175

Gly Ala Gly Val Pro Gly Gly Gly Val Pro Gly Ala Gly Val Pro Gly
            180                 185                 190

Val Gly Val Pro Gly Ala Gly Val Pro Gly Gly Gly Val Pro Gly Ala
        195                 200                 205

Gly Val Pro Gly Gly Gly Val Pro Gly Ala Gly Val Pro Gly Gly Gly
        210                 215                 220

Val Pro Gly Ala Gly Val Pro Gly Gly Gly Val Pro Gly Ala Gly Val
225                 230                 235                 240

Pro Gly Gly Gly Val Pro Gly Ala Gly Val Pro Gly Gly Gly Val Pro
                245                 250                 255

Gly Ala Gly Val Pro Gly Gly Gly Val Pro Gly Ala Gly Val Pro Gly
            260                 265                 270

Val Gly Val Pro Gly Ala Gly Val Pro Gly Gly Gly Val Pro Gly Ala
        275                 280                 285

Gly Val Pro Gly Gly Gly Val Pro Gly Ala Gly Val Pro Gly Gly Gly
        290                 295                 300

Val Pro Gly Ala Gly Val Pro Gly Gly Gly Val Pro Gly Ala Gly Val
305                 310                 315                 320

Pro Gly Gly Gly Val Pro Gly Ala Gly Val Pro Gly Gly Gly Val Pro
                325                 330                 335

Gly Ala Gly Val Pro Gly Gly Gly Val Pro Gly Ala Gly Val Pro Gly
            340                 345                 350

Val Gly Val Pro Gly Ala Gly Val Pro Gly Gly Gly Val Pro Gly Ala
        355                 360                 365
```

```
Gly Val Pro Gly Gly Gly Val Pro Gly Ala Gly Val Pro Gly Gly Gly
    370                 375                 380
Val Pro Gly Ala Gly Val Pro Gly Gly Gly Val Pro Gly Ala Gly Val
385                 390                 395                 400
Pro Gly Gly Gly Val Pro Gly Ala Gly Val Pro Gly Gly Gly Val Pro
                405                 410                 415
Gly Ala Gly Val Pro Gly Gly Gly Val Pro Gly Ala Gly Val Pro Gly
                420                 425                 430
Val Gly Val Pro Gly Ala Gly Val Pro Gly Gly Gly Val Pro Gly Ala
                435                 440                 445
Gly Val Pro Gly Gly Gly Val Pro Gly Ala Gly Val Pro Gly Gly Gly
    450                 455                 460
Val Pro Gly Ala Gly Val Pro Gly Gly Gly Val Pro Gly Ala Gly Val
465                 470                 475                 480
Pro Gly Gly Gly Val Pro Gly Ala Gly Val Pro Gly Gly Gly Val Pro
                485                 490                 495
Gly Ala Gly Val Pro Gly Gly Gly Val Pro Gly Ala Gly Val Pro Gly
                500                 505                 510
Val Gly Val Pro Gly Ala Gly Val Pro Gly Gly Gly Val Pro Gly Ala
                515                 520                 525
Gly Val Pro Gly Gly Gly Val Pro Gly Ala Gly Val Pro Gly Gly Gly
    530                 535                 540
Val Pro Gly Ala Gly Val Pro Gly Gly Gly Val Pro Gly Ala Gly Val
545                 550                 555                 560
Pro Gly Gly Gly Val Pro Gly Ala Gly Val Pro Gly Gly Gly Val Pro
                565                 570                 575
Gly Ala Gly Val Pro Gly Gly Gly Val Pro Gly Ala Gly Val Pro Gly
                580                 585                 590
Val Gly Val Pro Gly Ala Gly Val Pro Gly Gly Gly Val Pro Gly Ala
                595                 600                 605
Gly Val Pro Gly Gly Gly Val Pro Gly Ala Gly Val Pro Gly Gly Gly
    610                 615                 620
Val Pro Gly Ala Gly Val Pro Gly Gly Gly Val Pro Gly Ala Gly Val
625                 630                 635                 640
Pro Gly Gly Gly Val Pro Gly Ala Gly Val Pro Gly Gly Gly Val Pro
                645                 650                 655
Gly Ala Gly Val Pro Gly Gly Gly Val Pro Gly Ala Gly Val Pro Gly
                660                 665                 670
Val Gly Val Pro Gly Ala Gly Val Pro Gly Gly Gly Val Pro Gly Ala
                675                 680                 685
Gly Val Pro Gly Gly Gly Val Pro Gly Ala Gly Val Pro Gly Gly Gly
    690                 695                 700
Val Pro Gly Ala Gly Val Pro Gly Gly Gly Val Pro Gly Ala Gly Val
705                 710                 715                 720
Pro Gly Gly Gly Val Pro Gly Ala Gly Val Pro Gly Gly Gly Val Pro
                725                 730                 735
Gly Ala Gly Val Pro Gly Gly Gly Val Pro Gly Ala Gly Val Pro Gly
                740                 745                 750
Val Gly Val Pro Gly Ala Gly Val Pro Gly Gly Gly Val Pro Gly Ala
                755                 760                 765
Gly Val Pro Gly Gly Gly Val Pro Gly Ala Gly Val Pro Gly Gly Gly
    770                 775                 780
Val Pro Gly Ala Gly Val Pro Gly Gly Gly Val Pro Gly Ala Gly Val
```

```
                785                 790                 795                 800
Pro Gly Gly Gly Val Pro Gly Ala Gly Val Pro Gly Gly Val Pro
                    805                 810                 815
Gly Ala Gly Val Pro Gly Gly Val Pro Gly Ala Gly Val Pro Gly
                    820                 825                 830
Trp Pro Gly Ser Gly Gly Cys
                    835

<210> SEQ ID NO 33
<211> LENGTH: 780
<212> TYPE: PRT
<213> ORGANISM: Artificial Sequence
<220> FEATURE:
<223> OTHER INFORMATION: pVEC-ELP1

<400> SEQUENCE: 33

Met Leu Leu Ile Ile Leu Arg Arg Arg Ile Arg Lys Gln Ala His Ala
1               5                   10                  15
His Ser Lys Gly Gly Pro Gly Val Gly Val Pro Gly Val Gly Val Pro
                20                  25                  30
Gly Gly Gly Val Pro Gly Ala Gly Val Pro Gly Val Gly Val Pro Gly
                35                  40                  45
Val Gly Val Pro Gly Val Gly Val Pro Gly Gly Gly Val Pro Gly Ala
            50                  55                  60
Gly Val Pro Gly Gly Val Pro Gly Val Gly Val Pro Gly Val Gly
65                  70                  75                  80
Val Pro Gly Gly Val Pro Gly Ala Gly Val Pro Gly Val Gly Val
                85                  90                  95
Pro Gly Val Gly Val Pro Gly Val Gly Val Pro Gly Gly Gly Val Pro
                100                 105                 110
Gly Ala Gly Val Pro Gly Gly Val Pro Gly Val Gly Val Pro Gly
                115                 120                 125
Val Gly Val Pro Gly Gly Val Pro Gly Ala Gly Val Pro Gly Val
            130                 135                 140
Gly Val Pro Gly Val Gly Val Pro Gly Val Gly Val Pro Gly Gly Gly
145                 150                 155                 160
Val Pro Gly Ala Gly Val Pro Gly Gly Val Pro Gly Val Gly Val
                165                 170                 175
Pro Gly Val Gly Val Pro Gly Gly Val Pro Gly Ala Gly Val Pro
                180                 185                 190
Gly Val Gly Val Pro Gly Val Gly Val Pro Gly Val Gly Val Pro Gly
                195                 200                 205
Gly Gly Val Pro Gly Ala Gly Val Pro Gly Gly Val Pro Gly Val
            210                 215                 220
Gly Val Pro Gly Val Gly Val Pro Gly Gly Val Pro Gly Ala Gly
225                 230                 235                 240
Val Pro Gly Val Gly Val Pro Gly Val Gly Val Pro Gly Val Gly Val
                245                 250                 255
Pro Gly Gly Gly Val Pro Gly Ala Gly Val Pro Gly Gly Val Pro
                260                 265                 270
Gly Val Gly Val Pro Gly Val Gly Val Pro Gly Gly Val Pro Gly
                275                 280                 285
Ala Gly Val Pro Gly Val Gly Val Pro Gly Val Gly Val Pro Gly Val
            290                 295                 300
Gly Val Pro Gly Gly Gly Val Pro Gly Ala Gly Val Pro Gly Gly Gly
```

```
            305                 310                 315                 320
        Val Pro Gly Val Gly Val Pro Gly Val Gly Val Pro Gly Gly Val
                        325                 330                 335
        Pro Gly Ala Gly Val Pro Gly Val Gly Val Pro Gly Val Gly Val Pro
                        340                 345                 350
        Gly Val Gly Val Pro Gly Gly Val Pro Gly Ala Gly Val Pro Gly
                        355                 360                 365
        Gly Gly Val Pro Gly Val Gly Val Pro Gly Val Gly Val Pro Gly Gly
                        370                 375                 380
        Gly Val Pro Gly Ala Gly Val Pro Gly Val Gly Val Pro Gly Val Gly
        385                 390                 395                 400
        Val Pro Gly Val Gly Val Pro Gly Gly Val Pro Gly Ala Gly Val
                        405                 410                 415
        Pro Gly Gly Gly Val Pro Gly Val Gly Val Pro Gly Val Gly Val Pro
                        420                 425                 430
        Gly Gly Gly Val Pro Gly Ala Gly Val Pro Gly Val Gly Val Pro Gly
                        435                 440                 445
        Val Gly Val Pro Gly Val Gly Val Pro Gly Gly Val Pro Gly Ala
                        450                 455                 460
        Gly Val Pro Gly Gly Gly Val Pro Gly Val Gly Val Pro Gly Val Gly
        465                 470                 475                 480
        Val Pro Gly Gly Gly Val Pro Gly Ala Gly Val Pro Gly Val Gly Val
                        485                 490                 495
        Pro Gly Val Gly Val Pro Gly Val Gly Val Pro Gly Gly Gly Val Pro
                        500                 505                 510
        Gly Ala Gly Val Pro Gly Gly Gly Val Pro Gly Val Gly Val Pro Gly
                        515                 520                 525
        Val Gly Val Pro Gly Gly Gly Val Pro Gly Ala Gly Val Pro Gly Val
                        530                 535                 540
        Gly Val Pro Gly Val Gly Val Pro Gly Val Gly Val Pro Gly Gly Gly
        545                 550                 555                 560
        Val Pro Gly Ala Gly Val Pro Gly Gly Gly Val Pro Gly Val Gly Val
                        565                 570                 575
        Pro Gly Val Gly Val Pro Gly Gly Gly Val Pro Gly Ala Gly Val Pro
                        580                 585                 590
        Gly Val Gly Val Pro Gly Val Gly Val Pro Gly Val Gly Val Pro Gly
                        595                 600                 605
        Gly Gly Val Pro Gly Ala Gly Val Pro Gly Gly Gly Val Pro Gly Val
                        610                 615                 620
        Gly Val Pro Gly Val Gly Val Pro Gly Gly Gly Val Pro Gly Ala Gly
        625                 630                 635                 640
        Val Pro Gly Val Gly Val Pro Gly Val Gly Val Pro Gly Val Gly Val
                        645                 650                 655
        Pro Gly Gly Gly Val Pro Gly Ala Gly Val Pro Gly Gly Gly Val Pro
                        660                 665                 670
        Gly Val Gly Val Pro Gly Val Gly Val Pro Gly Gly Gly Val Pro Gly
                        675                 680                 685
        Ala Gly Val Pro Gly Val Gly Val Pro Gly Val Gly Val Pro Gly Val
                        690                 695                 700
        Gly Val Pro Gly Gly Gly Val Pro Gly Ala Gly Val Pro Gly Gly Gly
        705                 710                 715                 720
        Val Pro Gly Val Gly Val Pro Gly Val Gly Val Pro Gly Gly Gly Val
                        725                 730                 735
```

```
Pro Gly Ala Gly Val Pro Val Gly Val Pro Val Gly Val Pro
            740                 745                 750
Gly Val Gly Val Pro Gly Gly Val Pro Gly Ala Gly Val Pro Gly
            755                 760                 765
Gly Gly Val Pro Gly Trp Pro Gly Ser Gly Gly Cys
            770                 775             780

<210> SEQ ID NO 34
<211> LENGTH: 830
<212> TYPE: PRT
<213> ORGANISM: Artificial Sequence
<220> FEATURE:
<223> OTHER INFORMATION: pVEC-ELP2

<400> SEQUENCE: 34

Met Leu Leu Ile Ile Leu Arg Arg Arg Ile Arg Lys Gln Ala His Ala
1               5                   10                  15
His Ser Lys Gly Gly Pro Gly Val Gly Val Pro Gly Ala Gly Val Pro
            20                  25                  30
Gly Gly Gly Val Pro Gly Ala Gly Val Pro Gly Gly Gly Val Pro Gly
            35                  40                  45
Ala Gly Val Pro Gly Gly Gly Val Pro Gly Ala Gly Val Pro Gly Gly
        50                  55                  60
Gly Val Pro Gly Ala Gly Val Pro Gly Gly Gly Val Pro Gly Ala Gly
65                  70                  75                  80
Val Pro Gly Gly Gly Val Pro Gly Ala Gly Val Pro Gly Gly Gly Val
                85                  90                  95
Pro Gly Ala Gly Val Pro Gly Val Gly Val Pro Gly Ala Gly Val Pro
            100                 105                 110
Gly Gly Gly Val Pro Gly Ala Gly Val Pro Gly Gly Gly Val Pro Gly
            115                 120                 125
Ala Gly Val Pro Gly Gly Gly Val Pro Gly Ala Gly Val Pro Gly Gly
        130                 135                 140
Gly Val Pro Gly Ala Gly Val Pro Gly Gly Gly Val Pro Gly Ala Gly
145                 150                 155                 160
Val Pro Gly Gly Gly Val Pro Gly Ala Gly Val Pro Gly Gly Gly Val
                165                 170                 175
Pro Gly Ala Gly Val Pro Gly Val Gly Val Pro Gly Ala Gly Val Pro
            180                 185                 190
Gly Gly Gly Val Pro Gly Ala Gly Val Pro Gly Gly Gly Val Pro Gly
            195                 200                 205
Ala Gly Val Pro Gly Gly Gly Val Pro Gly Ala Gly Val Pro Gly Gly
        210                 215                 220
Gly Val Pro Gly Ala Gly Val Pro Gly Gly Gly Val Pro Gly Ala Gly
225                 230                 235                 240
Val Pro Gly Gly Gly Val Pro Gly Ala Gly Val Pro Gly Gly Gly Val
                245                 250                 255
Pro Gly Ala Gly Val Pro Gly Val Gly Val Pro Gly Ala Gly Val Pro
            260                 265                 270
Gly Gly Gly Val Pro Gly Ala Gly Val Pro Gly Gly Gly Val Pro Gly
            275                 280                 285
Ala Gly Val Pro Gly Gly Gly Val Pro Gly Ala Gly Val Pro Gly Gly
        290                 295                 300
Gly Val Pro Gly Ala Gly Val Pro Gly Gly Gly Val Pro Gly Ala Gly
305                 310                 315                 320
```

-continued

```
Val Pro Gly Gly Gly Val Pro Gly Ala Gly Val Pro Gly Gly Gly Val
                325                 330                 335
Pro Gly Ala Gly Val Pro Gly Val Gly Val Pro Gly Ala Gly Val Pro
                340                 345                 350
Gly Gly Gly Val Pro Gly Ala Gly Val Pro Gly Gly Gly Val Pro Gly
                355                 360                 365
Ala Gly Val Pro Gly Gly Gly Val Pro Gly Ala Gly Val Pro Gly Gly
                370                 375                 380
Gly Val Pro Gly Ala Gly Val Pro Gly Gly Gly Val Pro Gly Ala Gly
385                 390                 395                 400
Val Pro Gly Gly Gly Val Pro Gly Ala Gly Val Pro Gly Gly Gly Val
                405                 410                 415
Pro Gly Ala Gly Val Pro Gly Val Gly Val Pro Gly Ala Gly Val Pro
                420                 425                 430
Gly Gly Gly Val Pro Gly Ala Gly Val Pro Gly Gly Gly Val Pro Gly
                435                 440                 445
Ala Gly Val Pro Gly Gly Gly Val Pro Gly Ala Gly Val Pro Gly Gly
                450                 455                 460
Gly Val Pro Gly Ala Gly Val Pro Gly Gly Gly Val Pro Gly Ala Gly
465                 470                 475                 480
Val Pro Gly Gly Gly Val Pro Gly Ala Gly Val Pro Gly Gly Gly Val
                485                 490                 495
Pro Gly Ala Gly Val Pro Gly Val Gly Val Pro Gly Ala Gly Val Pro
                500                 505                 510
Gly Gly Gly Val Pro Gly Ala Gly Val Pro Gly Gly Gly Val Pro Gly
                515                 520                 525
Ala Gly Val Pro Gly Gly Gly Val Pro Gly Ala Gly Val Pro Gly Gly
                530                 535                 540
Gly Val Pro Gly Ala Gly Val Pro Gly Gly Gly Val Pro Gly Ala Gly
545                 550                 555                 560
Val Pro Gly Gly Gly Val Pro Gly Ala Gly Val Pro Gly Gly Gly Val
                565                 570                 575
Pro Gly Ala Gly Val Pro Gly Val Gly Val Pro Gly Ala Gly Val Pro
                580                 585                 590
Gly Gly Gly Val Pro Gly Ala Gly Val Pro Gly Gly Gly Val Pro Gly
                595                 600                 605
Ala Gly Val Pro Gly Gly Gly Val Pro Gly Ala Gly Val Pro Gly Gly
                610                 615                 620
Gly Val Pro Gly Ala Gly Val Pro Gly Gly Gly Val Pro Gly Ala Gly
625                 630                 635                 640
Val Pro Gly Gly Gly Val Pro Gly Ala Gly Val Pro Gly Gly Gly Val
                645                 650                 655
Pro Gly Ala Gly Val Pro Gly Val Gly Val Pro Gly Ala Gly Val Pro
                660                 665                 670
Gly Gly Gly Val Pro Gly Ala Gly Val Pro Gly Gly Gly Val Pro Gly
                675                 680                 685
Ala Gly Val Pro Gly Gly Gly Val Pro Gly Ala Gly Val Pro Gly Gly
                690                 695                 700
Gly Val Pro Gly Ala Gly Val Pro Gly Gly Gly Val Pro Gly Ala Gly
705                 710                 715                 720
Val Pro Gly Gly Gly Val Pro Gly Ala Gly Val Pro Gly Gly Gly Val
                725                 730                 735
```

```
Pro Gly Ala Gly Val Pro Gly Val Gly Val Pro Gly Ala Gly Val Pro
            740                 745                 750
Gly Gly Gly Val Pro Gly Ala Gly Val Pro Gly Gly Gly Val Pro Gly
        755                 760                 765
Ala Gly Val Pro Gly Gly Val Pro Gly Ala Gly Val Pro Gly Gly
    770                 775                 780
Gly Val Pro Gly Ala Gly Val Pro Gly Gly Val Pro Gly Ala Gly
785                 790                 795                 800
Val Pro Gly Gly Val Pro Gly Ala Gly Val Pro Gly Gly Gly Val
            805                 810                 815
Pro Gly Ala Gly Val Pro Gly Trp Pro Gly Ser Gly Gly Cys
            820                 825                 830

<210> SEQ ID NO 35
<211> LENGTH: 780
<212> TYPE: PRT
<213> ORGANISM: Artificial Sequence
<220> FEATURE:
<223> OTHER INFORMATION: SynB1-ELP1

<400> SEQUENCE: 35

Met Arg Gly Gly Arg Leu Ser Tyr Ser Arg Arg Phe Ser Thr Ser
1               5                   10                  15
Thr Gly Arg Gly Gly Pro Gly Val Gly Val Pro Gly Val Gly Val Pro
            20                  25                  30
Gly Gly Gly Val Pro Gly Ala Gly Val Pro Gly Val Gly Val Pro Gly
        35                  40                  45
Val Gly Val Pro Gly Val Gly Val Pro Gly Gly Val Pro Gly Ala
    50                  55                  60
Gly Val Pro Gly Gly Val Pro Gly Val Gly Val Pro Gly Val Gly
65                  70                  75                  80
Val Pro Gly Gly Val Pro Gly Ala Gly Val Pro Gly Val Gly Val
            85                  90                  95
Pro Gly Val Gly Val Pro Gly Val Gly Val Pro Gly Gly Gly Val Pro
            100                 105                 110
Gly Ala Gly Val Pro Gly Gly Gly Val Pro Gly Val Gly Val Pro Gly
        115                 120                 125
Val Gly Val Pro Gly Gly Gly Val Pro Gly Ala Gly Val Pro Gly Val
    130                 135                 140
Gly Val Pro Gly Val Gly Val Pro Gly Val Gly Val Pro Gly Gly Gly
145                 150                 155                 160
Val Pro Gly Ala Gly Val Pro Gly Gly Gly Val Pro Gly Val Gly Val
            165                 170                 175
Pro Gly Val Gly Val Pro Gly Gly Gly Val Pro Gly Ala Gly Val Pro
            180                 185                 190
Gly Val Gly Val Pro Gly Val Gly Val Pro Gly Val Gly Val Pro Gly
        195                 200                 205
Gly Gly Val Pro Gly Ala Gly Val Pro Gly Gly Gly Val Pro Gly Val
    210                 215                 220
Gly Val Pro Gly Val Gly Val Pro Gly Gly Gly Val Pro Gly Ala Gly
225                 230                 235                 240
Val Pro Gly Val Gly Val Pro Gly Val Gly Val Pro Gly Val Gly Val
            245                 250                 255
Pro Gly Gly Gly Val Pro Gly Ala Gly Val Pro Gly Gly Gly Val Pro
            260                 265                 270
```

-continued

```
Gly Val Gly Val Pro Gly Val Gly Val Pro Gly Gly Val Pro Gly
            275                 280                 285
Ala Gly Val Pro Gly Val Gly Val Pro Gly Val Gly Val Pro Gly Val
290                 295                 300
Gly Val Pro Gly Gly Val Pro Gly Ala Gly Val Pro Gly Val Gly Gly
305                 310                 315                 320
Val Pro Gly Val Gly Val Pro Gly Val Gly Val Pro Gly Gly Val
            325                 330                 335
Pro Gly Ala Gly Val Pro Gly Val Gly Val Pro Gly Val Gly Val Pro
            340                 345                 350
Gly Val Gly Val Pro Gly Gly Val Pro Gly Ala Gly Val Pro Gly
            355                 360                 365
Gly Gly Val Pro Gly Val Gly Val Pro Gly Val Gly Val Pro Gly Gly
            370                 375                 380
Val Pro Gly Ala Gly Val Pro Gly Val Gly Val Pro Gly Val Gly
385                 390                 395                 400
Val Pro Gly Val Gly Val Pro Gly Gly Val Pro Gly Ala Gly Val
            405                 410                 415
Pro Gly Gly Gly Val Pro Gly Val Gly Val Pro Gly Val Gly Val Pro
            420                 425                 430
Gly Gly Gly Val Pro Gly Ala Gly Val Pro Gly Val Gly Val Pro Gly
            435                 440                 445
Val Gly Val Pro Gly Val Gly Val Pro Gly Gly Gly Val Pro Gly Ala
            450                 455                 460
Gly Val Pro Gly Gly Gly Val Pro Gly Val Gly Val Pro Gly Val Gly
465                 470                 475                 480
Val Pro Gly Gly Gly Val Pro Gly Ala Gly Val Pro Gly Val Gly Val
            485                 490                 495
Pro Gly Val Gly Val Pro Gly Val Gly Val Pro Gly Gly Gly Val Pro
            500                 505                 510
Gly Ala Gly Val Pro Gly Gly Gly Val Pro Gly Val Gly Val Pro Gly
            515                 520                 525
Val Gly Val Pro Gly Gly Gly Val Pro Gly Ala Gly Val Pro Gly Val
            530                 535                 540
Gly Val Pro Gly Val Gly Val Pro Gly Val Gly Val Pro Gly Gly Gly
545                 550                 555                 560
Val Pro Gly Ala Gly Val Pro Gly Gly Gly Val Pro Gly Val Gly Val
            565                 570                 575
Pro Gly Val Gly Val Pro Gly Gly Gly Val Pro Gly Ala Gly Val Pro
            580                 585                 590
Gly Val Gly Val Pro Gly Val Gly Val Pro Gly Val Gly Val Pro Gly
            595                 600                 605
Gly Gly Val Pro Gly Ala Gly Val Pro Gly Gly Gly Val Pro Gly Val
            610                 615                 620
Gly Val Pro Gly Val Gly Val Pro Gly Gly Gly Val Pro Gly Ala Gly
625                 630                 635                 640
Val Pro Gly Val Gly Val Pro Gly Val Gly Val Pro Gly Val Gly Val
            645                 650                 655
Pro Gly Gly Gly Val Pro Gly Ala Gly Val Pro Gly Gly Gly Val Pro
            660                 665                 670
Gly Val Gly Val Pro Gly Val Gly Val Pro Gly Gly Gly Val Pro Gly
            675                 680                 685
Ala Gly Val Pro Gly Val Gly Val Pro Gly Val Gly Val Pro Gly Val
```

```
                    690                 695                 700
Gly Val Pro Gly Gly Val Pro Gly Ala Gly Val Pro Gly Gly
705                 710                 715                 720

Val Pro Gly Val Gly Val Pro Gly Val Gly Val Pro Gly Gly Val
                725                 730                 735

Pro Gly Ala Gly Val Pro Gly Val Gly Val Pro Gly Val Gly Val Pro
                740                 745                 750

Gly Val Gly Val Pro Gly Gly Val Pro Gly Ala Gly Val Pro Gly
            755                 760                 765

Gly Gly Val Pro Gly Trp Pro Gly Ser Gly Gly Cys
        770                 775                 780

<210> SEQ ID NO 36
<211> LENGTH: 830
<212> TYPE: PRT
<213> ORGANISM: Artificial Sequence
<220> FEATURE:
<223> OTHER INFORMATION: SynB2-ELP2

<400> SEQUENCE: 36

Met Arg Gly Gly Arg Leu Ser Tyr Ser Arg Arg Phe Ser Thr Ser
1               5                   10                  15

Thr Gly Arg Gly Gly Pro Gly Val Gly Val Pro Gly Ala Gly Val Pro
                20                  25                  30

Gly Gly Val Pro Gly Ala Gly Val Pro Gly Gly Val Pro Gly
            35                  40                  45

Ala Gly Val Pro Gly Gly Val Pro Gly Ala Gly Val Pro Gly Gly
50                  55                  60

Gly Val Pro Gly Ala Gly Val Pro Gly Gly Val Pro Gly Ala Gly
65                  70                  75                  80

Val Pro Gly Gly Gly Val Pro Gly Ala Gly Val Pro Gly Gly Val
                85                  90                  95

Pro Gly Ala Gly Val Pro Gly Val Gly Val Pro Gly Ala Gly Val Pro
                100                 105                 110

Gly Gly Gly Val Pro Gly Ala Gly Val Pro Gly Gly Val Pro Gly
            115                 120                 125

Ala Gly Val Pro Gly Gly Val Pro Gly Ala Gly Val Pro Gly Gly
            130                 135                 140

Gly Val Pro Gly Ala Gly Val Pro Gly Gly Val Pro Gly Ala Gly
145                 150                 155                 160

Val Pro Gly Gly Gly Val Pro Gly Ala Gly Val Pro Gly Gly Val
                165                 170                 175

Pro Gly Ala Gly Val Pro Gly Gly Val Pro Gly Ala Gly Val Pro
                180                 185                 190

Gly Gly Gly Val Pro Gly Ala Gly Val Pro Gly Gly Val Pro Gly
            195                 200                 205

Ala Gly Val Pro Gly Gly Val Pro Gly Ala Gly Val Pro Gly Gly
            210                 215                 220

Gly Val Pro Gly Ala Gly Val Pro Gly Gly Val Pro Gly Ala Gly
225                 230                 235                 240

Val Pro Gly Gly Gly Val Pro Gly Ala Gly Val Pro Gly Gly Val
                245                 250                 255

Pro Gly Ala Gly Val Pro Gly Gly Val Pro Gly Ala Gly Val Pro
                260                 265                 270

Gly Gly Gly Val Pro Gly Ala Gly Val Pro Gly Gly Val Pro Gly
```

-continued

```
                275                 280                 285
Ala Gly Val Pro Gly Gly Gly Val Pro Gly Ala Gly Val Pro Gly Gly
    290                 295                 300
Gly Val Pro Gly Ala Gly Val Pro Gly Gly Gly Val Pro Gly Ala Gly
305                 310                 315                 320
Val Pro Gly Gly Gly Val Pro Gly Ala Gly Val Pro Gly Gly Gly Val
                325                 330                 335
Pro Gly Ala Gly Val Pro Gly Val Gly Val Pro Gly Ala Gly Val Pro
            340                 345                 350
Gly Gly Gly Val Pro Gly Ala Gly Val Pro Gly Gly Gly Val Pro Gly
            355                 360                 365
Ala Gly Val Pro Gly Gly Gly Val Pro Gly Ala Gly Val Pro Gly Gly
        370                 375                 380
Gly Val Pro Gly Ala Gly Val Pro Gly Gly Gly Val Pro Gly Ala Gly
385                 390                 395                 400
Val Pro Gly Gly Gly Val Pro Gly Ala Gly Val Pro Gly Gly Gly Val
                405                 410                 415
Pro Gly Ala Gly Val Pro Gly Val Gly Val Pro Gly Ala Gly Val Pro
            420                 425                 430
Gly Gly Gly Val Pro Gly Ala Gly Val Pro Gly Gly Gly Val Pro Gly
            435                 440                 445
Ala Gly Val Pro Gly Gly Gly Val Pro Gly Ala Gly Val Pro Gly Gly
        450                 455                 460
Gly Val Pro Gly Ala Gly Val Pro Gly Gly Gly Val Pro Gly Ala Gly
465                 470                 475                 480
Val Pro Gly Gly Gly Val Pro Gly Ala Gly Val Pro Gly Gly Gly Val
                485                 490                 495
Pro Gly Ala Gly Val Pro Gly Val Gly Val Pro Gly Ala Gly Val Pro
            500                 505                 510
Gly Gly Gly Val Pro Gly Ala Gly Val Pro Gly Gly Gly Val Pro Gly
            515                 520                 525
Ala Gly Val Pro Gly Gly Gly Val Pro Gly Ala Gly Val Pro Gly Gly
        530                 535                 540
Gly Val Pro Gly Ala Gly Val Pro Gly Gly Gly Val Pro Gly Ala Gly
545                 550                 555                 560
Val Pro Gly Gly Gly Val Pro Gly Ala Gly Val Pro Gly Gly Gly Val
                565                 570                 575
Pro Gly Ala Gly Val Pro Gly Val Gly Val Pro Gly Ala Gly Val Pro
            580                 585                 590
Gly Gly Gly Val Pro Gly Ala Gly Val Pro Gly Gly Gly Val Pro Gly
            595                 600                 605
Ala Gly Val Pro Gly Gly Gly Val Pro Gly Ala Gly Val Pro Gly Gly
        610                 615                 620
Gly Val Pro Gly Ala Gly Val Pro Gly Gly Gly Val Pro Gly Ala Gly
625                 630                 635                 640
Val Pro Gly Gly Gly Val Pro Gly Ala Gly Val Pro Gly Gly Gly Val
                645                 650                 655
Pro Gly Ala Gly Val Pro Gly Val Gly Val Pro Gly Ala Gly Val Pro
            660                 665                 670
Gly Gly Gly Val Pro Gly Ala Gly Val Pro Gly Gly Gly Val Pro Gly
            675                 680                 685
Ala Gly Val Pro Gly Gly Gly Val Pro Gly Ala Gly Val Pro Gly Gly
        690                 695                 700
```

```
Gly Val Pro Gly Ala Gly Val Pro Gly Gly Gly Val Pro Gly Ala Gly
705                 710                 715                 720

Val Pro Gly Gly Gly Val Pro Gly Ala Gly Val Pro Gly Gly Gly Val
                725                 730                 735

Pro Gly Ala Gly Val Pro Gly Val Gly Val Pro Gly Ala Gly Val Pro
            740                 745                 750

Gly Gly Gly Val Pro Gly Ala Gly Val Pro Gly Gly Gly Val Pro Gly
            755                 760                 765

Ala Gly Val Pro Gly Gly Val Pro Gly Ala Gly Val Pro Gly Gly
    770                 775                 780

Gly Val Pro Gly Ala Gly Val Pro Gly Gly Gly Val Pro Gly Ala Gly
785                 790                 795                 800

Val Pro Gly Gly Gly Val Pro Gly Ala Gly Val Pro Gly Gly Gly Val
                805                 810                 815

Pro Gly Ala Gly Val Pro Gly Trp Pro Gly Ser Gly Gly Cys
            820                 825                 830

<210> SEQ ID NO 37
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: X
<222> LOCATION: (4)..(4)
<223> OTHER INFORMATION: X= valine, glicine, or alanine

<400> SEQUENCE: 37

Val Pro Gly Xaa Gly
1               5
```

INHIBITION OF METASTASIS BY CELL PENETRATING PEPTIDES

PRIOR APPLICATIONS

This application is a continuation-in-part of U.S. patent application Ser. No. 12/422,975 filed on Apr. 13, 2009, now abandoned, which claims benefit to U.S. Patent Application No. 61/044,398, filed on Apr. 11, 2008; and this application is a continuation-in-part of U.S. patent application Ser. No. 12/162,283, filed Jun. 24, 2009, now issued as U.S. Pat. No. 8,252,740, which is a national phase application of International Patent Application No. PCT/US07/61240, filed on Jan. 29, 2007, which claims benefit to U.S. Patent Application No. 60/762,919, filed on Jan. 27, 2006. The content of patent application Ser. Nos. 12/422,975; 61/044,398; 12/162,283; PCT/US07/61240; and 60/762,919 are incorporated herein by reference.

INTRODUCTION AND SUMMARY OF THE INVENTION

Embodiments of the present invention include a compound having a cell penetrating peptide (CPP) fused to an elastin-like polypeptide (ELP), and a method of using the compound as an anti-metastases agent.

Tumor cell metastasis is a complex, multi-step process that is a major cause of death and morbidity amongst cancer patients. Cell adhesion plays a critical role in the development of metastatic cancer, and it is mediated by interactions between receptors on the cell surface and ligands of the extracellular matrix or other surfaces. Therefore, inhibition of the cell adhesion process appears to be an effective method of preventing metastasis.

To prevent cell adhesion the present inventors developed, as part of the present invention, genetically engineered polypeptides with the potential to inhibit metastases. Embodiments of the present invention include the cell penetrating peptides (CPP) Tat or penetratin (Pen), fused with elastin-like polypeptide (CPP-ELP) inhibited adhesion, spreading, invasion and migration of SKOV-3 ovarian cancer cells, SK-MEL-2 melanoma cells, and MDA-MB-231 breast cancer cells. Additionally, examples of the present invention include the administration of Tat-ELP for anti-metastatic treatment methods.

Accordingly, the polypeptides and other embodiments of the present invention are useful and needed as a therapeutic intervention in cancer metastasis.

Metastasis is the direct cause of mortality in most cancer patients. Therefore, efforts to understand and prevent the metastatic process are of tremendous clinical importance. While several approaches are being pursued to target cancer cell growth, relatively few focus specifically on preventing metastasis with drugs that can be safely administered on a long-term basis. Given the importance of metastasis as the major cause of increased morbidity and eventual mortality in cancer patients, the development of agents, such as the anti-adhesive polypeptide described here, that prevent or significantly delay metastasis without excessive collateral toxicity to other organs, would offer tremendous potential clinical benefit.

Since the adhesive interaction between tumor cells and host cells or extracellular matrix (ECM) plays a crucial role in metastatic formation (1-3), inhibition of the cell adhesion process appears to be an effective method of preventing metastasis. Rapid progress has been made in structural and functional analysis of cellular adhesive molecules involved in cell-cell or cell-ECM interactions. Several studies have suggested that synthetic peptides derived from adhesion molecules that are present in extracellular matrices or basement membranes can modulate the mechanism involved in metastasizing tumor cells (4, 5). It has been shown that peptides such as YIGSR, comprising residues 929-933 on the $\beta_1$ chain of laminin, and the RGDS sequence in the central cell-binding domain of fibronectin can reduce formation of human melanoma tumors in nude mice (6, 7). However, most of these peptides as well some cytokines or anti-cancer drugs have very short half lives in the circulation, which results in a decrease in therapeutic and biological effect in vivo. Therefore, an increase in the half-life of a drug in circulation without increasing its toxicity may lead to improved biological effect. Previous studies have shown that conjugation of RGD and YIGSR containing peptides with various drug carriers such as polyethylene glycol, poly (carboxymethylmethacrylamide), carboxymethyl chitin, and bovine serum albumin increased the inhibition of experimental and spontaneous tumor metastases (8, 9). Although bioconjugation of peptides with polymeric modifiers improved the plasma clearance and body distribution, most of these polymers are limited in their clinical application. Therefore, further improvements that increase the therapeutic effect and decrease side effects are needed.

The present inventors have found that the cell penetrating peptides of the present invention, such as Tat or penetratin, fused with elastin-like polypeptide (CPP-ELP), inhibited ovarian cancer, breast cancer and melanoma cell adhesion, spreading, invasion and migration. The polypeptides of the present invention have great potential as a therapeutic intervention in cancer metastasis. There are several advantages of these novel ELP-based polypeptides over existing anti-adhesion polymers. First, while classical approaches rely on chemical synthesis of anti-adhesive peptides and chemical conjugation of anti-adhesive peptides to carriers, we produce an anti-adhesive peptide using simple molecular biology techniques. The coding sequence for ELP may be modified by addition of the cell penetrating peptide (CPP) or any other peptide with anti-metastatic properties. Second, ELPs consist of Val-Pro-Gly-Xaa-Gly (VPGXG (SEQ ID NO: 37)) repeated units, and they are attractive from a molecular design perspective for targeted drug delivery because they are genetically encoded, which provides control over the ELP sequence and molecular weight (MW) to an extent that is impossible with synthetic polymer analogs. Control of macromolecular chain length and polydispersity is important because it controls the residence time of the drug-polymer conjugate in systemic circulation (10, 11) (please see Section I, FIG. 20 for preliminary results of plasma clearance). Finally, an additional advantage of ELP-based genetically encoded polypeptides over synthetic polymer carriers is that they are thermally responsive. Therefore, they may be expressed and purified from *E. coli* by a simple process called thermal cycling, which easily produces a large quantity of the purified polypeptide (12, 13).

Cell penetrating peptides are known for their ability to mediate cellular uptake of large proteins and macromolecules (reviewed in (14-16)). Also, the penetratin peptide intracellular delivery system has been patented (U.S. Pat. No. 6,844,324, to Zhang et al.).

BRIEF DESCRIPTION OF THE SEQUENCE LISTING

SEQ ID NO: 1 is a Tat cell penetrating polypeptide.
SEQ ID NO: 2 is a Penetratin cell penetrating polypeptide.
SEQ ID NO: 3 is a Bac cell penetrating polypeptide.
SEQ ID NO: 4 is a SynB1 cell penetrating polypeptide.
SEQ ID NO: 5 is a Syn B1-NLS cell penetrating polypeptide.
SEQ ID NO: 6 is a poly-arginine cell penetrating polypeptide including seven (7) arginines.
SEQ ID NO: 7 is a poly-arginine cell penetrating polypeptide including eight (8) arginines.
SEQ ID NO: 8 is a poly-arginine cell penetrating polypeptide including nine (9) arginines.
SEQ ID NO: 9 is a poly-arginine cell penetrating polypeptide including ten (10) arginines.
SEQ ID NO: 10 is a poly-arginine cell penetrating polypeptide including eleven (11) arginines.
SEQ ID NO: 11 is a VP22 cell penetrating polypeptide.
SEQ ID NO: 12 is a Transportan cell penetrating polypeptide.
SEQ ID NO: 13 is a MAP cell penetrating polypeptide.
SEQ ID NO: 14 is a pVEC cell penetrating polypeptide.
SEQ ID NO: 15 is a MTS cell penetrating polypeptide.
SEQ ID NO: 16 is a hCT-derived cell penetrating polypeptide.
SEQ ID NO: 17 is a MPG cell penetrating polypeptide.
SEQ ID NO: 18 is a Buforin 2 cell penetrating polypeptide.
SEQ ID NO: 19 is a PEP-1 cell penetrating polypeptide.
SEQ ID NO: 20 is a Magainin 2 cell penetrating polypeptide.
SEQ ID NO: 21 is an embodiment of an elastin-like polypeptide that includes repeating units of the amino acid sequence VPGXG (SEQ ID NO: 37), where each X is independently selected from valine, glycine, and alanine such that the Xs are provided in a 5:3:2 ratio.
SEQ ID NO: 22 is an embodiment of an elastin-like polypeptide that includes repeating units of the amino acid sequence VPGXG (SEQ ID NO: 37), where each X is independently selected from valine, glycine, and alanine such that the Xs are provided in a 1:7:8 ratio.
SEQ ID NO: 23 is an embodiment of an amino acid comprising a Tat cell penetrating polypeptide and an elastin-like polypeptide.
SEQ ID NO: 24 is another embodiment of an amino acid including a Tat cell penetrating polypeptide and an elastin-like polypeptide.
SEQ ID NO: 25 is an embodiment of an amino acid including a Penetratin cell penetrating polypeptide and an elastin-like polypeptide.
SEQ ID NO: 26 is another embodiment of an amino acid including a Penetratin cell penetrating polypeptide and an elastin-like polypeptide.
SEQ ID NO: 27 is an embodiment of an amino acid including an MTS cell penetrating polypeptide and an elastin-like polypeptide.
SEQ ID NO: 28 is another embodiment of an amino acid including an MTS cell penetrating polypeptide and an elastin-like polypeptide.
SEQ ID NO: 29 is an embodiment of an amino acid including a Bac-7 cell penetrating polypeptide and an elastin-like polypeptide.
SEQ ID NO: 30 is another embodiment of an amino acid including a Bac-7 cell penetrating polypeptide and an elastin-like polypeptide.
SEQ ID NO: 31 is an embodiment of an amino acid including a Transportan cell penetrating polypeptide and an elastin-like polypeptide.
SEQ ID NO: 32 is another embodiment of an amino acid including a Transportan cell penetrating polypeptide and an elastin-like polypeptide.
SEQ ID NO: 33 is an embodiment of an amino acid including a pVEC cell penetrating polypeptide and an elastin-like polypeptide.
SEQ ID NO: 34 is another embodiment of an amino acid including a pVEC cell penetrating polypeptide and an elastin-like polypeptide.
SEQ ID NO: 35 is an embodiment of an amino acid including a SynB1 cell penetrating polypeptide and an elastin-like polypeptide.
SEQ ID NO: 36 is another embodiment of an amino acid including a SynB1 cell penetrating polypeptide and an elastin-like polypeptide.
SEQ ID NO: 37 is a VPGXG unit, wherein each X is independently selected from valine, glycine, and alanine.

BRIEF DESCRIPTION OF THE DRAWINGS

FIG. 14A shows % migration of SKOV-3 cells were incubated with the indicated polypeptides at a fixed concentration for 10 min at 37° C., added to the upper chamber of the boyden chamber insert and allowed to migrate for 24 h. Cells were washed, fixed, stained with hematoxylin and 4 random fields were counted at 20× magnification. FIG. 14B is a set of images after cells were later incubated with Hoechst dye for 10 min. and images were obtained at 10× magnification.

FIG. 17a shows binding with Tat-ELP. FIG. 17B shows binding with MTS-ELP. FIG. 17C shows binding with ELP.

DESCRIPTION OF EMBODIMENTS OF THE INVENTION

Figure 1:
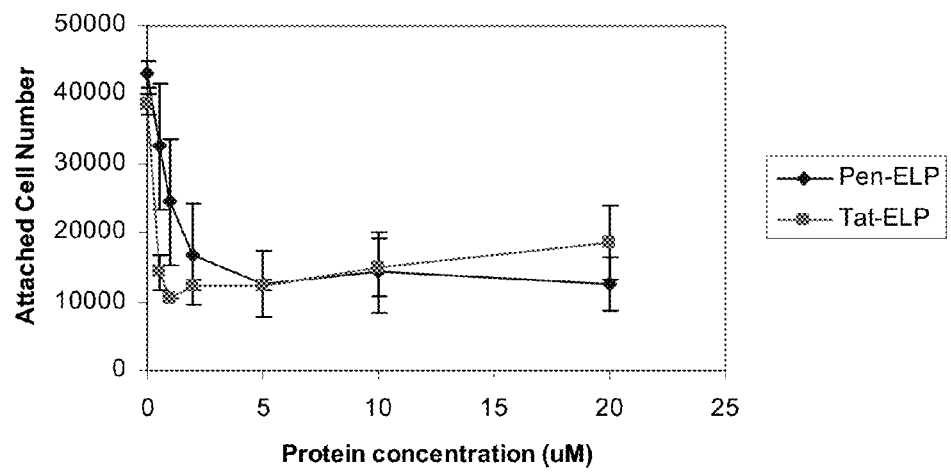
FIG. 1 is a chart showing in vitro attachment inhibition. MDA-MB-231 cells were exposed to polypeptides at the indicated concentration during a 3 h plating period in gelatin-coated dishes. Floating cells were harvested and counted. Results represent the mean±SEM of at least 3 independent experiments.

The present invention includes a compound for inhibiting proliferation of cancer, including a cell penetrating polypeptide (CPP) and an elastin-like polypeptide (ELP). In some embodiments, the compound can be administered to a subject to inhibit the proliferation of a cancer in the subject.

As used herein, the term "cell penetrating polypeptide" (CPP) refers to a polypeptide that facilitates transport of the compound through a cell membrane.

As used herein, the term "polypeptide" means any polymer comprising any of the 20 protein amino acids, regardless of its size. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted.

Cell penetrating peptides can be short polypeptides capable of mediating delivery of molecules across a cell membrane. In some embodiments, CPPs can be comprised of mostly basic amino acids, hydrophobic amino acids, or an amphipathic sequence. Examples of CPPs that can be used in accordance with the present invention include, but are not limited, to those set forth in Table 1.

TABLE 1

| CPP | Amino Acid Sequence | SEQ ID NO: |
| --- | --- | --- |
| Tat[1] | YGRKKRRQRRR | 1 |
| Penetratin (Antp)[2] | RQIKIWFQNRRMKWKK | 2 |
| Bac[3] | RRIRPRPPRLPRPRPRPLPFPRPG | 3 |
| SynB1 | RGGRLSYSRRRFSTSTGR | 4 |
| SynB1-NLS[4] | RGGRLSYSRRRFSTSTGRWSQPKKKRKV | 5 |
| Poly-arginine | (R)$_{7-11}$ | 6, 7, 8, 9, 10 |
| VP22 | DAATATRGRSAASRPTQRPRAPARSASRPRRPVQ | 11 |
| Transportan[5] | GWTLNSAGYLLGKINLKALAALAKKIL | 12 |

TABLE 1-continued

| CPP | Amino Acid Sequence | SEQ ID NO: |
|---|---|---|
| MAP | KLALKLALKALKAALKLA | 13 |
| pVEC[6] | LLIILRRRIRKQAHAHSK | 14 |
| MTS[7] | AAVALLPAVLLALLAP | 15 |
| hCT derived | LGTYTQDFNKFHTFPQTAIGVGAP | 16 |
| MPG | GALFLGFLGAAGSTMGAWSQPKKKRKV | 17 |
| Buforin 2 | TRSSRAGLQFPVGRVHRLLRK | 18 |
| PEP-1 | KETWWETWWTEWSQPKKKRKV | 19 |
| Magainin 2 | GIGKFLHSAKKFGKAFVGEIMNS | 20 |

[1]Tat is a cell penetrating peptide derived from the HIV-1 Tat protein (18).
[2]Penetratin (commonly abbreviated Pen or AntP) is the penetratin peptide derived from the *Drosophila* transcription factor Antennapaedia (17).
[3]Bac-7 is an antimicrobial peptide from the Bactenecin-7 family (20).
[4]SynB1-NLS is a version of the SynB1 CPP modified in the present inventors' lab by the addition of a nuclear localization sequence (NLS, underlined amino acids) to allow delivery of the compound not only across the cell membrane, but also into the cell's nucleus.
[5]Transportan is a chimeric peptide in which the first 13 amino acids are derived from galanin and the other 14 amino acids from the wasp venom peptide toxin, mastoparan (21).
[6]pVEC is derived from murine Vascular Endothelial Cadherin (22).
[7]MTS is the membrane translocating sequence derived from Kaposi fibroblast growth factor (19).

Embodiments of compounds of the present invention further include an elastin-like polypeptide (ELP) that is fused to the CPP (e.g., fusion protein including an ELP and a CPP). IN some embodiments, the CPP and the ELP are provided as a fusion protein, wherein the CPP is fused directly to the ELP. In some embodiments the CPP and the ELP are provided as a fusion protein, wherein linker comprising one or more amino acids is disposed between the CPP and the ELP.

In some embodiments, the ELP is an approximately 60 kilodalton protein comprising repeated units of the amino acid sequence VPGXG (SEQ ID NO: 37), where each X is independently selected from valine (Val; V), glycine (Gly; G), and alanine (Ala; A).

In some embodiments, the ELP can comprise the amino acid sequence (VPGXG (SEQ ID NO: 37))$_n$ WP or (VPGXG (SEQ ID NO: 37))$_n$ where n is about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 135, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, or 245.

In some embodiments, the ELP can comprise the amino acid sequence (VPGXG (SEQ ID NO: 37))$_n$ WP or (VPGXG (SEQ ID NO: 37))$_n$ where n is an integer of at least about 20, and each X is independently selected from valine, glycine, and alanine.

In some embodiments, the ELP can comprise the amino acid sequence (VPGXG (SEQ ID NO: 37))$_n$ WP or (VPGXG)$_n$ where each X is independently selected from valine, glycine, and alanine such that the Xs are Val:Gly:Ala in a 5:3:2 ratio. For exemplary purposes only, to illustrate the ratio of Val:Gly:Ala in some embodiments of the composition, where n is 20, ten (10) of the Xs would be selected to be valine, six (6) of the Xs would be selected to be glycine, and four (4) of the Xs would be selected to be alanine.

In some embodiments, the ELP can comprise the amino acid sequence (VPGXG (SEQ ID NO: 37))$_n$ WP or (VPGXG (SEQ ID NO: 37))$_n$ where n is about 20, 40, 80, 150, or 160, and where each X is independently selected from valine, glycine, and alanine such that the Xs are Val:Gly:Ala in a 5:3:2 ratio. In some embodiments, the ELP having Xs that are Val:Gly:Ala in a 5:3:2 ratio can comprise the amino acid sequence of SEQ ID NO: 22.

In some embodiments, the ELP can comprise the amino acid sequence (VPGXG (SEQ ID NO: 37))$_n$ WP or (VPGXG (SEQ ID NO: 37))$_n$ where each X is independently selected from valine, glycine, and alanine such that the Xs are Val:Gly:Ala in a 3:1:1 ratio. For exemplary purposes only, to illustrate the ratio of Val:Gly:Ala in some embodiments of the composition, where n is 5, three (3) of the Xs would be selected to be valine, one (1) X would be selected to be glycine, and one (1) X would be selected to be alanine.

In some embodiments, the ELP can comprise the amino acid sequence (VPGXG (SEQ ID NO: 37))$_n$ WP or (VPGXG (SEQ ID NO: 37))$_n$ where n is about 20, 40, 80, 150, or 160, and where each X is independently selected from valine, glycine, and alanine such that the Xs are Val:Gly:Ala in a 3:1:1 ratio.

In some embodiments, the ELP can comprise the amino acid sequence (VPGXG (SEQ ID NO: 37))$_n$ WP or (VPGXG (SEQ ID NO: 37))$_n$ where each X is independently selected from valine, glycine, and alanine such that the Xs are Val:Gly:Ala in a 1:7:8 ratio. For exemplary purposes only, to illustrate the ratio of Val:Gly:Ala in some embodiments of the composition, where n is 16, one (1) X would be selected to be valine, seven (7) of the Xs would be selected to be glycine, and eight (8) of the Xs would be selected to be alanine.

In some embodiments, the ELP can comprise the amino acid sequence (VPGXG (SEQ ID NO: 37))$_n$ WP or (VPGXG (SEQ ID NO: 37))$_n$ where n is about 20, 40, 80, 150, or 160, and where each X is independently selected from valine, glycine, and alanine such that the Xs are Val:Gly:Ala in a 1:7:8 ratio. In some embodiments, the ELP having Xs that are Val:Gly:Ala in a 1:7:8 ratio can comprise the amino acid sequence of SEQ ID NO: 23.

In some embodiments, the ELP can be an ELP having the amino acid sequence of SEQ ID NO: 22. In some embodiments, the ELP can be an ELP having the amino acid sequence of SEQ ID NO: 23.

In some embodiments, the ELP is an ELP as described in U.S. Patent Application Publication No. 2005/0255554 of A. Chilkoti, which is incorporated herein by this reference.

In some embodiments, the compound of the presently-disclosed subject matter can include the amino acid sequence of SEQ ID NO: 24. In some embodiments, the compound of the presently-disclosed subject matter can include the amino acid sequence of SEQ ID NO: 25. In some embodiments, the compound of the presently-disclosed subject matter can include the amino acid sequence of SEQ ID NO: 26. In some embodiments, the compound of the presently-disclosed subject matter can include the amino acid sequence of SEQ ID NO: 27. In some embodiments, the compound of the presently-disclosed subject matter can include the amino acid sequence of SEQ ID NO: 28. In some embodiments, the compound of the presently-disclosed subject matter can include the amino acid sequence of SEQ ID NO: 29. In some embodiments, the compound of the presently-disclosed subject matter can include the amino acid sequence of SEQ ID NO: 30. In some embodiments, the compound of the presently-disclosed subject matter can include the amino acid sequence of SEQ ID NO: 31. In some embodiments, the compound of the presently-disclosed subject matter can include the amino acid sequence of SEQ ID NO: 32. In some embodiments, the compound of the presently-disclosed subject matter can include the amino acid sequence of SEQ ID NO: 33. In some embodiments, the compound of the presently-disclosed subject matter can include the amino acid sequence of SEQ ID NO: 34. In some embodiments, the compound of the presently-disclosed subject matter can include the amino acid sequence of SEQ ID NO: 35. In some embodiments, the compound of the presently-disclosed subject matter can include the amino acid sequence of SEQ ID NO: 36. In some embodiments, the compound of the presently-disclosed subject matter can include the amino acid sequence of SEQ ID NO: 37.

As will be recognized by those skilled in the art upon studying the present document, with reference to the specific examples of CPPs and ELPs that can be used in accordance with the presently-disclosed subject matter, one or more amino acids can be added to and/or one or more amino acids can be removed from and/or conservative substations of one or more amino acids can be made as compared to the exemplary sequences set forth herein to obtain additional embodiments of the presently-disclosed subject matter. With regard to removing and/or making a conservative substitution of one or more amino acids relative to the specific examples of CPPs and ELPs as set forth herein, consideration to cell binding efficacy, and aggregation efficacy should be considered.

A "conservative substitution" is a substitution of an amino acid residue with a functionally similar residue. Examples of conservative substitutions include the substitution of one non-polar (hydrophobic) residue such as isoleucine, valine, leucine or methionine for another; the substitution of one charged or polar (hydrophilic) residue for another such as between arginine and lysine, between glutamine and asparagine, between threonine and serine; the substitution of one basic residue such as lysine or arginine for another; or the substitution of one acidic residue, such as aspartic acid or glutamic acid for another; or the substitution of one aromatic residue, such as phenylalanine, tyrosine, or tryptophan for another.

As will be recognized by those skilled in the art upon studying the present document, compounds as described herein can be made using standard molecular biology techniques.

The present inventors have shown, for example, that penetratin-ELP and the Tat-ELP inhibited adhesion, spreading, and migration of MDA-MB-231 breast cancer cells, SKOV-3 ovarian cancer cells and SK-MEL-2 melanoma cells.

The present invention further includes methods of inhibition comprising the use of polypeptides or compounds of the present invention. Table 2, below shows that inhibition of cell adhesion is cell line and CPP-ELP dependent. More specifically, Table 2 indicates that the $IC_{50}$ is the concentration of each polypeptide needed to prevent attachment of 50% of the plated cells. Tat-ELP, MTS-ELP and Antp-ELP polypeptides were shown to effectively prevent attachment in ovarian, melanoma and breast cancer cell lines, with Tat-ELP being the most efficient in all cell lines. Other polypeptides like Bac-7-ELP, Trans-ELP and pVEC-ELP are tested for their ability to prevent cell adhesion.

TABLE 2

| | | $IC_{50}$ of Different Polypeptides (μM) | | | | | |
|---|---|---|---|---|---|---|---|
| Cell Name | Cell Type | Tat-ELP | Antp-ELP | MTS-ELP | Bac-7-ELP | Trans-ELP | pVEC-ELP |
| SKOV-3 | Ovarian | 0.125 | 1.5 | 10 | nd* | nd* | nd* |
| SKMEL-2 | Melanoma | 0.015 | 1 | 10 | nd* | nd* | nd* |
| MDA | Breast | 0.5 | 1 | nd* | nd* | nd* | nd* |

*nd—not determined

Therefore, the present inventors have designed a system to achieve maximum cell adhesion inhibition for a particular cell line, including those for use with CPP-ELPs of the present invention. This method allows for efficient determination of CPP-ELPs in connection with inhibition of specific cancer cells.

Thus, additional embodiments of the present invention are novel classes of anti-adhesion polypeptides (compounds of the present invention), which are capable of inhibiting adhesion, spreading, and migration of cancer. In some embodiments, the compounds of the present invention are capable of inhibiting adhesion, spreading, and migration of cancer in a subject. Further embodiments of the present invention are methods of inhibiting the progression of tumors comprising administering the compounds of the present invention to a subject.

As used herein, the term "subject" includes both human and animal subjects. Thus, veterinary therapeutic uses are provided in accordance with the presently disclosed subject matter. As such, the presently disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

In some embodiments a CPP-ELP can be formulated by purifying the polypeptide from cultured bacterial cells grown in culture flasks or a bioreactor. Once purity of the polypeptide agent is insured, it will be formulated for injection by dissolving it in the appropriate amount of physiological saline to produce an injection of the proper dose and volume for administration, which can vary depending on the administration route used as outlined herein.

Conventional methods, known to those of ordinary skill in the art of medicine, can be used to administer effective amounts of the compound in a suitable formulation to a subject. Suitable methods for administering embodiments of the compound of the present invention in accordance with the methods of the present invention include but are not limited to systemic administration, parenteral administration (including intravascular, intramuscular, intraarterial, intraperitoneal administration), oral delivery, buccal delivery, subcutaneous administration, inhalation, intratracheal installation, surgical implantation, transdermal delivery, local injection, and hyper-velocity injection/bombardment.

The particular mode of drug administration used in accordance with the methods of the present invention depends on various factors, including but not limited to the severity of the condition to be treated.

The term "effective amount" is used herein to refer to an amount of the compound sufficient to produce a measurable biological response. Actual dosage levels of the compound in an appropriate formulation can be varied so as to administer an amount of the compound that is effective to achieve the desired response for a particular subject and/or application. The selected dosage level will depend upon a variety of factors including the route of administration, combination with other drugs or treatments, severity of the condition being treated, and the physical condition and prior medical history of the subject being treated. Preferably, a minimal dose is administered, and dose is escalated in the absence of dose-limiting toxicity to a minimally effective amount. Determination and adjustment of an effective dose, as well as evaluation of when and how to make such adjustments, are known to those of ordinary skill in the art of medicine and can be determined in a particular case by one skilled in the art using only routine experimentation. Dosing can being at levels needed to achieve plasma concentration of the compound in substantially the ranges as set forth in Table 2, e.g., equating to a dose of about 1 mg polypeptide/kg of body weight, up to about 200 to about 500 mg polypeptide/kg of body weight.

EXAMPLES

The following Examples are presented for exemplary purposes. Accordingly, they are to be construed as showing embodiments of the present invention and are not to be construed as being limiting thereof.

The Examples demonstrate that the exemplary compounds of the present invention are capable of inhibiting adhesion, spreading, invasion and migration of breast cancer cells, melanoma cells and ovarian cancer cells.

Example 1

Breast Cancer Metastasis

This Example helps characterize the mechanism of CPP-ELP action:

Extracellular matrix protein adhesion assay. The ability of CPP-ELP to modulate adhesion and spreading of MDA-MB-231 breast cancer cells to a substrate coated with specific extracellular matrix (ECM) molecules (fibronection, laminin, and collagen IV).

Cell surface receptor assay. In order to elucidate the nature of the cell surface molecules involved, the effect of proteolytic digestion of specific cell surface molecules on the ability of CPP-ELP to bind to MDA-MB-231 cells.

Immunoprecipitation of cell surface proteins. Using the results from the cell surface receptor assay, any protease that demonstrates an effect on CPP-ELP binding used in an immunoprecipitation assay to identify the specific proteins released from the membrane that are important in CPP-ELP binding.

Effect of CPP-ELP size on attachment inhibition. Experiments can demonstrate whether or not specific proteins are involved in CPP-ELP inhibition. If no proteins are involved in CPP-ELP inhibition, then it is likely that CPP-ELP works by simply coating the cell surface and blocking many important cell to ECM interactions. CPP-ELPs of different molecular weights can be used to determine the size dependence of cell adhesion inhibition. This hypothesis indicates that a larger CPP-ELP may be a more potent inhibitor than a smaller one.

Example 2

Metastasis of Melanoma Cells

To test the ability of CPP-ELP to reduce the metastatic properties of melanoma cells in vivo the following experiments may be done:

Experimental metastasis assay. Briefly, immunodeficient mice are given an i.v. injection of SK-MEL-2 melanoma cells mixed with various concentrations of CPP-ELP. Two weeks after inoculation of tumor cells, the mice are sacrificed and the number of tumor colonies in the lung, spleen, and kidneys will be recorded.

Spontaneous metastasis assay. In the spontaneous metastasis assay, mice are injected subcutaneously in the hind limb with melanoma cells to form a primary tumor. Polypeptides are administered i.v. on various days after tumor inoculation, and metastasized tumor colonies in the lung, spleen, and kidneys will be counted four weeks later.

Example 3

Breast Cancer Metastasis

When breast carcinoma remains confined to breast tissue, cure rates exceed 90%. However, cells from a primary tumor can spread to distant tissues via blood vasculature or lymphatics and form secondary tumors, or metastases. As cells spread, long-term survival decreases dramatically depending upon the extent of and the sites of colonization. Metastases in visceral organs and brain are the most life-threatening, and they are the direct cause of mortality in most breast cancer patients, with 5-year survival rates usually less than 20%. Therefore, efforts to understand and prevent the metastatic process of breast cancer cells are of tremendous clinical importance.

In Vitro Cell Attachment and Spreading: The present inventors have shown that immediately after incubation with MCF-7 breast cancer cells, CPP-ELP based polypeptides are localized to the plasma membrane (30). Therefore, without being bound by theory, it appears that the polypeptides of the present invention, with such cell membrane binding properties, may affect the cell's ability to attach to a substrate. In order to investigate CPP-ELPs for the ability to inhibit attachment, an in vitro cell attachment assay was used. MDA-MB-231 human breast cancer cells were incubated in suspension ($5 \times 10^4$ cells in 1 ml) with the CPP-ELPs for 10 minutes. 24 well tissue culture dishes were coated for 2 h with a 2% gelatin solution, and the cell/protein mixture was then plated and incubated for 3 h to allow cell attachment. After the attachment period, non-adherent cells were collected by removing the media and rinsing the wells gently with PBS. The floating fraction was counted using a Coulter counter, and the results are shown in FIG. 1.

During the 3 h attachment period, more than $4 \times 10^4$ of the $5 \times 10^4$ untreated MDA-MB-231 cells plated attached to the substrate (as shown at zero polypeptide concentration in FIG. 1). The ELP polypeptide, which has no CPP to facilitate cell binding, showed no inhibition of cell attachment at any concentration tested (not shown). In contrast, Pen-ELP showed a concentration dependent inhibition of MDA-MB- 231 attachment, with complete inhibition observed at 5 µM Pen-ELP. Tat-ELP inhibited cell attachment even more efficiently, with a maximum inhibition occurring at only 1 µM. The inhibition of attachment was not simply a property of the CPP peptide, since the 16 aa penetratin peptide alone had no effect on cell attachment (data not shown). These results show that both the CPP and ELP are required for attachment inhibition.

Figure 2:
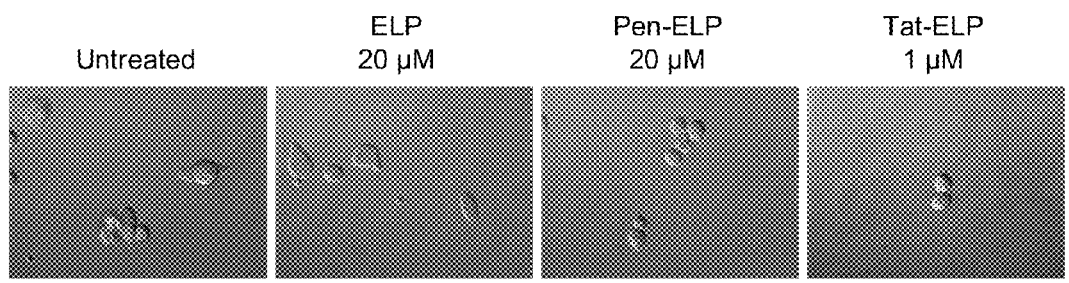
FIG. 2 is a set of photographs showing the spreading of MDA-MB-231 onto coverslips. Cells were treated in suspension with CPP-ELP at the indicated concentration and plated onto serum coated coverslips. Images were collected 4 h after plating using a Zeiss Axiovert DIC microscope with a 40× oil immersion objective.

In addition to inhibiting attachment of the cells to the substrate, the CPP-ELPs also inhibited the spreading of any cells that did attach. MDA-MB-231 cells were incubated as described above and plated on acid-washed coverslips coated with serum proteins. The coverslips were mounted onto slides 4 h after plating, and the cell morphology was observed using differential interference contrast (DIC) microscopy. FIG. 2 shows that 4 h after plating, control and ELP treated cells began to spread onto the coated coverslips. In contrast, the cells treated with Pen-ELP and Tat-ELP did not spread onto the substrate.

Figure 3:
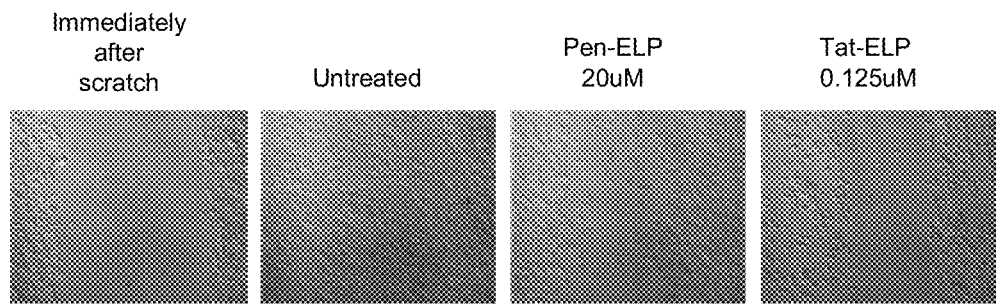
FIG. 3 is a set of photographs showing a scratch migration assay. MDA-MB-231 cells were grown to confluence and a scratch was made in the monolayer. Cells were treated with protein and allowed to migrate for 24 h. Migration was measured by collecting DIC images with at 10× magnification.

Cell Migration: Since the CPP-ELP molecules showed potent inhibition of cell attachment and spreading, we also assayed for their ability to inhibit cell migration. Migration is an important event in metastasis, in which the tumor cells must invade the layer of endothelial cells to gain access to the vascular circulation (31). We employed an in vitro scratch migration assay to test the ability of CPP-ELP to inhibit cell migration (32). Briefly, MDA-MB-231 cells were grown to confluence on acid-washed coverslips. A linear scratch was made, and the growth medium was replaced with media containing CPP-ELP. Cells were placed in the incubator for 24 h to allow migration of the cells into the newly generated scratch. Coverslips were mounted and cell migration was assessed by collecting DIC images of the scratched area. FIG. 3 shows that the scratch method removed all cells from the area of interest. 24 h later, control cells and ELP treated cells (ELP data not shown) completely filled the cleared area. Pen-ELP significantly reduced the ability of the MDA-MB-231 cells to migrate into the cleared area, and Tat-ELP produced an even stronger inhibition of migration.

Figure 4:
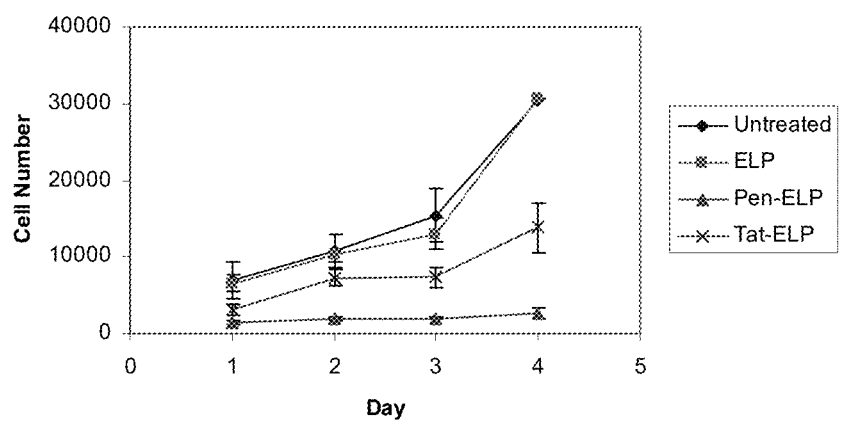
FIG. 4 a growth curve chart of MDA-MB-231 cells. Cells were treated with the indicated proteins before plating. Daily counts were made using a Coulter counter. Data represents an average of 3 independent experiments; bars, SE.

Cell Proliferation and Apoptosis: During the attachment and spreading assays, cells treated with CPP-ELP never attached or spread even 24 h after plating. We also examined the cells for a longer time period in order to determine if the cells were ever able to attach and to learn whether the cells can proliferate after attachment. To address this question, we monitored the growth of MDA-MB-231 cells after treatment with CPP-ELP. Cells were treated as described above and plated in serum-coated 24-well plates. Daily cell counts of the attached cells were made using a Coulter counter, and a growth curve (shown in FIG. 4) was generated. Control and ELP treated cells grew normally, making about 2 doublings during the 4 days of the assay. In contrast, cells treated with Pen-ELP showed no increase in cell number over 4 days, and Tat-ELP treated cells showed only a slight increase in number.

Inhibition of cell proliferation by CPP-ELP requires that the cells be treated while in suspension before plating. CPP-ELP shows no toxicity and no inhibition of growth when added to cells which are already attached to substratum (data not shown). These results suggest that inhibition of the proliferation of breast cancer cells by CPP-ELP treatment may be due to inhibition of cell attachment. This observation may be advantageous for the treatment of breast cancer metastasis, where the desired target cells are unattached and circulating.

The DIC images from the spreading assay revealed the presence of some apoptotic cells after treatment with CPP-ELP. After learning that CPP-ELP treated cells were not proliferating, we used an annexin binding assay to quantitate the extent of apoptosis after plating cells treated with CPP-ELP. MDA-MB-231 cells were treated and plated as above in 6-well plates. 5 h after plating, all cells (floating and attached) were collected by trypsinization, stained with FITC-annexin and propidium iodide (Molecular Probes, Eugene, Oreg.), and analyzed by flow cytometry. One event in the induction of apoptosis is the externalization of phosphatidyl serine to the outer leaflet of the plasma membrane. These cells stain with FITC-annexin, allowing quantitation of the amount of apoptotic cells. This assay also employs propidium iodide staining to elucidate the necrotic cells from the apoptotic cells.

Figure 5:
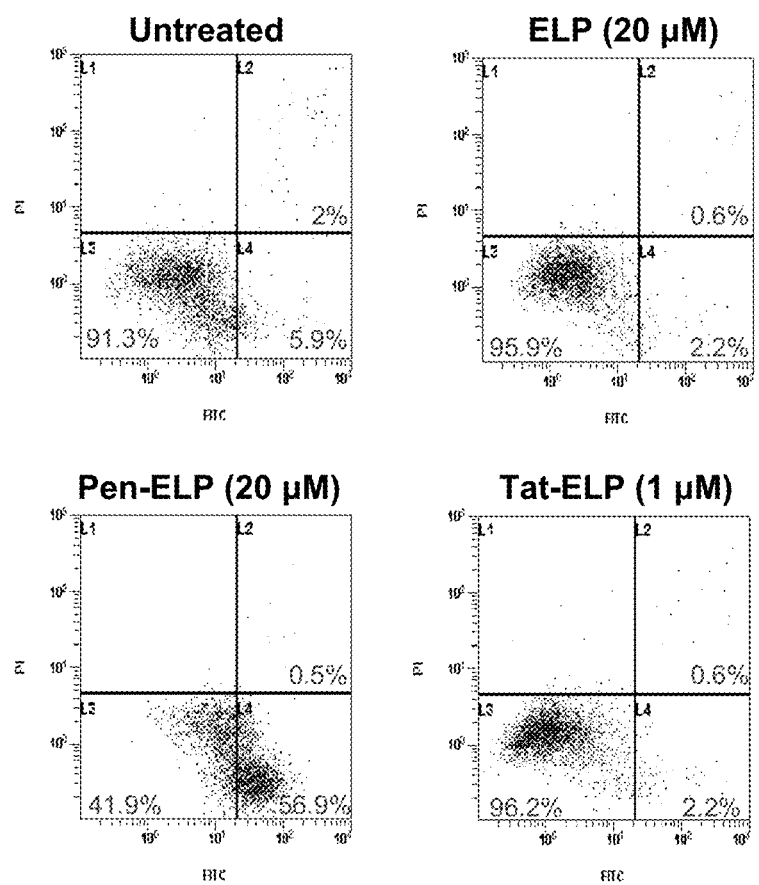
FIG. 5 is a set of charts showing apoptosis assay MDA-MB-231 cells treated with the indicated protein for 10 min and plated for 5 h. Cells were harvested and stained with FITC-annexin and propidium iodide, and fluorescence levels were determined by flow cytometry. Live cells are unstained by either agent and appear in L3. Apoptotic cells stain with FITC-annexin, but not with propidium iodide, and appear in L4. Cells in L2 stain with both agents and are necrotic.

When treated with ELP, cells were unaffected and gave similar results to control cells in the apoptosis assay (FIG. 5). Pen-ELP produced a strong effect on the MDA-MB-231 cells, inducing apoptosis in nearly 60% of the cells within the 5 h tested. In contrast, Tat-ELP had no apoptosis-inducing effect. Although Tat-ELP is a much more efficient inhibitor of cell attachment than Pen-ELP, Tat-ELP does not induce the apoptotic response nearly as extensively as Pen-ELP. This suggests that the two polypeptides may have different modes of action. This possibility will be addressed by the in vitro experiments proposed here.

In summary, this example shows that treatment of unattached breast cancer cells with CPP-ELPs inhibits their attachment, spreading, migration, and proliferation. Cells which are already attached are unaffected by CPP-ELP treatment, which is a promising fact for the future application of CPP-ELP Example 4

Melanoma Cancer Metastasis

In Vitro Cell Attachment and Spreading: In order to investigate CPP-ELPs for the ability to inhibit attachment of melanoma cells, an in vitro cell attachment assay similar to the one described above was used, and the results are shown in FIG. 6.

Figure 6:
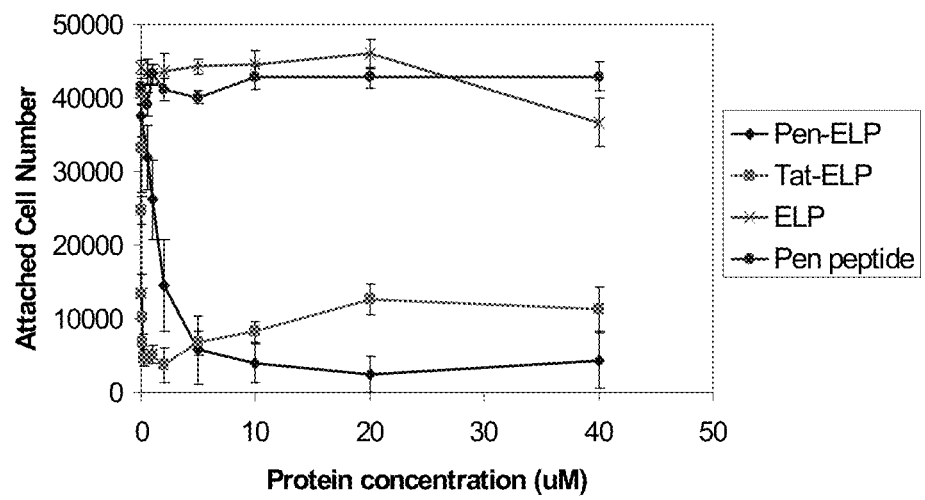
FIG. 6 is a chart showing in vitro attachment inhibition. SK-MEL-2 cells were exposed to polypeptides at the indicated concentration during a 3 h plating period. Floating cells were harvested and counted. Results represent the mean±SEM of at least 3 independent experiments.

During the 3 h attachment period, more than $4 \times 10^4$ of the $5 \times 10^4$ untreated SK-MEL-2 cells plated attached to the substrate (as shown at zero polypeptide concentration in FIG. 6). The ELP polypeptide, which has no CPP to facilitate cell binding, showed no inhibition of cell attachment at any concentration tested. In contrast, Pen-ELP showed a concentration dependent inhibition of SK-MEL-2 attachment, with complete inhibition observed at 20 µM Pen-ELP. Tat-ELP inhibited cell attachment even more efficiently, with a maximum inhibition occurring at only 2 µM. The inhibition of attachment was not simply a property of the CPP peptide, since the 16 aa penetratin peptide alone had no effect on cell attachment. These results show that both the CPP and ELP are required for attachment inhibition.

Figure 7:
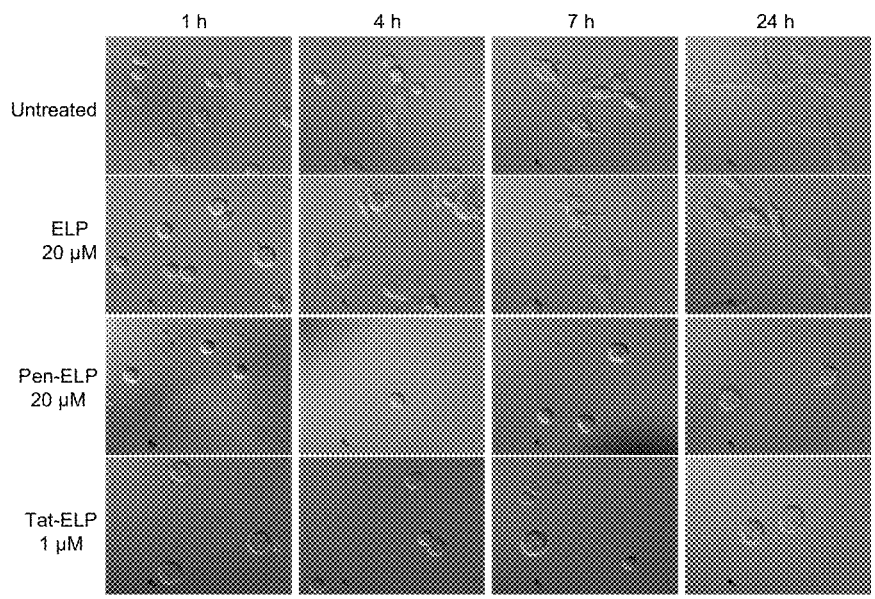
FIG. 7 is a set of photographs showing spreading of SK-MEL-2 onto coverslips. Cells were treated in suspension with CPP-ELP at the indicated concentration and plated onto acid-washed coverslips. Images were collected at the indicated times using a Zeiss Axiovert DIC microscope with a 40× oil immersion objective.

In addition to inhibiting attachment of the cells to the substrate, the CPP-ELPs also inhibited the spreading of any cells that did attach. SK-MEL-2 cells were incubated as described above and plated on acid-washed coverslips, and spreading was assayed using DIC microscopy. FIG. 7 shows that ELP does not affect cell spreading, but cells pretreated with Pen-ELP and Tat-ELP do not spread.

This spreading inhibition is not limited to cells plated on glass coverslips. Preliminary experiments with cells plated on fibronectin-coated cover-slips show that both Pen-ELP and Tat-ELP can inhibit SK-MEL-2 cell spreading onto a natural ECM substratum.

Figure 8:
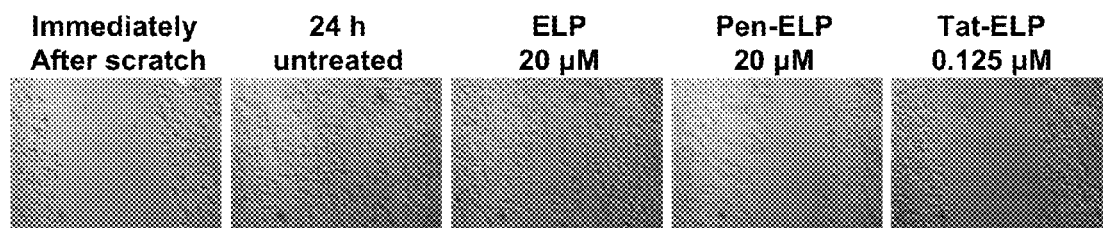
FIG. 8 is a set of photographs showing scratch migration assay. SK-MEL-2 cells were grown to confluence and a scratch was made in the monolayer. Cells were treated with protein and allowed to migrate for 24 h. Migration was measured by collecting DIC images with at 10× magnification.

Cell Migration: Since the CPP-ELP molecules showed potent inhibition of melanoma cell attachment and spreading, we also assayed for their ability to inhibit cell migration using the scratch migration assay described above. FIG. 8 shows that the scratch method removed all cells from the area of interest. 24 h later, control and ELP treated cells almost completely filled the cleared area. Pen-ELP significantly reduced the ability of the SK-MEL-2 cells to migrate into the cleared area, and Tat-ELP produced an even stronger inhibition of migration.

Figure 9:
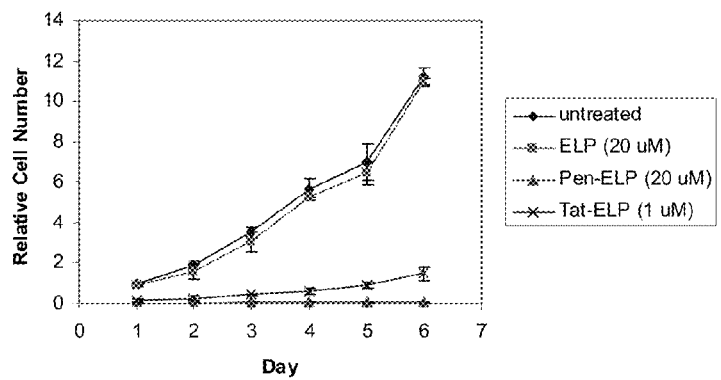
FIG. 9 is a chart showing a growth curve of SK-MEL-2 cells. Cells were treated with the indicated proteins before plating. Daily counts were made using a Coulter counter. Data represents an average of 3 independent experiments; bars, SE.

Cell Proliferation and Apoptosis: As with the SKOV-3 cells above, the SK-MEL-2 cells were not able to proliferate after plating in the presence of Pen-ELP or Tat-ELP (FIG. 9).

The DIC images from the spreading assay revealed the presence of some apoptotic cells after treatment with CPP-ELP. After learning that CPP-ELP treated cells were not proliferating, we used an annexin binding assay to quantitate the extent of apoptosis after plating cells treated with CPP-ELP. SK-MEL-2 cells were treated and plated as above in 6-well plates. 5 h after plating, all cells (floating and attached) were collected by trypsinization, stained with FITC-annexin and propidium iodide (Molecular Probes, Eugene, Oreg.), and analyzed by flow cytometry.

Figure 10:
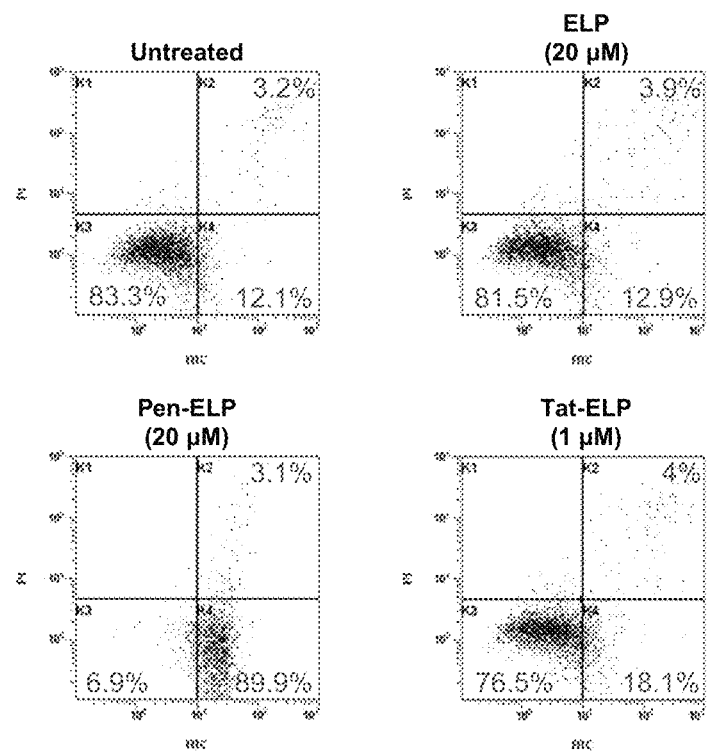
FIG. 10 is a set of photographs showing an apoptosis assay. SK-MEL-2 cells were treated with the indicated protein for 10 min and plated for 5 h. Cells were harvested and stained with FITC-annexin and propidium iodide, and fluorescence levels were determined by flow cytometry. Live cells are unstained by either agent and appear in K3. Apoptotic cells stain with FITC-annexin, but not with propidium iodide, and appear in K4. Cells in K2 stain with both agents and are necrotic.

When treated with ELP, cells were unaffected and gave similar results to control cells in the apoptosis assay (FIG. 10). Pen-ELP produced a strong effect on the SK-MEL-2 cells, inducing apoptosis in nearly 90% of the cells within the 5 h tested. Tat-ELP also induced apoptosis, but much less effectively than Pen-ELP. Although Tat-ELP is a much more efficient inhibitor of cell attachment than Pen-ELP, Tat-ELP does not induce the apoptotic response nearly as extensively as Pen-ELP. This suggests that the two polypeptides may have different modes of action. This possibility will be addressed by future in vitro experiments.

Example 5

Ovarian Cancer Metastasis

In North America and Europe, ovarian cancer is the fourth most common cause of cancer death among women and the prime cause of death among gynecological malignancies. Primary tumors from the ovaries tend to spread throughout the abdominal cavity and to other organs or areas of the body forming metastases. The main route of metastatic dissemination of epithelial ovarian cancer is by exfoliation of the tumor cells, which migrate, implant, and invade throughout the peritoneal cavity (33). The molecular mechanisms underlying this process are not well characterized, but it is clear that the attachment of cancer cells to the surfaces of other organs is one of the crucial steps in the development of metastatic ovarian cancer.

Figure 11:
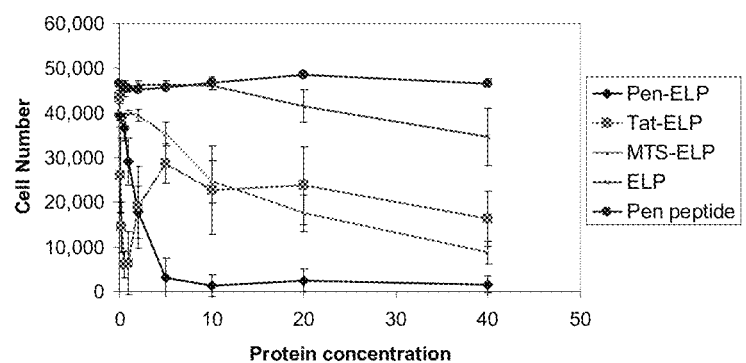
FIG. 11 is a chart showing in vitro attachment inhibition. SKOV-3 cells were exposed to polypeptides at the indicated concentration during a 3 h plating period. Floating cells were harvested and counted. Results represent the mean±SEM of at least 3 independent experiments.

In Vitro Cell Attachment and Spreading: The in vitro cell attachment assay described above was used to assay the ability of the CPP-ELPs to inhibit attachment of SKOV-3 ovarian cancer cells, and the results are shown in FIG. 1. During the 3 h attachment period, more than $4 \times 10^4$ of the $5 \times 10^4$ untreated cells plated attached to the substrate (as shown at zero polypeptide concentration in FIG. 11). The ELP polypeptide, which has no CPP to facilitate cell binding, showed no inhibition of cell attachment at any concentration tested. In contrast, Pen-ELP showed a concentration dependent inhibition of SKOV-3 attachment, with complete inhibition observed at 5 µM Pen-ELP. Tat-ELP inhibited cell attachment even more efficiently, with a maximum inhibition occurring at only 0.5 µM. The inhibition of attachment was not simply a property of the CPP peptide, since the 16 aa penetratin peptide alone had no effect on cell attachment. These results show that both the CPP and ELP are required for attachment inhibition.

Figure 12:
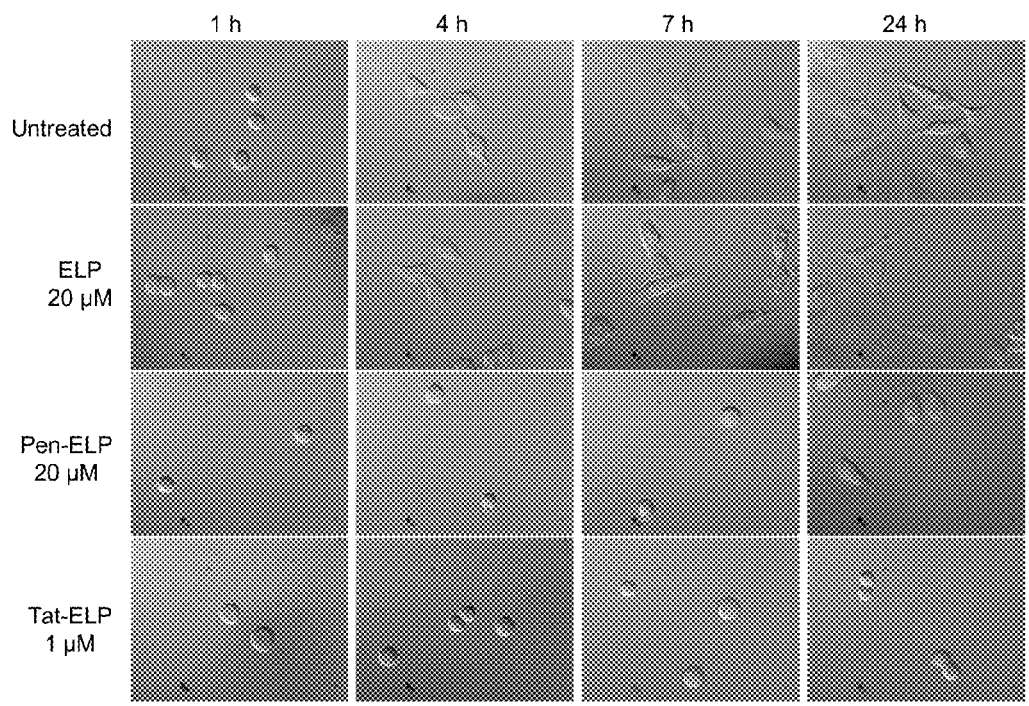
FIG. 12 is a set of photographs showing the spreading of SKOV-3 onto coverslips. Cells were treated in suspension with CPP-ELP at the indicated concentration and plated onto acid-washed coverslips. Images were collected at the indicated times using a Zeiss Axiovert DIC microscope with a 40× oil immersion objective.

In addition to inhibiting attachment of the cells to the substrate, the CPP-ELPs also inhibited the spreading of any cells that did attach. SKOV-3 cells were incubated as described above and plated on acid-washed coverslips. The coverslips were mounted onto slides at various time points after plating, and the cell morphology was observed using differential interference contrast (DIC) microscopy. FIG. 12 shows that 1 h after plating, control cells were attached but still rounded. Fewer cells were attached after treatment with Pen-ELP and Tat-ELP, but little morphological difference was apparent at this time point. 4 h after plating, control and ELP treated cells began to spread onto the glass coverslips, and even more extensive spreading was observed at 7 h and 24 h. In contrast, the cells treated with Pen-ELP and Tat-ELP never spread onto the substrate. This spreading inhibition is not limited to cells plated on glass coverslips. Preliminary experiments with cells plated on fibronectin-coated coverslips show that both Pen-ELP and Tat-ELP can inhibit SKOV-3 cell spreading onto a natural ECM substratum.

Figure 13:
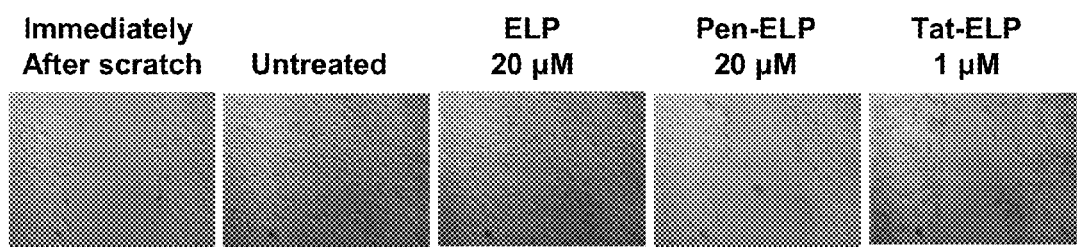
FIG. 13 is a set of photographs showing another scratch migration assay. SKOV-3 cells were grown to confluence and a scratch was made in the monolayer. Cells were treated with protein and allowed to migrate for 24 h. Migration was measured by collecting DIC images at 10× magnification.

Cell Migration: Since the CPP-ELP molecules showed potent inhibition of cell attachment and spreading, we also assayed for their ability to inhibit cell migration using the scratch migration assay described above. FIG. 13 shows that the scratch method removed all cells from the area of interest. 24 h later, control and ELP treated cells almost completely filled the cleared area. Pen-ELP significantly reduced the ability of the SKOV-3 cells to migrate into the cleared area, and Tat-ELP produced an even stronger inhibition of migration.

Figure 14:
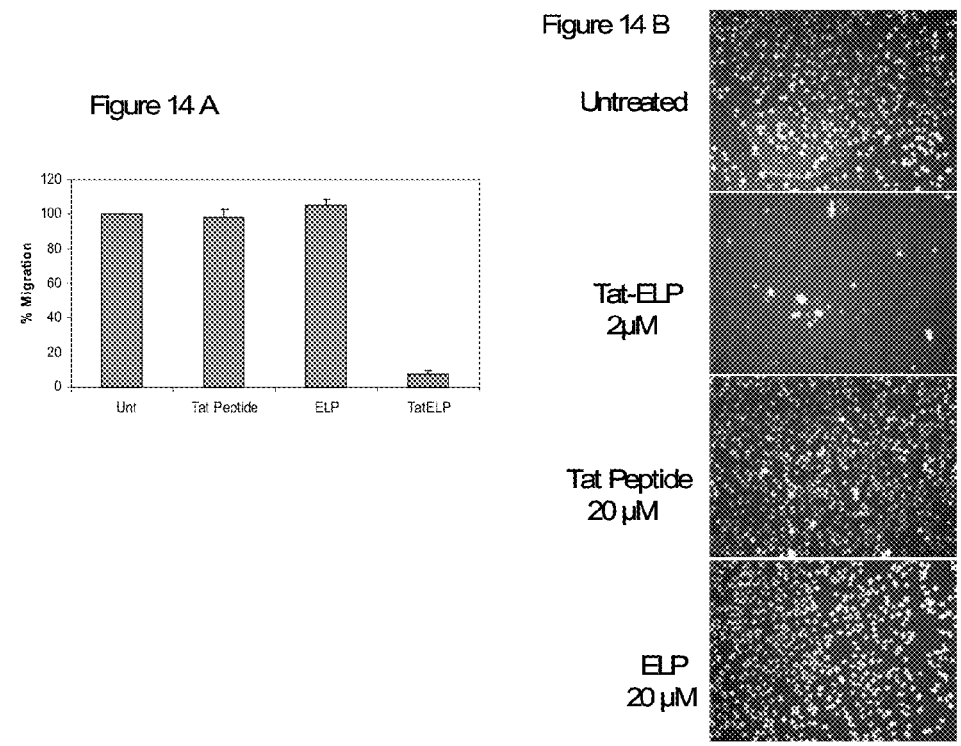
FIG. 14 is data related to a Boyden chamber assay.

In order to confirm the role of CPP-ELPs in preventing migration of SKOV-3 cells, a boyden chamber assay was performed (35). This assay involves a membrane with pore size of 8 µm. SKOV-3 cells are plated on one side of the membrane, and a chemoattractant (FBS) is placed on the opposite side of the membrane. The cells are allowed to migrate trough the pores toward the chemoattractant for h, and the cells which penetrated the membrane are quantified by cell counting and independently by Hoechst staining and fluorescence microscopy. As shown in FIG. 14 A, Tat-ELP treated cells did not migrate, while untreated, Tat peptide and ELP treated cells migrated across the membrane when counted under 20× magnification. This was also confirmed by Hoechst staining, which shows the number of cells migrated in FIG. 14 B. These experiments show that CPP-ELPs have a role in inhibiting migration. Serum starvation of cells overnight ruled out the fact that proliferation was a contributing factor in this assay.

Figure 15:
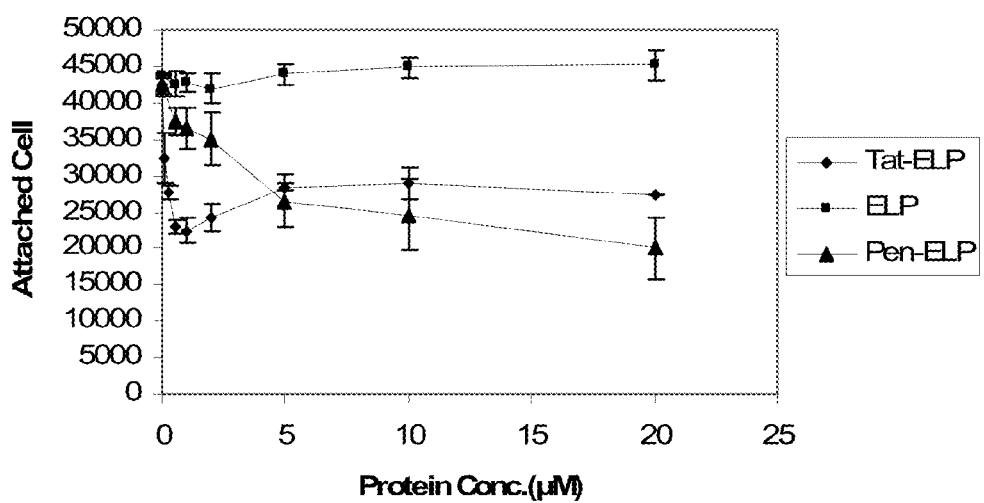
FIG. 15 is a chart that shows in vitro attachment inhibition on vitronectin coated plates. SKOV-3 cells were incubated with the different polypeptides at the indicated concentrations during a 3 h plating period on vitronectin coated plates. Floating cells were harvested and counted. Results represent the mean±SEM of at least 3 independent experiments.

Inhibition of SKOV-3 Attachment on Vitronectin: Cell migration is governed by a variety of factors, including cell surface adhesion receptor binding to extracellular matrix (ECM) proteins. One such matrix protein is vitronectin (VN). VN is a widely distributed high molecular weight glycoprotein found in most extracellular matrices and blood plasma that is known to promote cell adhesion and affect cell morphology, migration, differentiation, and cytoskeletal organization. FIG. 15 shows that attachment was inhibited nearly 50% on VN treated plates by different CPP-ELPs, while ELP had no such effect.

Cell Surface Receptor Assay: Cell migration is governed by a variety of factors, including cell surface adhesion receptor binding to extracellular matrix (ECM) proteins.

One such matrix protein is vitronectin (VN). VN is a widely distributed high molecular weight glycoprotein found in most extracellular matrices and blood plasma that is known to promote cell adhesion and affect cell morphology, migration, differentiation, and cytoskeletal organization. Cell migration is governed by a variety of factors, including cell surface adhesion receptor binding to extracellular matrix (ECM) proteins. One such matrix protein is vitronectin (VN). VN is a widely distributed high molecular weight glycoprotein found in most extracellular matrices and blood plasma that is known to promote cell adhesion and affect cell morphology, migration, differentiation, and cytoskeletal organization. Cell migration is governed by a variety of factors, including cell surface adhesion receptor binding to extracellular matrix (ECM) proteins. One such matrix protein is vitronectin (VN). VN is a widely distributed high molecular weight glycoprotein found in most extracellular matrices and blood plasma that is known to promote cell adhesion and affect cell morphology, migration, differentiation, and cytoskeletal organization. Since the action of CPP-ELPs is mediated via interaction with the various cell surface receptors on the cell membrane, we assumed that treatment of cells with the enzymes mentioned below may provide some information about the binding characteristics of the CPP-ELPs.

Figure 16:
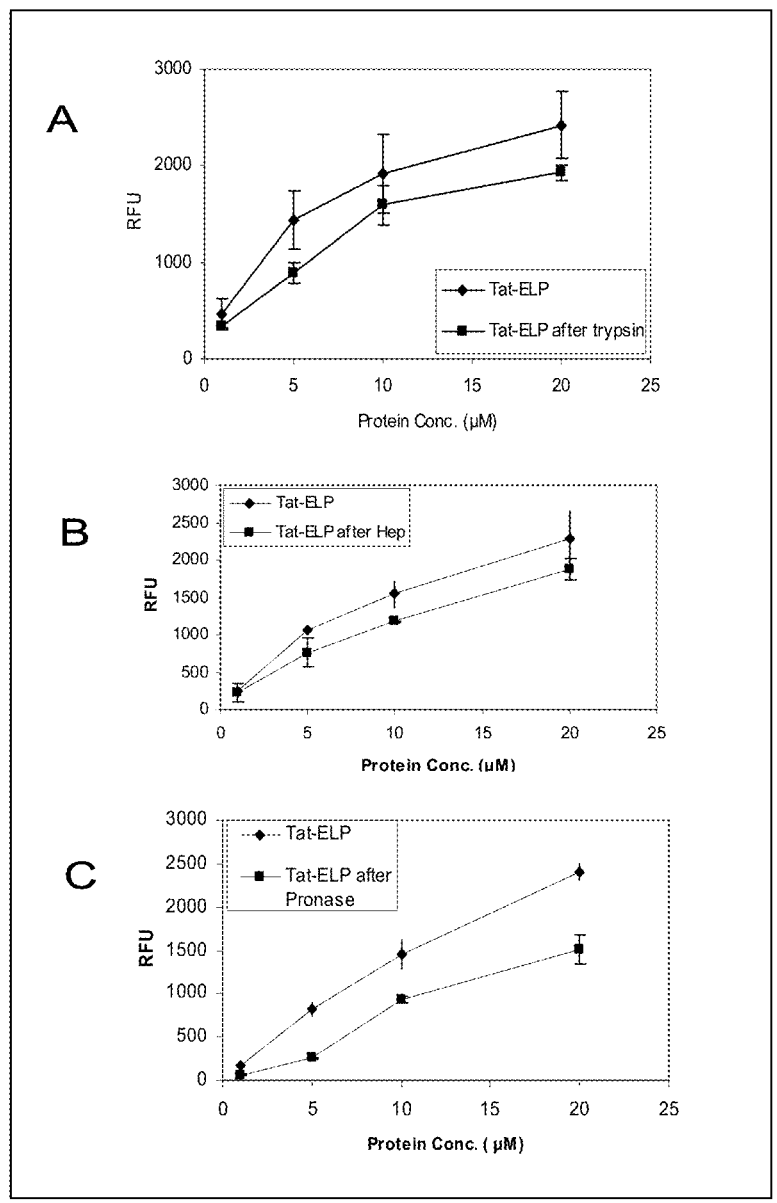
FIG. 16 illustrates a cell surface receptor assay. A. Trypsin treatment. Cells were briefly incubated with trypsin, washed and resuspended in PBS containing fluorescein-labeled polypeptide at various concentrations for 10-15 min. Binding of different polypeptides was measured by immediately analyzing cell fluorescence by flow cytometry. B. Heparanase treatment. Cells were briefly incubated with heparanase, washed and resuspended in PBS containing fluorescein-labeled polypeptide, and cell fluorescence was determined as described above. C. Pronase treatment. Cells were briefly incubated with pronase, washed and resuspended in PBS containing fluorescein-labeled polypeptide, and cell fluorescence was determined as described above.

Trypsin, Heparanase, and Pronase Treatment: Brief 3 min. incubation of cells with trypsin prior to polypeptide treatment showed nearly 20-40% decrease in Tat-ELP binding as compared to binding in normal cells (FIG. 16 A). Similarly, incubation of cells with heparanase (FIG. 16 B) and pronase (FIG. 16 C) for specified time periods caused ~20-25% and 40-70% decrease in the respective binding of Tat-ELP over the concentration range. Binding of ELP polypeptide did not differ significantly under different enzymatic conditions. These enzymes have been reported to digest various cell surface receptors such as heparin surface proteoglycans and glycoproteins which are involved in attachment and tumor metastases (36, 37). These results show that binding is decreased by the enzyme pretreatment and provide some information about the role of various cell surface receptors and their interaction with CPP-ELPs.

Figure 17:
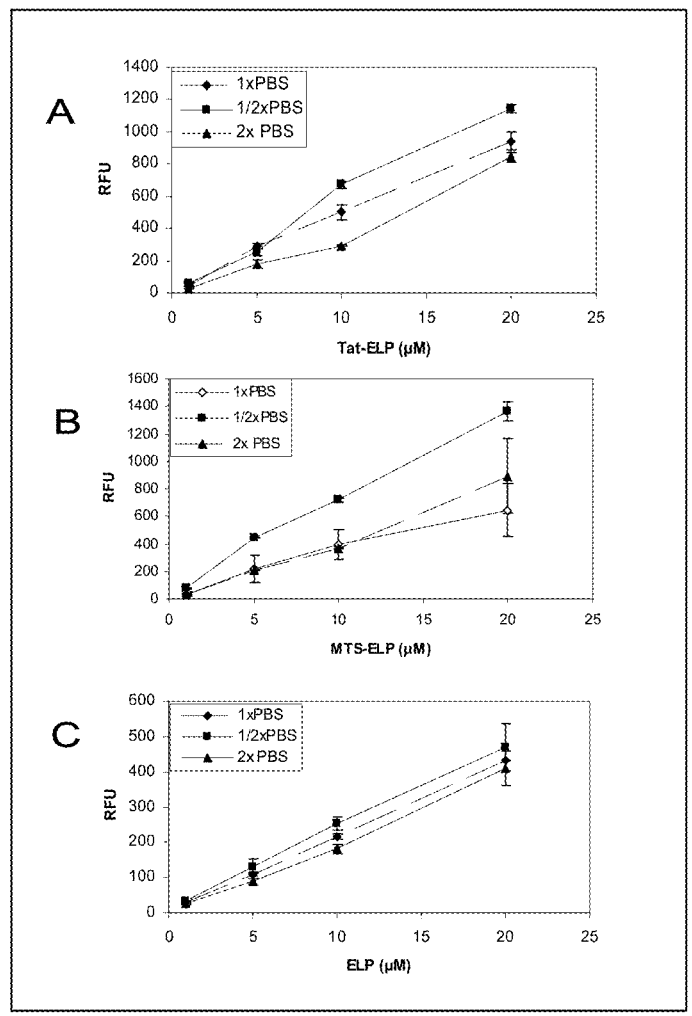
FIG. 17 is a set of tables showing binding at different ionic strengths. Cells were resuspended in ½×, 1× and 2×PBS and incubated with fluorescene labeled polypeptides in a concentration dependent manner for 10-15 min. and immediately run on flow cytometer.

Effect of Ionic Strength on Binding: It is important to explore the selective binding of CPP-ELPs to cell surfaces in greater detail, in particular with regard to ionic strength. Since the nature of the interaction between cell membrane and CPP-ELPs is ionic due to their charged nature, we tested the binding of different polypeptides at different ionic concentrations. The solution's ionic strength was varied by changing the concentration of NaCl in PBS from 0.5 M to 2 M. The binding experiment was performed in each PBS solution and compared to binding in standard PBS solution. It was observed that binding of Tat-ELP was enhanced by ~25-30% in ½ M PBS and reduced by ~18-40% in 2 M PBS when compared with binding of Tat-ELP in 1 M PBS (FIG. 17A). The binding of uncharged polypeptide ELP (17 C) did not show any significant difference at various PBS concentrations. This experiment demonstrates that the binding of the cationic peptide Tat to the cell membrane depends on the ionic composition of the media, with less ionic environment favoring more binding and vice versa.

Figure 18:
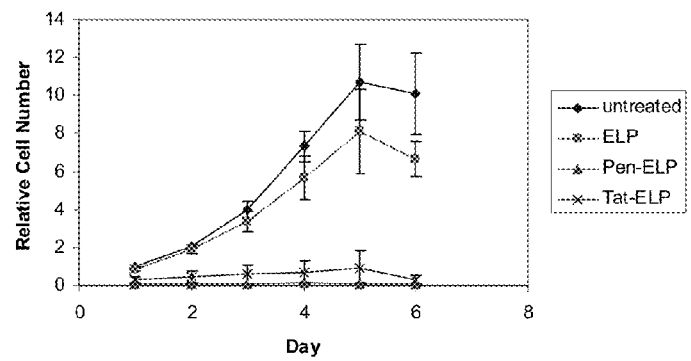
FIG. 18 is a chart showing a growth curve of SKOV-3 cells. Cells were treated with the indicated proteins before plating. Daily counts were made using a Coulter counter. Data represents an average of 3 independent experiments; bars, SE.

Cell Proliferation: During the attachment and spreading assays, cells treated with CPP-ELP never attached or spread even 24 h after plating. We also examined the cells for a longer time period in order to determine if the cells were ever able to attach in and to learn whether the cells can proliferate after attachment. To address this question, we monitored the growth of SKOV-3 cells after treatment with CPP-ELP. Cells were treated as described above and plated in 6-well plates. Daily cell counts of the attached cells were made using a Coulter counter, and a growth curve (shown in FIG. 18) was generated. Control and ELP treated cells grew normally, making 8 to 10 doublings during the 6 days of the assay. In contrast, cells treated with Pen-ELP and Tat-ELP showed no increase in cell number over 6 days.

Inhibition of cell proliferation by CPP-ELP requires that the cells be treated while in suspension before plating. CPP-ELP shows no toxicity and no inhibition of growth when added to cells which are already attached to substratum (data not shown). These results suggest that inhibition of the proliferation of ovarian cancer cells by CPP-ELP treatment may be due to inhibition of cell attachment. This observation may be advantageous for the treatment of ovarian cancer metastasis, where the desired target cells are unattached and circulating.

Figure 19:
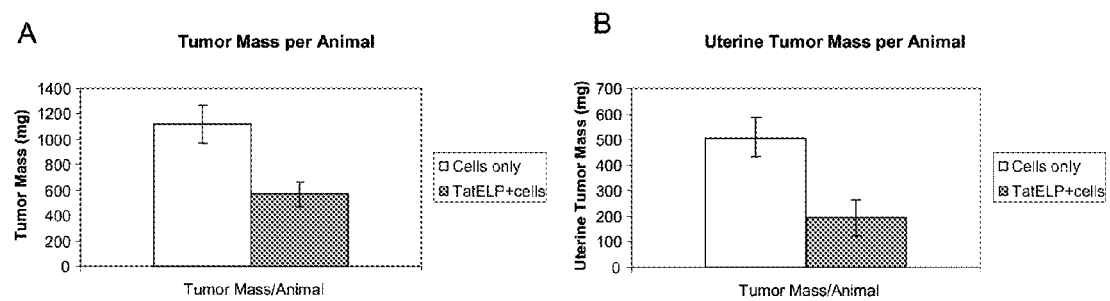
FIG. 19 is a set of charts showing an experimental metastases assay. BALB/C nude mice were given an i.p injection of SKVO-3 cells in PBS and SKOV-3 cells in 500 µM/mL Tat-ELP. The mice were sacrificed 17 days later and tumor mass per animal was recorded. A. Total tumor burden per animal in treated and untreated animals. B. Tumor burden recorded in uterus/fallopian tube of each animal. Bars; SD, n=5.

Ovarian Peritoneal Metastasis In Vivo: The most probable use for an anti-metastatic agent such as CPP-ELP will be at the time of surgical resection of the primary tumor in order to prevent the spread of micrometastases resulting from tumor cells that were loosened or not removed during the surgery. Therefore, in order to test the ability of CPP-ELP to inhibit metastasis in a clinically relevant setting, we used a rat ovarian metastasis model. In this assay, $75 \times 10^6$ SKOV-3 cells grown in culture were injected into the peritoneal cavity of athymic nude rats. The cells were premixed with the most efficient attachment inhibitor, Tat-ELP at a concentration of 500 µM, or with PBS control. After injection, metastases were allowed to develop for 17 days. The animals were sacrificed, and the peritoneal metastases were carefully dissected from the attached normal tissue. The weight of each tumor was measured. The tumor burden per animals is reported as the sum of all tumor nodules from the small and large intestine, omentum, spleen, diaphragm, fallopian tubes, and bladder. As shown in the FIG. 19 A, the tumor burden/animal in the Tat-ELP treated group was nearly 50% less than the control group. SKOV-3 ovarian cancer cells have a high tendency to metastasize to the uterus and fallopian tubes. Therefore, the uterine tumor mass per animal was compared in untreated and treated groups. As shown in FIG. 19 B, Tat-ELP treated animals showed nearly 60% reduction in uterine tumor mass as compared to untreated animals.

Figure 20:
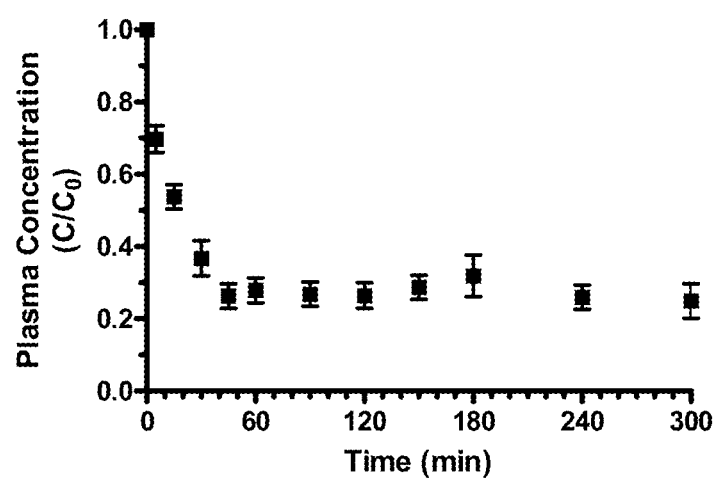
FIG. 20 is a chart showing mean of normalized plasma concentration-time profile of CPP-ELP after administration of a bolus IV injection. Plasma was diluted for fluorescence measurement of polypeptide concentration. Data are normalized to the initial concentration and plotted as mean±SE from three animals.

In vivo Plasma Concentrations of CPP-ELP1-H1: In order to assess the plasma kinetics of the CPP-ELP polypeptide in vivo, preliminary studies were performed in athymic rats. A fluorescently labeled polypeptide (CPP-ELP-fluorescein) was injected as a bolus in anesthetized rats. The plasma concentration of this polypeptide was measured for five hours as shown in FIG. 20. The plasma concentration of the polypeptide declined to about 30% of its initial value during the first 45-60 min after injection, then showed little further decline over the following 4 hours. The apparent volume of distribution for the distribution phase of the curve was 35.5±9.7 ml, which indicates that the volume is over three times the estimated plasma volume (~7% of 150 g rat). The relatively stable concentration of the agent after the first 45 minutes is likely due to the large molecular weight of the polypeptide, but may also be due to significant protein and cellular binding. Further characterization of the pharmacokinetic parameters and binding properties for several CPP-ELP polypeptides are planned in the future.

Because diagnosis of ovarian cancer occurs most often only after the disease has progressed, treatment is limited to surgical resection in combination with chemotherapy. It has been observed that an increased incidence of metastasis occurs after this surgical manipulation (38). Therefore, the development of an antimetastatic agent that could be administered at or before the time of surgery would reduce the chance of post-surgical metastases forming. Thus, embodiments of the present invention are non-toxic agents given as adjuvant therapy to patients at the time of surgery, and could complement chemotherapy to slow the spread of remaining cancerous cells. Our results have shown that treatment of unattached ovarian cancer cells with CPP-ELPs inhibits their attachment, spreading, migration, invasion and proliferation in vitro and peritoneal metastasis of ovarian cells in vivo. Therefore, CPP-ELP has potential in anti-metastatic therapy to improve the cure rate for surgically resected ovarian tumors.

Example 6

Test Regarding Present Invention and C6 Cell Proliferation

CPP-ELP-H1 is an effective inhibitor of breast cancer cell proliferation in vitro (see above), and its efficacy for breast cancer therapy in vivo is currently being established. However, malignant glioma is a cancer that is much more difficult to treat and with a much lower cure rate than breast cancer. Therefore, developmental therapeutics for malignant glioma is a field that could greatly benefit from the targeted approach applied with ELP technology. In order to examine the antiproliferative effects of the CPP-ELP-H1 polypeptides in glioma cells, C6 cells were exposed for 1 hour to 20 µM Bac-ELP1-H1 or Bac-ELP2-H1 at 37° C. or 42° C. one day after cell seeding. The polypeptides were washed away, and the cells were allowed to grow until day 3. Cell number was determined using the MTS assay. The resulting data show that the thermally sensitive peptide Bac-ELP1-H1 did not inhibit cell proliferation when cells were treated at 37° C. However, when cells were treated at 42° C., cell proliferation was inhibited by up to 60%.

The nonthermally responsive control, Bac-ELP2-H1, had no effect on C6 proliferation, and control polypeptides lacking the c-Myc inhibitory sequence (Bac-ELP1 or Bac-ELP2) did not have any effect on cell proliferation. These results suggest that the polypeptides exhibit an antiproliferative effect in C-6 cells, which can be further enhanced by hyperthermia.

Development of the C6 Gliobastoma Model: This study will utilize an intracerebral tumor-bearing rat model of glioma (C6). The rat glioma model is similar to human malignant glioma (glioblastoma multiforme) both histologically and in rapid proliferation. In a previous study, C6 gliomas were induced by intracranial injection of a suspension of C6 cells. The tumors were imaged sequentially with 3-D volume measurements generated by means of a clinical magnetic resonance imaging system (CMRI) and commercially available wrist coil. This study demonstrated that gliomas can be reliably grown in rats using the C6 cell line, and MRI imaging is an effective means of monitoring tumor progression.

Heating intracerebral C6 tumors using infrared light: Our previous studies in subcutaneous tumor models have used infrared (IR) light generated by the Laser Systim 540® (Mettler Electronics) to heat the tumors. This method is preferred over more primitive techniques such as water bath immersion because the heat can be applied to a more concentrated area and without physical contact with the animal. In order to test the effectiveness of this method in the glioma model, three representative C6 tumors grown in rat brains were used in a heating trial. The tumor core reached the desired hyperthermia temperature within 15 minutes of the start of illumination, and the temperature remained in the desired hyperthermia range for the remainder of an hour. This experiment demonstrates that the use of IR light is a feasible and minimally invasive method of heating intracerebral C6 tumors.

Following the heating period, the rats were exsanguinated and perfused with 4% paraformaldehyde, and the brains were removed, sectioned, and stained with hematoxylin and eosin (H&E). All three animals developed tumors, and the tumors were highly vascularized. Additionally, the tumor tissue displayed rosettes that are characteristic of glioblastoma. The area around the tumor appeared as normal neural tissue, and no acute damage from the hyperthermia treatment was apparent.

Imaging Intratumor Distribution of the Therapeutic Peptide Carrier: Previous studies have shown that ELP accumulation in tumor vasculature or interstitium can be increased with focused hyperthermia. However, entry of the ELP carrier into the tumor cells, a property necessary for effective drug delivery, has never been demonstrated. The use of CPPs fused to the ELP carrier may enhance its uptake into the tumor cells. To test the ability of the Bac and Tat CPPs to enhance ELP uptake into tumor cells in vivo, rats bearing C6 tumors were intravenously injected with Rhodamine-labeled Bac-ELP1-H1 or Tat-ELP1-H1. One tumor was heated for 60 min. using IR illumination as described above. 1 min prior to euthanasia, high molecular weight (500 kDa) FITC-dextran was injected IV in order to mark the perfused vessels. The tumors were removed, rapidly frozen, and sectioned using a cryomicrotome. Tumor sections were fixed and stained with Hoescht 33342 and imaged using a Nikon fluorescence microscope with a CoolSnap CCD camera. Bac-ELP1-H1 is present not only in the tumor blood vessels, but it also escaped circulation and entered the tumor cells. Below the $T_t$, Bac-ELP1-H1 is present in the cytoplasm of the tumor cells. Above the $T_t$, the polypeptide can also be detected in the tumor cell nuclei. This is consistent with the localization of the polypeptide in cultured cells. Tat-ELP1-H1 is also able to escape the tumor vasculature and enter the tumor cells. Tat-ELP1-H1 was present in the cell cytoplasm at temperature above and below the $T_t$, again consistent with its subcellular localization in vitro. Thus, this Example indicates a direct observation that ELP aided by a CPP can escape the tumor vasculature and enter the tumor cells.

Tumor Size Reduction by the ELP-delivered c-Myc Inhibitory Peptide: In order to assess the ability of the ELP-delivered c-Myc inhibitory peptide to reduce tumor size, rats bearing 2 C6 tumors implanted subcutaneously in the rats' back were treated by IV injection of Bac-ELP1-H1 (130 mg/kg) or saline control, and one tumor was heated for 60 min using the IR heating method. Bac-ELP1-H1 was used in this study because it was found to be the most potent inhibitor of cell proliferation in vitro (unpublished data). Following treatment, the animals were returned to their cages, and tumor size and body weight was monitored for 19 days. In saline treated rats, the tumors proliferated rapidly up to a volume of 4000 mm$^3$, and hyperthermia alone had no effect on tumor size. In contrast, the tumors in animals treated with Bac-ELP1-H1 began to shrink 4 days after treatment, and were nearly undetectable at day 19. Both the heated and unheated tumors in the treated animals were eventually cleared after treatment, but the heated tumor was reduced slightly faster. This indicates that at a dose of 130 mg/kg, Bac-ELP-H1 is potent enough to completely eliminate C6 tumor growth. Further studies are underway at lower doses in order to look for a more significant difference between the heated and unheated tumors. No body weight loss, injection site reactions, or gross signs of toxicity were observed.

Rats were sacrificed on Day 19 after implantation, and tumors were removed and weighed. Untreated animals had tumors weighing approximately 2 g, and there was no significant difference between heated and unheated tumors. Animals treated with Bac-ELP1-H1, however, had significantly smaller tumors, with an average weight of less than 300 mg. No significant difference was seen between heated and unheated Bac-ELP1-H1 treated tumors, again supporting the evidence that 130 mg/kg is a sufficient dose to cause complete tumor regression even without hyperthermia.

Evaluation of Toxicity of the Bac-ELP1-H1 Polypeptide: In addition to monitoring tumor size during the above experiment, rats were monitored for weight loss or other signs of acute toxicity due to the Bac-ELP1-H1 treatment. The average body weight of the animals did not differ between saline and Bac-ELP1-H1 treated groups, and no weight loss was observed following Bac-ELP1-H1 treatment. In addition, all major organs were removed and weighed at necropsy on Day 19. No significant difference was seen in organ weights from animals treated with saline control and animals treated with Bac-ELP1-H1. Also, no hair loss or injection site reactions were observed, and no other signs of toxicity were noticed.

Throughout this application, and specifically, below, various references are mentioned. All references are incorporated herein by reference in their entirety and should be considered to be part of this application.

REFERENCES

1. Haass, N. K., Smalley, K. S., Li, L., and Herlyn, M. Adhesion, migration and communication in melanocytes and melanoma. Pigment Cell Res, 2005; 18: 150-9.
2. McGary, E. C., Lev, D. C., and Bar-Eli, M. Cellular adhesion pathways and metastatic potential of human melanoma. Cancer Biol Ther, 2002; 1: 459-65.
3. Satyamoorthy, K. and Herlyn, M. Cellular and molecular biology of human melanoma. Cancer Biol Ther, 2002; 1: 14-7.
4. Aota, S., Nagai, T., and Yamada, K. M. Characterization of regions of fibronectin besides the arginine-glycine-aspartic acid sequence required for adhesive function of the cell-binding domain using site-directed mutagenesis. J Biol Chem, 1991; 266: 15938-43.
5. Yamada, K. M. Adhesive recognition sequences. J Biol Chem, 1991; 266: 12809-12.
6. Iwamoto, Y., Robey, F. A., Graf, J., Sasaki, M., Kleinman, H. K., Yamada, Y., and Martin, G. R. YIGSR, a synthetic laminin pentapeptide, inhibits experimental metastasis formation. Science, 1987; 238: 1132-4.
7. Komazawa, H., Saiki, I., Nishikawa, N., Yoneda, J., Yoo, Y. C., Kojima, M., Ono, M., Itoh, I., Nishi, N., Tokura, S., and et al. Inhibition of tumor metastasis by Arg-Gly-Asp-Ser (RGDS) peptide conjugated with sulfated chitin derivative, SCM-chitin-RGDS. Clin Exp Metastasis, 1993; 11: 482-91.
8. Yamamoto, Y., Tsutsumi, Y., and Mayumi, T. Molecular design of bioconjugated cell adhesion peptide with a water-soluble polymeric modifier for enhancement of antimetastatic effect. Curr Drug Targets, 2002; 3: 123-30.
9. Mu, Y., Kamada, H., Kaneda, Y., Yamamoto, Y., Kodaira, H., Tsunoda, S., Tsutsumi, Y., Maeda, M., Kawasaki, K., Nomizu, M., Yamada, Y., and Mayumi, T. Bioconjugation of laminin peptide YIGSR with poly(styrene co-maleic acid) increases its antimetastatic effect on lung metastasis of B16-BL6 melanoma cells. Biochem Biophys Res Commun, 1999; 255: 75-9.
10. Allen, T. M. Liposomal drug formulation: rationale for development and what we can expect in the future. Drugs, 1998; 56: 747-56.
11. Kissel, M., Peschke, P., Subr, V., Ulbrich, K., Schuhmacher, J., Debus, J., and Friedrich, E. Synthetic macromolecular drug carriers: biodistribution of poly[(N-2-hydroxypropyl)methacrylamide] copolymers and their accumulation in solid rat tumors. PDA J Pharm Sci Technol, 2001; 55: 191-201.
12. Meyer, D. E. and Chilkoti, A. Purification of recombinant proteins by fusion with thermally-responsive polypeptides. Nat Biotechnol, 1999; 17: 1112-5.
13. Meyer, D. E., Trabbic-Carlson, K., and Chilkoti, A. Protein purification by fusion with an environmentally responsive elastin-like polypeptide: effect of polypeptide length on the purification of thioredoxin. Biotechnol Prog, 2001; 17: 720-8.
14. Gupta, B., Levchenko, T. S., and Torchilin, V. P. Intracellular delivery of large molecules and small particles by cell-penetrating proteins and peptides. Adv Drug Deliv Rev, 2005; 57: 637-51.
15. Temsamani, J. and Vidal, P. The use of cell-penetrating peptides for drug delivery. Drug Discov Today, 2004; 9: 1012-9.
16. Graslund, A. and Eriksson, L. E. Properties and applications of cell-penetrating peptides. Genet Eng (N Y), 2004; 26: 19-31.
17. Derossi, D., Joliot, A. H., Chassaing, G., and Prochiantz, A. The third helix of the Antennapedia homeodomain translocates through biological membranes. J Biol Chem, 1994; 269: 10444-50.
18. Weeks, B. S., Desai, K., Loewenstein, P. M., Klotman, M. E., Klotman, P. E., Green, M., and Kleinman, H. K. Identification of a novel cell attachment domain in the HIV-1 Tat protein and its 90-kDa cell surface binding protein. J Biol Chem, 1993; 268: 5279-84.
19. Hawiger, J. Noninvasive intracellular delivery of functional peptides and proteins. Curr Opin Chem Biol, 1999; 3: 89-94.
20. Sadler, K., Eom, K. D., Yang, J. L., Dimitrova, Y., and Tam, J. P. Translocating proline-rich peptides from the antimicrobial peptide bactenecin 7. Biochemistry, 2002; 41: 14150-7.
21. Pooga, M., Hallbrink, M., Zorko, M., and Langel, U. Cell penetration by transportan. Faseb J, 1998; 12: 67-77.
22. Elmquist, A., Lindgren, M., Bartfai, T., and Langel, U. VE-cadherin-derived cell-penetrating peptide, pVEC, with carrier functions. Exp Cell Res, 2001; 269: 237-44.
23. Chelouche Lev, D. and Price, J. E. Therapeutic intervention with breast cancer metastasis. Crit Rev Eukaryot Gene Expr, 2002; 12: 137-50.
24. Kawaguchi, T. Cancer metastasis: characterization and identification of the behavior of metastatic tumor cells and the cell adhesion molecules, including carbohydrates. Curr Drug Targets Cardiovasc Haematol Disord, 2005; 5: 39-64.
25. Lacroix, M. and Leclercq, G. Relevance of breast cancer cell lines as models for breast tumours: an update. Breast Cancer Res Treat, 2004; 83: 249-89.
26. Rosol, T. J., Tannehill-Gregg, S. H., Corn, S., Schneider, A., and McCauley, L. K. Animal models of bone metastasis. Cancer Treat Res, 2004; 118: 47-81.

27. Thompson, E. W., Paik, S., Brunner, N., Sommers, C. L., Zugmaier, G., Clarke, R., Shima, T. B., Toni, J., Donahue, S., Lippman, M. E., and et al. Association of increased basement membrane invasiveness with absence of estrogen receptor and expression of vimentin in human breast cancer cell lines. J Cell Physiol, 1992; 150: 534-44.
28. Tester, A. M., Waltham, M., Oh, S. J., Bae, S. N., Bills, M. M., Walker, E. C., Kern, F. G., Stetler-Stevenson, W. G., Lippman, M. E., and Thompson, E. W. Pro-matrix metalloproteinase-2 transfection increases orthotopic primary growth and experimental metastasis of MDA-MB-231 human breast cancer cells in nude mice. Cancer Res, 2004; 64: 652-8.
29. Tester, A. M., Sharp, J. A., Dhanesuan, N., Waltham, M., and Thompson, E. W. Correlation between extent of osteolytic damage and metastatic burden of human breast cancer metastasis in nude mice: real-time PCR quantitation. Clin Exp Metastasis, 2002; 19: 377-83.
30. Bidwell, L. G., III and Raucher, D. Application of Thermally Responsive Polypeptides Directed against c-Myc Transcriptional Function for Cancer Therapy. Molecular Cancer Therapeutics, 2005; in press.
31. Voura, E. B., Sandig, M., and Siu, C. H. Cell-cell interactions during transendothelial migration of tumor cells. Microsc Res Tech, 1998; 43: 265-75.
32. Zhu, N., Lalla, R., Eves, P., Brown, T. L., King, A., Kemp, E. H., Haycock, J. W., and MacNeil, S. Melanoma cell migration is upregulated by tumour necrosis factor-alpha and suppressed by alpha-melanocyte-stimulating hormone. Br J Cancer, 2004; 90: 1457-63.
33. Anttila, M. A., Tammi, R. H., Tammi, M. I., Syrjanen, K. J., Saarikoski, S. V., and Kosma, V. M. High levels of stromal hyaluronan predict poor disease outcome in epithelial ovarian cancer. Cancer Res, 2000; 60: 150-5.
34. Massodi, I., Bidwell, G. L., 3rd, and Raucher, D. Evaluation of cell penetrating peptides fused to elastin-like polypeptide for drug delivery. J Control Release, 2005; 108: 396-408.
35. Zand, L., Qiang, F., Roskelley, C. D., Leung, P. C., and Auersperg, N. Differential effects of cellular fibronectin and plasma fibronectin on ovarian cancer cell adhesion, migration, and invasion. In Vitro Cell Dev Biol Anim, 2003; 39: 178-82.
36. Fjeldstad, K. and Kolset, S. O. Decreasing the metastatic potential in cancers—targeting the heparan sulfate proteoglycans. Curr Drug Targets, 2005; 6: 665-82.
37. Tarone, G., Galetto, G., Prat, M., and Comoglio, P. M. Cell surface molecules and fibronectin-mediated cell adhesion: effect of proteolytic digestion of membrane proteins. J Cell Biol, 1982; 94: 179-86.
38. Huang, K. G., Wang, C. J., Chang, T. C., Liou, J. D., Hsueh, S., Lai, C. H., and Huang, L. W. Management of port-site metastasis after laparoscopic surgery for ovarian cancer. Am J Obstet Gynecol, 2003; 189: 16-21.

Various changes in the details, steps and materials that have been described may be made by those skilled in the art within the principles and scope of the invention herein illustrated and defined in the appended claims. Therefore, while the present invention has been shown and described herein in what is believed to be the most practical and preferred embodiment, it is recognized that departures can be made therefrom within the scope of the invention, which is therefore not to be limited to the details disclosed herein but is to be accorded the full scope of the claims so as to embrace any and all equivalent apparatus and methods.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

We claim:

1. A method of inhibiting the metastasis of cancer, comprising:
   administering an effective amount of a compound comprising a cell penetrating peptide (CPP) and an elastin-like protein (ELP) to a subject having one or more cancer cells, the compound binding to an exterior surface of the one or more cancer cells thereby inhibiting adhesion, spreading, invasion and migration of the one or more cancer cells to a metastatic site; wherein the compound is not conjugated to a therapeutic agent, the CPP is selected from Tat, Penetratin, Bac-7, Transportan, pVEC, MTS, and combinations thereof, the ELP comprises the sequence (VPGXG (SEQ ID NO: 37))$_n$, where n is an integer from about 30 to about 200 and each X is independently selected from valine (Val; V), glycine (Gly; G), and alanine (Ala; A), and the cancer is selected from the group consisting of breast cancer, ovarian cancer, melanoma, and combinations thereof.

2. A method of inhibiting the metastasis of cancer, comprising:
   administering an effective amount of a compound comprising a cell penetrating peptide (CPP) and an elastin-like protein (ELP) to a subject having one or more cancer cells, the compound binding to an exterior surface of the one or more cancer cells thereby inhibiting adhesion, spreading, invasion and migration of the one or more cancer cells to a metastatic site; wherein the compound is not conjugated to a therapeutic agent, the CPP is selected from Tat, Bac-7, Transportan, pVEC, MTS, and combinations thereof, the ELP comprises the sequence (VPGXG (SEQ ID NO: 37))$_n$, where n is an integer from about 30 to about 200 and each X is independently selected from valine (Val; V), glycine (Gly; G), and alanine (Ala; A), and the cancer is selected from the group consisting of breast cancer, ovarian cancer, melanoma, and combinations thereof.

3. The method of claim 1 wherein the one or more cancer cells are circulating cells.

4. The method of claim 2 wherein the one or more cancer cells are circulating cells.

5. A method of inhibiting the metastasis of cancer, comprising:
   administering an effective amount of a compound consisting of a cell penetrating peptide (CPP) and an elastin-like protein (ELP) to a subject having one or more cancer cells, the compound binding to an exterior surface of the one or more cancer cells thereby inhibiting adhesion, spreading, invasion and migration of the one or more cancer cells to a metastatic site; wherein the CPP is selected from Tat, Penetratin, Bac-7, Transportan, pVEC, MTS, and combinations thereof, the ELP comprises the sequence (VPGXG (SEQ ID NO: 37))$_n$, where n is an integer from about 30 to about 200 and each X is independently selected from valine (Val; V), glycine (Gly; G), and alanine (Ala; A), and the cancer is selected from the group consisting of breast cancer, ovarian cancer, melanoma, and combinations thereof.

6. The method of claim 5 wherein the one or more cancer cells are circulating cells.

7. A method of inhibiting the metastasis of cancer, comprising:

administering an effective amount of a compound consisting of a cell penetrating peptide (CPP) and an elastin-like protein (ELP) to a subject having one or more cancer cells, the compound binding to an exterior surface of the one or more cancer cells thereby inhibiting adhesion, spreading, invasion and migration of the one or more cancer cells to a metastatic site; wherein the CPP is selected from Tat, Bac-7, Transportan, pVEC, MTS, and combinations thereof, the ELP comprises the sequence (VPGXG (SEQ ID NO: 37))$_n$, where n is an integer from about 30 to about 200 and each X is independently selected from valine (Val; V), glycine (Gly; G), and alanine (Ala; A), and the cancer is selected from the group consisting of breast cancer, ovarian cancer, melanoma, and combinations thereof.

8. The method of claim 7 wherein the one or more cancer cells are circulating cells.

\* \* \* \* \*